United States Patent
Wang et al.

(10) Patent No.: US 9,688,752 B2
(45) Date of Patent: *Jun. 27, 2017

(54) LOW ACIDIC SPECIES COMPOSITIONS AND METHODS FOR PRODUCING AND USING THE SAME USING DISPLACEMENT CHROMATOGRAPHY

(71) Applicant: AbbVie, Inc., North Chicago, IL (US)

(72) Inventors: Chen Wang, Shrewsbury, MA (US); Germano Coppola, Shrewsbury, MA (US); Chris Chumsae, North Andover, MA (US)

(73) Assignee: AbbVie Inc., North Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/635,505

(22) Filed: Mar. 2, 2015

(65) Prior Publication Data

US 2015/0166653 A1 Jun. 18, 2015

Related U.S. Application Data

(63) Continuation of application No. 14/079,076, filed on Nov. 13, 2013, which is a continuation of application (Continued)

(51) Int. Cl.
*C07K 16/00* (2006.01)
*C07K 16/24* (2006.01)
(Continued)

(52) U.S. Cl.
CPC ...... *C07K 16/241* (2013.01); *A61K 39/39591* (2013.01); *C07K 14/525* (2013.01);
(Continued)

(58) Field of Classification Search
CPC .... C07K 16/241; C07K 1/165; C07K 14/525; C07K 1/18; C07K 16/00; C07K 2317/14;
(Continued)

(56) References Cited

U.S. PATENT DOCUMENTS

| 3,887,430 A | 6/1975 | Torney et al. |
| RE30,985 E | 6/1982 | Cartaya |

(Continued)

FOREIGN PATENT DOCUMENTS

| CN | 1 563090 A | 1/2005 |
| CN | 105777895 A | 7/2016 |

(Continued)

OTHER PUBLICATIONS

"Genentech unveils production capacity hikes," in-Pharma Technologist.com Jun. 28, 2005, pp. 1-2.
(Continued)

*Primary Examiner* — Cherie M Stanfield
(74) *Attorney, Agent, or Firm* — McCarter & English, LLP; Maria Laccotripe Zacharakis; Marcie B. Clarke

(57) ABSTRACT

The present invention relates to low acidic species (AR) compositions comprising a protein, e.g., an antibody, or antigen-binding portion thereof, and methods for producing such low AR compositions using displacement chromatography. Methods for using such compositions to treat a disorder, e.g., a disorder in which TNFα is detrimental, are also provided.

28 Claims, 18 Drawing Sheets

Related U.S. Application Data

No. 14/077,576, filed on Nov. 12, 2013, now abandoned.

(60) Provisional application No. 61/892,833, filed on Oct. 18, 2013.

(51) Int. Cl.
| C07K 14/525 | (2006.01) |
| A61K 39/395 | (2006.01) |
| C07K 16/06 | (2006.01) |
| C07K 1/16 | (2006.01) |

(52) U.S. Cl.
CPC ............ *C07K 16/065* (2013.01); *C07K 1/165* (2013.01); *C07K 2317/565* (2013.01)

(58) Field of Classification Search
CPC ...... C07K 1/20; C07K 1/22; A61K 39/39591; C12P 21/00
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,925,796 A | 5/1990 | Bergh et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,047,335 A | 9/1991 | Paulson et al. |
| 5,096,816 A | 3/1992 | Maiorella |
| 5,110,913 A | 5/1992 | Coan et al. |
| 5,112,469 A | 5/1992 | Kempf et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,169,936 A | 12/1992 | Staples et al. |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,605,923 A | 2/1997 | Christensen, IV et al. |
| 5,616,487 A | 4/1997 | Palsson et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,730,975 A | 3/1998 | Hotamisligil et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,945,311 A | 8/1999 | Lindhofer et al. |
| 5,976,833 A | 11/1999 | Furukawa et al. |
| 5,989,830 A | 11/1999 | Davis et al. |
| 5,994,510 A | 11/1999 | Adair et al. |
| 6,005,082 A | 12/1999 | Smeds |
| 6,015,558 A | 1/2000 | Hotamisligil et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,093,324 A | 7/2000 | Bertolini et al. |
| 6,113,898 A | 9/2000 | Anderson et al. |
| 6,150,584 A | 11/2000 | Kuncherlapati et al. |
| 6,171,586 B1 | 1/2001 | Lam et al. |
| 6,171,825 B1 | 1/2001 | Chan et al. |
| 6,235,281 B1 | 5/2001 | Stenzel et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,303,626 B1 | 10/2001 | Abramovici et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,506,598 B1 | 1/2003 | Andersen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,656,466 B1 | 12/2003 | Etcheverry et al. |
| 6,673,575 B1 | 1/2004 | Franze et al. |
| 6,673,986 B1 | 1/2004 | Kuncherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,936,441 B2 | 8/2005 | Reiter et al. |
| 6,974,681 B1 | 12/2005 | McGrew |
| 7,029,872 B2 | 4/2006 | Gerngross |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,229,432 B2 | 6/2007 | Marshall et al. |
| 7,250,165 B2 | 7/2007 | Heavner et al. |
| 7,276,239 B2 | 10/2007 | Le et al. |
| 7,297,680 B2 | 11/2007 | Opstelten et al. |
| 7,323,553 B2 | 1/2008 | Fahrner et al. |
| 7,326,681 B2 | 2/2008 | Gerngross |
| 7,332,303 B2 | 2/2008 | Schilling et al. |
| 7,390,660 B2 | 6/2008 | Behrendt et al. |
| 7,427,659 B2 | 9/2008 | Shukla et al. |
| 7,429,491 B2 | 9/2008 | Luan et al. |
| 7,449,308 B2 | 11/2008 | Gerngross et al. |
| 7,473,680 B2 | 1/2009 | DeFrees et al. |
| 7,504,485 B2 | 3/2009 | Salfeld et al. |
| 7,517,670 B2 | 4/2009 | Umana et al. |
| 7,521,206 B2 | 4/2009 | Heavner et al. |
| 7,521,210 B2 | 4/2009 | Knudsen |

(56) References Cited

U.S. PATENT DOCUMENTS

| | | | |
|---|---|---|---|
| 7,541,031 B2 | 6/2009 | Salfeld et al. |
| 7,588,761 B2 | 9/2009 | Salfeld et al. |
| 7,612,181 B2 | 11/2009 | Wu et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,906,329 B2 | 3/2011 | Umana et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,043,863 B2 | 10/2011 | Bosques et al. |
| 8,053,236 B2 | 11/2011 | Morris et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,216,851 B2 | 7/2012 | Parsons et al. |
| 8,231,876 B2 | 7/2012 | Wan et al. |
| 8,304,250 B2 | 11/2012 | Parsons et al. |
| 8,313,925 B2 | 11/2012 | Gregory et al. |
| 8,338,088 B2 | 12/2012 | Collins et al. |
| 8,361,705 B2 | 1/2013 | Parsons et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,388,965 B2 | 3/2013 | Rao et al. |
| 8,399,627 B2 | 3/2013 | Votsmeier et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,318 B2 | 6/2013 | Ravetch et al. |
| 8,470,552 B2 | 6/2013 | Croughan et al. |
| 8,512,983 B2 | 8/2013 | Gawlitzek et al. |
| 8,530,192 B2 | 9/2013 | Knudsen |
| 8,586,356 B2 | 11/2013 | Bosques et al. |
| 8,623,644 B2 | 1/2014 | Umana et al. |
| 8,629,248 B2 | 1/2014 | Umana et al. |
| 8,632,773 B2 | 1/2014 | Kasermann et al. |
| 8,652,487 B2 | 2/2014 | Maldonado |
| 8,663,945 B2 | 3/2014 | Pla et al. |
| 8,663,999 B2 | 3/2014 | Parsons et al. |
| 8,703,498 B2 | 4/2014 | Parsons et al. |
| 8,729,241 B2 | 5/2014 | Liu et al. |
| 8,753,633 B2 | 6/2014 | Salfeld et al. |
| 8,821,865 B2 | 9/2014 | Neu et al. |
| 8,852,889 B2 | 10/2014 | Prentice |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 8,969,024 B2 | 3/2015 | Kaymakcalan et al. |
| 9,017,687 B1 * | 4/2015 | Wang .................. C07K 16/241 424/142.1 |
| 9,018,361 B2 | 4/2015 | Hickman et al. |
| 9,023,992 B2 | 5/2015 | Rasmussen et al. |
| 9,035,027 B2 | 5/2015 | Ghayur et al. |
| 9,062,106 B2 | 6/2015 | Bengea et al. |
| 9,067,990 B2 * | 6/2015 | Wang .................. C07K 16/241 |
| 9,073,988 B2 | 7/2015 | Pla et al. |
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 9,090,867 B2 | 7/2015 | Pla et al. |
| 9,096,666 B2 | 8/2015 | Wan et al. |
| 9,096,879 B2 | 8/2015 | Khetan et al. |
| 9,102,723 B2 | 8/2015 | Wan et al. |
| 9,103,821 B2 | 8/2015 | Bosques et al. |
| 9,109,010 B2 | 8/2015 | Hickman et al. |
| 9,144,755 B2 | 9/2015 | Brown et al. |
| 9,145,546 B2 | 9/2015 | Nurcombe et al. |
| 9,150,645 B2 | 10/2015 | Subramanian et al. |
| 9,181,337 B2 | 11/2015 | Subramanian et al. |
| 9,181,572 B2 | 11/2015 | Subramanian et al. |
| 9,182,467 B2 | 11/2015 | Parsons et al. |
| 9,200,069 B2 | 12/2015 | Ramasubramanyan et al. |
| 9,200,070 B2 | 12/2015 | Ramasubramanyan et al. |
| 9,206,390 B2 | 12/2015 | Rives et al. |
| 9,234,032 B2 | 1/2016 | Pla et al. |
| 9,234,033 B2 | 1/2016 | Rives et al. |
| 9,249,182 B2 | 2/2016 | Herigstad et al. |
| 9,255,143 B2 | 2/2016 | Bengea et al. |
| 9,265,815 B2 | 2/2016 | Fraser et al. |
| 9,266,949 B2 | 2/2016 | Ramasubramanyan et al. |
| 9,273,132 B2 | 3/2016 | Wan et al. |
| 9,284,371 B2 | 3/2016 | Pla et al. |
| 9,290,568 B2 | 3/2016 | Rives et al. |
| 9,315,574 B2 * | 4/2016 | Ramasubramanyan |
| 9,328,165 B2 | 5/2016 | Wan et al. |
| 9,334,319 B2 | 5/2016 | Ramasubramanyan et al. |
| 9,346,879 B2 * | 5/2016 | Ramasubramanyan C07K 1/165 |
| 9,359,434 B2 | 6/2016 | Subramanian et al. |
| 9,365,645 B1 | 6/2016 | Bengea et al. |
| 9,499,614 B2 | 11/2016 | Hossler et al. |
| 9,505,834 B2 | 11/2016 | Bengea et al. |
| 2001/0021525 A1 | 9/2001 | Hirai et al. |
| 2002/0045207 A1 | 4/2002 | Krummen et al. |
| 2002/0119530 A1 | 8/2002 | Maiorella et al. |
| 2002/0132299 A1 | 9/2002 | Field |
| 2002/0137673 A1 | 9/2002 | Pingel et al. |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0170813 A1 | 9/2003 | Suga et al. |
| 2003/0175884 A1 | 9/2003 | Umana et al. |
| 2003/0178368 A1 | 9/2003 | van Reis |
| 2003/0203448 A1 | 10/2003 | Reiter et al. |
| 2003/0206898 A1 | 11/2003 | Fischkoff et al. |
| 2003/0211573 A1 | 11/2003 | Ryll |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0043446 A1 | 3/2004 | DeFrees et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136986 A1 | 7/2004 | Raju |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0191256 A1 | 9/2004 | Raju |
| 2004/0214289 A1 | 10/2004 | deVries et al. |

(56) References Cited

U.S. PATENT DOCUMENTS

| | | |
|---|---|---|
| 2004/0219142 A1 | 11/2004 | Banerjee et al. |
| 2005/0004354 A1 | 1/2005 | Salfeld et al. |
| 2005/0084969 A1 | 4/2005 | Schorgendorfer et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0057638 A1 | 3/2006 | Bosques et al. |
| 2006/0083741 A1 | 4/2006 | Hoffman et al. |
| 2006/0127950 A1 | 6/2006 | Bosques et al. |
| 2006/0149042 A1 | 7/2006 | Konstantinov et al. |
| 2006/0223147 A1 | 10/2006 | Nishiya et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0275867 A1 | 12/2006 | Chotteau et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0015239 A1 | 1/2007 | Bihoreau et al. |
| 2007/0020260 A1 | 1/2007 | Presta |
| 2007/0041905 A1 | 2/2007 | Hoffman et al. |
| 2007/0054390 A1 | 3/2007 | Kelley et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0212770 A1 | 9/2007 | Grillberger et al. |
| 2007/0248600 A1 | 10/2007 | Hansen et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0009040 A1 | 1/2008 | Grillberger et al. |
| 2008/0025976 A1 | 1/2008 | Le et al. |
| 2008/0058507 A1 | 3/2008 | Liu et al. |
| 2008/0095762 A1 | 4/2008 | Presta |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0206246 A1 | 8/2008 | Ravetch et al. |
| 2008/0219952 A1 | 9/2008 | Fischer et al. |
| 2008/0226635 A1 | 9/2008 | Koll et al. |
| 2008/0227136 A1 | 9/2008 | Pla et al. |
| 2008/0254514 A1 | 10/2008 | Knudsen |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0069232 A1 | 3/2009 | Callewaert et al. |
| 2009/0110679 A1 | 4/2009 | Li et al. |
| 2009/0123378 A1 | 5/2009 | Wong et al. |
| 2009/0136525 A1 | 5/2009 | Gerngross et al. |
| 2009/0142828 A1 | 6/2009 | Bucciarelli et al. |
| 2009/0148513 A1 | 6/2009 | Fraunhofer et al. |
| 2009/0151023 A1 | 6/2009 | Kuvshinov et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0253174 A1 | 10/2009 | Serber et al. |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0004907 A1 | 1/2010 | Kidal et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0069617 A1 | 3/2010 | Gagnon |
| 2010/0113294 A1 | 5/2010 | Venkataraman et al. |
| 2010/0120094 A1 | 5/2010 | Johnsen et al. |
| 2010/0135987 A1 | 6/2010 | Hickman et al. |
| 2010/0136025 A1 | 6/2010 | Hickman et al. |
| 2010/0145029 A1 | 6/2010 | Gagnon |
| 2010/0151499 A1 | 6/2010 | Collins et al. |
| 2010/0160894 A1 | 6/2010 | Julian et al. |
| 2010/0167313 A1 | 7/2010 | Essig et al. |
| 2010/0172911 A1 | 7/2010 | Naso et al. |
| 2010/0189717 A1 | 7/2010 | Kim et al. |
| 2010/0221823 A1 | 9/2010 | McCoy et al. |
| 2010/0255013 A1 | 10/2010 | Presta |
| 2010/0256336 A1 | 10/2010 | Yuk et al. |
| 2010/0278808 A1 | 11/2010 | Ravetch et al. |
| 2010/0278822 A1 | 11/2010 | Fraunhofer et al. |
| 2010/0279306 A1 | 11/2010 | Bosques et al. |
| 2010/0291624 A1 | 11/2010 | Zhang et al. |
| 2010/0292443 A1 | 11/2010 | Sabbadini et al. |
| 2010/0297609 A1 | 11/2010 | Wells et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0039300 A1 | 2/2011 | Bayer et al. |
| 2011/0039729 A1 | 2/2011 | Delisa et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086050 A1 | 4/2011 | Presta |
| 2011/0086798 A1 | 4/2011 | Sethuraman et al. |
| 2011/0097336 A1 | 4/2011 | Wu et al. |
| 2011/0117601 A1 | 5/2011 | Haberger et al. |
| 2011/0123544 A1 | 5/2011 | Salfeld et al. |
| 2011/0124024 A1 | 5/2011 | Raju et al. |
| 2011/0129468 A1 | 6/2011 | Mccue et al. |
| 2011/0130544 A1 | 6/2011 | Ram et al. |
| 2011/0136682 A1 | 6/2011 | Bosques et al. |
| 2011/0171227 A1 | 7/2011 | Okun et al. |
| 2011/0207676 A1 | 8/2011 | Callewaert et al. |
| 2011/0213137 A1 | 9/2011 | Bosques et al. |
| 2011/0263828 A1 | 10/2011 | Wong et al. |
| 2011/0300151 A1 | 12/2011 | Okun et al. |
| 2011/0318340 A1 | 12/2011 | Collin et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |

(56) References Cited

U.S. PATENT DOCUMENTS

| | | |
|---|---|---|
| 2012/0077213 A1 | 3/2012 | Pla et al. |
| 2012/0093810 A1 | 4/2012 | Takada et al. |
| 2012/0107783 A1 | 5/2012 | Julian et al. |
| 2012/0107874 A1 | 5/2012 | Liu et al. |
| 2012/0122076 A1 | 5/2012 | Lau et al. |
| 2012/0122759 A1 | 5/2012 | Brown et al. |
| 2012/0123688 A1 | 5/2012 | Ramasubramanyan et al. |
| 2012/0129185 A1 | 5/2012 | Maksymowych et al. |
| 2012/0134988 A1 | 5/2012 | Ravetch et al. |
| 2012/0171123 A1 | 7/2012 | Medich et al. |
| 2012/0177596 A1 | 7/2012 | Fischkoff et al. |
| 2012/0177640 A1 | 7/2012 | Burg et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0195885 A1 | 8/2012 | Correia et al. |
| 2012/0201831 A1 | 8/2012 | Salfeld et al. |
| 2012/0202974 A1 | 8/2012 | Eon-Duval et al. |
| 2012/0213792 A1 | 8/2012 | Salfeld et al. |
| 2012/0219564 A1 | 8/2012 | Salfeld et al. |
| 2012/0230913 A1 | 9/2012 | Johnston et al. |
| 2012/0238730 A1 | 9/2012 | Dong et al. |
| 2012/0244168 A1 | 9/2012 | Salfeld et al. |
| 2012/0251541 A1 | 10/2012 | Baurin et al. |
| 2012/0251550 A1 | 10/2012 | Borhani et al. |
| 2012/0258114 A1 | 10/2012 | Salfeld et al. |
| 2012/0258496 A1 | 10/2012 | Ellwanger et al. |
| 2012/0263731 A1 | 10/2012 | Fraunhofer et al. |
| 2012/0264920 A1 | 10/2012 | Wang et al. |
| 2012/0264927 A1 | 10/2012 | Parsons et al. |
| 2012/0271041 A1 | 10/2012 | Ficko Trcek |
| 2012/0276109 A1 | 11/2012 | Fraser et al. |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276160 A1 | 11/2012 | Maldonado |
| 2012/0276631 A1 | 11/2012 | Bengea et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308514 A1 | 12/2012 | Salfeld et al. |
| 2012/0309056 A1 | 12/2012 | Leon et al. |
| 2012/0329709 A1 | 12/2012 | Collins et al. |
| 2013/0004507 A1 | 1/2013 | Fischkoff et al. |
| 2013/0028903 A1 | 1/2013 | Wan et al. |
| 2013/0309242 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0149300 A1 | 6/2013 | Hiatt et al. |
| 2013/0156760 A1 | 6/2013 | Fraunhofer et al. |
| 2013/0189737 A1 | 7/2013 | Kang et al. |
| 2013/0195888 A1 | 8/2013 | Wang et al. |
| 2013/0205604 A1 | 8/2013 | Esenwein et al. |
| 2013/0231255 A1 | 9/2013 | Collins et al. |
| 2013/0243786 A1 | 9/2013 | Banerjee et al. |
| 2013/0244280 A1 | 9/2013 | Parikh et al. |
| 2013/0245139 A1 | 9/2013 | Kozlov et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0045212 A1 | 2/2014 | Bosques et al. |
| 2014/0046032 A1 | 2/2014 | Blanche et al. |
| 2014/0065710 A1 | 3/2014 | Rives et al. |
| 2014/0072585 A1 | 3/2014 | Herigstad et al. |
| 2014/0087423 A1 | 3/2014 | Koncilja et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0199340 A1 | 7/2014 | Maldonado |
| 2014/0199729 A1 | 7/2014 | Srivastava et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271622 A1 | 9/2014 | Prentice |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0273057 A1 | 9/2014 | Prentice et al. |
| 2014/0274911 A1 | 9/2014 | Collins et al. |
| 2014/0274912 A1 | 9/2014 | Prentice |
| 2014/0275494 A1 | 9/2014 | Wang et al. |
| 2014/0288272 A1 | 9/2014 | Allison et al. |
| 2014/0288278 A1 | 9/2014 | Nti-gyabaah et al. |
| 2014/0296490 A1 | 10/2014 | Faid et al. |
| 2014/0301977 A1 | 10/2014 | Nadarajah et al. |
| 2014/0314745 A1 | 10/2014 | Rives et al. |
| 2014/0363845 A1 | 12/2014 | Sinacore et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0125905 A1 | 5/2015 | Pla et al. |
| 2015/0132320 A1 | 5/2015 | Chumsae et al. |
| 2015/0132801 A1 | 5/2015 | Ramasubramanyan et al. |
| 2015/0133639 A1 | 5/2015 | Wentz et al. |
| 2015/0139988 A1 | 5/2015 | Labkovsky et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |
| 2015/0197579 A1 | 7/2015 | Stefan et al. |
| 2015/0210735 A1 | 7/2015 | Hickman et al. |
| 2015/0259410 A1 | 9/2015 | Ramasubramanyan et al. |
| 2015/0299249 A1 | 10/2015 | Herigstad et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328333 A1 | 11/2015 | Fraser et al. |
| 2015/0329588 A1* | 11/2015 | Wang .................. C07K 16/241 530/388.15 |
| 2015/0335762 A1 | 11/2015 | Fraser et al. |
| 2015/0344564 A1 | 12/2015 | Hickman et al. |
| 2015/0361169 A1 | 12/2015 | Wan et al. |
| 2015/0361170 A1 | 12/2015 | Fraunhofer et al. |
| 2016/0017030 A1 | 1/2016 | Neu et al. |
| 2016/0017281 A1 | 1/2016 | Sunstrom |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0039924 A1 | 2/2016 | Zeng |
| 2016/0039925 A1 | 2/2016 | Subramanian et al. |
| 2016/0046708 A1 | 2/2016 | Subramanian et al. |
| 2016/0068881 A1 | 3/2016 | Prentice |
| 2016/0083452 A1 | 3/2016 | Hickman et al. |
| 2016/0115193 A1 | 4/2016 | Herigstad et al. |
| 2016/0115195 A1 | 4/2016 | Mendiratta et al. |
| 2016/0122384 A1 | 5/2016 | Kim et al. |
| 2016/0138064 A1 | 5/2016 | Rives et al. |

(56) References Cited

U.S. PATENT DOCUMENTS

| | | |
|---|---|---|
| 2016/0145331 A1 | 5/2016 | Subramanian et al. |
| 2016/0159897 A1 | 6/2016 | Zeng |
| 2016/0185848 A1 | 6/2016 | Hossler et al. |
| 2016/0186130 A1 | 6/2016 | Pla et al. |
| 2016/0194390 A1 | 7/2016 | Ramasubramanyan et al. |
| 2016/0201028 A1 | 7/2016 | Trcek |
| 2016/0207922 A1 | 7/2016 | Tang et al. |
| 2016/0207992 A1 | 7/2016 | Bengea et al. |
| 2016/0215319 A1 | 7/2016 | Mendiratta et al. |
| 2016/0222101 A1 | 8/2016 | Fraunhofer et al. |
| 2016/0227381 A1 | 8/2016 | Bargetzi et al. |
| 2016/0237149 A1 | 8/2016 | Flikweert et al. |
| 2016/0237150 A1 | 8/2016 | Subramanian et al. |
| 2016/0280767 A1 | 9/2016 | Beri et al. |

FOREIGN PATENT DOCUMENTS

| | | |
|---|---|---|
| CN | 105777896 A | 7/2016 |
| CN | 105777904 A | 7/2016 |
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 230584 A1 | 8/1987 |
| EP | 0351789 A2 | 1/1990 |
| EP | 0366043 A1 | 5/1990 |
| EP | 374510 A1 | 6/1990 |
| EP | 453898 A2 | 10/1991 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 585705 A1 | 3/1994 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1176195 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1849862 A2 | 10/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2500414 A1 | 9/2012 |
| EP | 2528002 A2 | 11/2012 |
| EP | 2574677 A1 | 4/2013 |
| EP | 3036254 A1 | 6/2016 |
| EP | 3036320 A1 | 6/2016 |
| EP | 3072957 | 9/2016 |
| GB | 2160530 A | 12/1985 |
| GB | 2279077 A | 12/1994 |
| IN | 2285/MUM/2013 A1 | 1/2015 |
| JP | 6-292592 | 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/11383 A1 | 7/1992 |
| WO | WO-92/16221 A1 | 10/1992 |
| WO | WO-92/16553 A1 | 10/1992 |
| WO | WO-92/17583 A1 | 10/1992 |
| WO | WO-93/06213 A1 | 4/1993 |
| WO | WO-93/11793 A1 | 6/1993 |
| WO | WO-94/02602 A1 | 2/1994 |
| WO | WO-94/08619 A1 | 4/1994 |
| WO | WO-94/20139 A1 | 9/1994 |
| WO | WO-94/25585 A1 | 11/1994 |
| WO | WO-94/26910 A1 | 11/1994 |
| WO | WO-94/29347 A1 | 12/1994 |
| WO | WO-95/11317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98-08934 A1 | 3/1998 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |
| WO | WO-98/58964 A1 | 12/1998 |
| WO | WO-99/22764 A1 | 5/1999 |
| WO | WO-99/32605 A1 | 7/1999 |
| WO | WO-99/54342 A1 | 10/1999 |
| WO | WO-99/57134 A1 | 11/1999 |
| WO | WO-99/57246 A1 | 11/1999 |
| WO | WO-00/03000 A2 | 1/2000 |
| WO | WO-01/44442 A1 | 6/2001 |
| WO | WO-01/47554 A1 | 7/2001 |
| WO | WO-01/59069 A1 | 8/2001 |
| WO | WO-01/77362 A1 | 10/2001 |
| WO | WO-02/12501 A2 | 2/2002 |
| WO | WO-02/12502 A2 | 2/2002 |
| WO | WO-02/076578 A1 | 10/2002 |
| WO | WO-02/094192 A2 | 11/2002 |
| WO | WO-02/101019 A2 | 12/2002 |
| WO | WO-03/045995 A2 | 6/2003 |
| WO | WO-03/046162 | 6/2003 |
| WO | WO-03/059935 A2 | 7/2003 |
| WO | WO-03/066662 A2 | 8/2003 |
| WO | WO-03/102132 A2 | 12/2003 |
| WO | WO-2004/008100 A2 | 1/2004 |
| WO | WO-2004009776 A2 | 1/2004 |
| WO | WO-2004/026891 A2 | 4/2004 |
| WO | WO-2004/058800 A2 | 7/2004 |
| WO | WO-2004/058944 A2 | 7/2004 |
| WO | WO-2004/076485 A2 | 9/2004 |
| WO | WO-2004/097006 A1 | 11/2004 |
| WO | WO-2005/042569 A1 | 5/2005 |
| WO | WO-2005-062967 A2 | 7/2005 |
| WO | WO-2005/063813 A2 | 7/2005 |
| WO | WO-2005/082483 A1 | 9/2005 |
| WO | WO-2005100584 A2 | 10/2005 |
| WO | WO-2006/014683 A2 | 2/2006 |
| WO | WO-2006/026445 A1 | 3/2006 |
| WO | WO-2006/043895 A1 | 4/2006 |
| WO | WO-2006/045438 A1 | 5/2006 |
| WO | WO-2006/099308 A2 | 9/2006 |
| WO | WO-2006/110277 A1 | 10/2006 |
| WO | WO-2007-005786 A2 | 1/2007 |
| WO | WO-2007/024743 A2 | 3/2007 |
| WO | WO-2007/055916 A2 | 5/2007 |
| WO | WO-2007/070315 A2 | 6/2007 |
| WO | WO-2007-077217 A2 | 7/2007 |
| WO | WO-2007/087384 A2 | 8/2007 |
| WO | WO-2007/117490 A2 | 10/2007 |
| WO | WO-2007/117505 A2 | 10/2007 |
| WO | WO-2008/008360 A1 | 1/2008 |
| WO | WO-2008/028686 A2 | 3/2008 |

(56) References Cited

FOREIGN PATENT DOCUMENTS

| | | |
|---|---|---|
| WO | WO-2008/033517 A2 | 3/2008 |
| WO | WO-2008/057240 A2 | 5/2008 |
| WO | WO-2008/057634 A2 | 5/2008 |
| WO | WO-2008/068879 A1 | 6/2008 |
| WO | WO-2008/077545 A1 | 7/2008 |
| WO | WO-2008/087184 A2 | 7/2008 |
| WO | WO-2008/121616 A2 | 10/2008 |
| WO | WO-2008/128230 A1 | 10/2008 |
| WO | WO-2008/135498 A2 | 11/2008 |
| WO | WO-2009/027041 A1 | 1/2009 |
| WO | WO-2009/017491 A1 | 2/2009 |
| WO | WO-2009/023562 A2 | 2/2009 |
| WO | WO-2009/058769 A1 | 5/2009 |
| WO | WO-2009/073569 A2 | 6/2009 |
| WO | WO-2009/079382 A1 | 6/2009 |
| WO | WO-2009/135656 A1 | 11/2009 |
| WO | WO-2010/036443 A1 | 4/2010 |
| WO | WO-2010/043703 A1 | 4/2010 |
| WO | WO-2010-048183 A1 | 4/2010 |
| WO | WO-2010/080062 A1 | 7/2010 |
| WO | WO-2010/102114 A1 | 9/2010 |
| WO | WO-2010/111633 A2 | 9/2010 |
| WO | WO-2010/122460 A1 | 10/2010 |
| WO | WO-2010/127069 A1 | 11/2010 |
| WO | WO-2010/129469 A1 | 11/2010 |
| WO | WO-2010/136209 A1 | 12/2010 |
| WO | WO-2010/138502 A2 | 12/2010 |
| WO | WO-2010/141039 A1 | 12/2010 |
| WO | WO-2011/005773 A2 | 1/2011 |
| WO | WO-2011/009623 A1 | 1/2011 |
| WO | WO-2011/015926 A1 | 2/2011 |
| WO | WO-2011/019619 A1 | 2/2011 |
| WO | WO-2011/024025 A1 | 3/2011 |
| WO | WO-2011/044180 A1 | 4/2011 |
| WO | WO-2011/069056 A2 | 6/2011 |
| WO | WO-2011/073235 A1 | 6/2011 |
| WO | WO-2011/098526 A1 | 8/2011 |
| WO | WO-2011/110598 A1 | 9/2011 |
| WO | WO-2011/127322 A1 | 10/2011 |
| WO | WO-2011/133886 A2 | 10/2011 |
| WO | WO-2011133902 A2 | 10/2011 |
| WO | WO-2011/134919 A2 | 11/2011 |
| WO | WO-2011/134920 A1 | 11/2011 |
| WO | WO-2012/014183 A1 | 2/2012 |
| WO | WO-2012/019160 A1 | 2/2012 |
| WO | WO-2012/030512 A1 | 3/2012 |
| WO | WO-2012/046255 A2 | 4/2012 |
| WO | WO-2012/050175 A1 | 4/2012 |
| WO | WO-2012/051147 A1 | 4/2012 |
| WO | WO-2012/062810 A2 | 5/2012 |
| WO | WO-2012/065072 A2 | 5/2012 |
| WO | WO-2012/068134 A1 | 5/2012 |
| WO | WO-2012/078376 A1 | 6/2012 |
| WO | WO-2012/120500 A2 | 9/2012 |
| WO | WO-2012/140138 A1 | 10/2012 |
| WO | WO-2012/145682 A1 | 10/2012 |
| WO | WO-2012/147048 A2 | 11/2012 |
| WO | WO-2012/147053 A1 | 11/2012 |
| WO | WO-2012/149197 A2 | 11/2012 |
| WO | WO-2012/158551 A1 | 11/2012 |
| WO | WO-2013/006461 A1 | 1/2013 |
| WO | WO-2013/006479 A2 | 1/2013 |
| WO | WO-2013/009648 A2 | 1/2013 |
| WO | WO-2013/011076 A2 | 1/2013 |
| WO | WO-2013/013013 A2 | 1/2013 |
| WO | WO-2013/021279 A2 | 2/2013 |
| WO | WO-2013-066707 A1 | 5/2013 |
| WO | WO-2013/067301 A1 | 5/2013 |
| WO | WO-2013/095966 A1 | 6/2013 |
| WO | WO-2013/158273 A1 | 10/2013 |
| WO | WO-2013/158275 A1 | 10/2013 |
| WO | WO-2013/158279 A1 | 10/2013 |
| WO | WO-2013-164837 A1 | 11/2013 |
| WO | WO-2013/176754 A1 | 11/2013 |
| WO | WO-2013/177115 A2 | 11/2013 |
| WO | WO-2013/177118 A2 | 11/2013 |
| WO | WO-2013/181585 A2 | 12/2013 |
| WO | WO-2013-186230 A1 | 12/2013 |
| WO | WO-2014/018747 A2 | 1/2014 |
| WO | WO-2014/039903 A2 | 3/2014 |
| WO | WO-2014/052360 A2 | 4/2014 |
| WO | WO-2014/096672 A1 | 6/2014 |
| WO | WO-2014/099636 A1 | 6/2014 |
| WO | WO-2014/125374 A2 | 8/2014 |
| WO | WO-2014-149935 A1 | 9/2014 |
| WO | WO-2014/150655 A1 | 9/2014 |
| WO | WO-2014/151878 A2 | 9/2014 |
| WO | WO-2014/158231 A1 | 10/2014 |
| WO | WO-2014/159488 A1 | 10/2014 |
| WO | WO-2014/159494 A1 | 10/2014 |
| WO | WO-2014/159499 A1 | 10/2014 |
| WO | WO-2014/179601 A2 | 11/2014 |
| WO | WO-2014-196780 A1 | 12/2014 |
| WO | WO-2014/207763 A1 | 12/2014 |
| WO | WO-2015/004679 A1 | 1/2015 |
| WO | WO-2015/007912 A1 | 1/2015 |
| WO | WO-2015/051293 A2 | 4/2015 |
| WO | WO-2015/073884 A2 | 5/2015 |
| WO | WO-2015/115849 A1 | 8/2015 |
| WO | WO-2016/007764 A1 | 1/2016 |
| WO | WO-2016/102383 A1 | 6/2016 |

OTHER PUBLICATIONS

"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.

"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.

"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS, 21 pages.

"Memorandum in Support of Centocor's Motion No. 3 for Summary Judgment that the 394 and 031 Patents Are Invalid for Under 35 U.S.C. §102(f) for Failing to Name the Proper Investors", dated Aug. 1, 2013 and submitted by defendant in Civil Action No. 09-40089-FDS, 13 pages.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.

"Plaintiffs' Memorandum in Support of Their Motion for Partial Summary Judgment", dated Aug. 1, 2013 and submitted by plaintiff in Civil Action No. 09-40089-FDS, 49 pages.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al., "Aggressive cutaneous T-cell lymphomas after TNFα blockade," J. Am. Acad. Dermatol 2004;51 :660-2.

Ahmed, M. U.et al.; N-(Carboxyethyl)lysine, a product of the chemical modification of proteins by methylglyoxal, increases with age in human lens proteins; Biochem. J. 1997, 324, 565-570.

Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.

(56) References Cited

OTHER PUBLICATIONS

Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Altamirano, C., et al., "Strategies for fed batch cultivation of t-PA producing CHO cells: substitution of glucose and glutamine and rational design of culture medium", J. Biotechn. 110:171-179, 2004.
Andersen DC, Goochee CF. The effect of cell-culture conditions on the oligosaccharide structures of secreted glycoproteins. Curr Opin Biotechnol. Oct. 1994;5(5):546-9.
Anonymous, "SACHEM Displacement Chromatography," Aug. 29, 2012, Retrieved from the internet: <www.displacementchromatography.com>, retrieved on Jul. 30, 2014.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Averginos, Gab '04 Abstracts—GE Healthcare Life Sciences, "HUMIRA manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Awdeh, Z.L., A.R. Williamson, and B.A. Askonas, One cell-one immunoglobulin. Origin of limited heterogeneity of myeloma proteins. Biochem J, 1970. 116(2): p. 241-8.
Azevedo et al., "Integrated Process for the Purification of Antibodies Combining Aqueous Two-Phase Extraction, Hydrophobic Interaction Chromatography and Size-Exclusion Chromatography", Journal of Chromatography (2008) 1213(2): 154-161.
Ballez, J.S. et al., "Plant protein hydrolysates support CHO-320 cells proliferation and recombinant IFN-[gamma] production in suspension and inside microcarriers in protein-free media", Cytotechnology 44:3, 103-114, 2004.
Barbuto, J. et al. "Production of Neutralizing Antibodies to Tumor Necrosis Factor by Human Tumor-Infiltrating B Lymphocytes" Proc. Am. Assoc. Cancer Res,. 34:487, Abstr. 2904 (1993).
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) <www.bdbiosciences.com/external_files/Doc_Recon_2.0/ab/others/Phytone_Soytone.pdf>//www.bdbiosciences.com/external_files/Doc_Recon 2.0/ab/others/Phytone_Soytone.pdf>), (last accessed Jan. 8, 2015), 4 pages.
Bendtzen, K. et al. "Auto-antibodies to IL-1α and TNFα in Normal Individuals and in Infectious and Immunoinflammatory Disorders" The Physiological and Pathological Effects of Cytokines, 447-52 (1990).
Biblia, T.A. et al., "In Pursuit of the Optimal Fed-Batch Process for Monoclonal Antibody Production", Biotechnol. Prog 11(1):1-13, Jan.-Feb. 1995.
Birch, JR. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Biastoff, S.; et al.; Colorimetric Activity Measurement of a Recombinant Putrescine N-Methyltransferase from Datura stramonium; Planta Med. 2006, 72, 1136.
Boekstegers, P., et al., "Repeated administration of a F(ab')2 fragment of an anti-tumor necrosis factor alpha monoclonal antibody in patients with severe sepsis: effects on the cardiovascular system and cytokine levels," Shock, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" Cell. Immunol., 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" Cell. Immunol., 152:569-81 (1993).
Brekke, O. et al., "Therapeutic Antibodies for Human Diseases at the Dawn of the Twenty-first Century," Nature, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).
Bruggemann, M., Neuberger, M.S., "Strategies for expressing human antibody repertoires in transgenic mice," Immunol. Today 17:391-397 (1996).
Burteau et al. (In Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al., "Humanization of an anti-p185HER2 antibody for human cancer therapy," Proc. Nat. Acad. Sci89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Charter, Edward A., "A New Process for the Separation and Purification of Egg Yolk; Antibodies," BASc., The University of British Columbia; A Thesis; Apr. 1993, 163 pages.
Chelius, D. et al.; Identification and Characterization of Deamidation Sites in the Conserved Regions of Human Immunoglobulin Gamma Antibodies, Anal. Chem. 2005, 77,6004-6011.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" Clinical Research, 42:2 299A (1994).
Chua, FKF et al., "Hyper-stimulation of monoclonal antibody production by high osmolarity stress in eRDF medium", J. Biotechnology 37(3):265-275, Nov. 15, 1994.

(56) References Cited

OTHER PUBLICATIONS

Chumsae, C., et al., Comparison of methionine oxidation in thermal stability and chemically stressed samples of a fully human monoclonal antibody. Journal of Chromatography B, 2007. 850(1-2): p. 285-294.

Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.

Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013(Dec. 3, 2013), pp. 11401-11409.

Chung et al., "Utilization of Lysozyme Charge Ladders to Examine the Effects of Protein Surface; Charge Distribution on Bindinq Affinity in Ion Exchange Systems," Langmuir 26(2): 759-768 (2010).

Chung et al. "Cetuximab-induced anaphylaxis and IgE specific for galactose-a-1,3-galactose" NEJM 358:11, 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.

Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).

Cordoba, A.J., et al., Non-enzymatic hinge region fragmentation of antibodies in solution. Journal of Chromatography B, 2005. 818(2): p. 115-121.

Cox, J. et al. "A directory of human germ-line Vκ segments reveals a strong bias in their usage" *Eur. J. Immunol.*, 24(2):827-36 (1994).

Cromwell (GAB'04 Abstracts—GE Healthcare Life Sciences, Franc Oct. 3-5, 2004, pp. 17-18 published 2005).

Crowell, C.K., et al., Amino acid and manganese supplementation modulates the glycosylation state of erythropoietin in a CHO culture system. Biotechnology and bioengineering, Feb. 15, 2007; 96(3):538-549.

Dai, S.; An Integrated Proteomic Analysis of Major Isoaspartyl-Containing Proteins in the Urine of Wild Type and Protein Llsoaspartate O-Methyltransferase-Deficient Mice; Anal. Chem. 2013, 85, 2423-2430.

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." Biotechnology, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

DeZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.

Dobo, A. & Kaltashov, I. A.; Detection of Multiple Protein Conformational Ensembles in Solution via Deconvolution of Charge-State Distributions in ESI MS; Anal. Chem. 2001,73, 4763-4773.

Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).

Doring, E., "Identification and Characterization of a TNFa Antagonist Derived from a Monoclonal Antibody" (1994) *Mol. Immunol* .31(14): 1059-1067.

Du et aL, "Chromatographic analysis of the acidic and basic species of recombinant monoclonal antibodies" MAbs, Sep.-Oct. 2012; 4(5):578-85.

Elliot et al., "Repeated therapy with monoclonal antibody to tumour necrosis factor α (cA2) in patients with rheumatoid arthritis" (1994) *Lancet*, 344:1125-1127.

Elliot, "Treatment of rheumatoid arthritis with chimeric monoclonal antibodies to tumor necrosis factor α" (1993) *Arthritis & Rheumatism*, 36(12):1681-1690.

Ellison, Jay W. et al., "The Nucleotide Sequence of a Human Immunoglobulin Cγ1 Gene," Nucleic Acids Research, vol. 10, No. 13 (1982), 9 pages.

Emery, P. "Adalimumab therapy: Clinical findings and implications for integration into clinical guidelines for rheumatoid arthritis." *Drugs of Today*, 41(3): p. 155-153. (2005).

Erbitux (cetuximab) label, *Revised* Aug. 2013, 8 pages.

European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.

Ewert et al., "Biophysical Properties of Human Antibody Variable Domains," J. Mol. Biol. 324: 531-; 553 (2003).

Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.

Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.

Exhibit dated Aug. 1, 2013 and cited by plaintiff in Civil Action No. 09-40089-FDS providing excerpts from the File History of U.S. Appl. No. 12/578,487, 5 pages.

Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX., 42 pages.

Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA., 71 pages.

Exhibit dated Aug. 1, 2013 and cited by plaintiff in Civil Action No. 09-40089-FDS providing Declaration by Jochen Salfeld, dated Jan. 17, 2013, 40 pages.

FDA Package insert for Adalimumab, Sep. 26, 2003, pp. 1-16.

Feldmann, "Anti-TNF-alpha Therapy of Rheumatoid Arthritis: What Have We Learned?" (2001) *Annu. Rev. Immunol.*, 19:163-196.

Figini, "In Vitro assembly of Repertoires of Antibody Chains on the Surface of Phage by Renaturation" (1994) *J. Mol. Biol.*, 239:68-78.

Fishwild et al., "High-avidity human IgG kappa monoclonal antibodies from a novel strain of minilocus transgenic mice" (1996) *Nature Biotechnology*, 14:845-851.

Fleisher B., Mechanism of glycosylation in the Golgi apparatus. J Histochem Cytochem, Aug. 1983; 31(8):1033-1040.

Folk et al., "Carboxypeptidase B, Purification and Characterization of the Porcine Enzyme," J. Biological Chem, 1960, 235:2272-2277.

Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.

Foote, J., "Antibody framework residues affecting the conformation of the hypervariable loops" (1992) *J. Mol .Biol.*, 224(2):487-499.

Freitag et al., "Displacement chromatography in biotechnological downstream processing," J. Chromatography, (1995) 691(1):101-112.

(56) References Cited

OTHER PUBLICATIONS

Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Goswami et al., "Developments and Challenges for mAb-Based Therapeutics," *Antibodies*, 2:452-500, 2013.
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Gramer M Jet al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Harding et al., "Class switching in human immunoglobulin transgenic mice" (1995) *Ann. NY Acad. Sci.*, 764:536-547.
Harlow and Lane, Antibodies A Laboratory Manual, Purification of Antibodies by using a; Deae-matrix (Batch), Storing and Purifying Antibodies; Chapter 8: 302-303 (1988).
Harlow et al., Eds ("Antibodies: A Laboratory Manual" 1988. Cold Spring Harbor Laboratory Press, Chapter 7, pp. 245, 247,and 253).
Harris, "Processing of C-terminal lysine and arginine residues of proteins isolated from mammalian cell culture" Journal of Chromatography, (1995) 705; 129-134.
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor -alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al., "Optimal and consistent protein glycosylation in mammalian cell culture", Glycobiology; (2009), 19(9):936-949.
Hossler et al.; "Improvement of mammalian cell culture performance through surfactant enabled concentrated feed media"; Biotechnology Progress; 29(4):1023-1033 (2013).
//www.cygnustechnologies.com/product_detail/host-cell-protein-antibodies/anti-cho-h . . . CYGNUS Technologies, Anti-CHO HCP (Apr. 18, 2012), 1 page.
Huang et al. "Effects of anti-TNF monoclonal antibody infusion in patients with hairy cell leukaemia" (1992) *Br. J. Haematol.*, 81(2):231-234.
Huang, L., et al., In Vivo Deamidation Characterization of Monoclonal Antibody by LC/MS/MS. Analytical Chemistry, 2005. 77(5): p. 1432-1439.
Humira (adalimumab) label, Revised Sep. 2013, 87 pages.
Humira (adalimumab) prescribing information, Dec. 20, 2002, pp. 1-16.

(56) References Cited

OTHER PUBLICATIONS

Huse, "Generation of a large combinatorial library of the immunoglobulin repertoire in phage lambda" (1989) *Science*, 246:1275-81.
HyClone™ CDM4CHO Catalog listing (last accessed Nov. 17, 2014).
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011, 5 pages.
International Preliminary Report on Patentability for Application No. PCT/US2011/060388, dated May 30, 2012, 9 pages.
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.

Jack, M.; Wright, D.; The Role of Advanced Glycation Endproducts and Glyoxalase I in Diabetic Peripheral Sensory Neuropathy; Transl. Res. 2012, 159, 355-365.
Jakobovits, A., "Production of fully human antibodies by transgenic mice" (1995) *Curr. Op. Biotechnol.*, 6:561-566.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jefferis, R., Glycosylation of Recombinant Antibody Therapeutics. Biotechnology Progress, 2005.21(1): p. 11-16.
Jespers, "Guiding the Selection of Human Antibodies from Phage Display Repertoires to a Single Epitope of an Antigen" (1994) *Bio/Technology*, 12:899-903.
Johnson et al., "Characterization of cathepsin L secreted by S/21 insect cells", Archives of Biochemistry and Biophysics (2005), 444:7-14.
Johnson, K.A., et al., Cation exchange HPLC and mass spectrometry reveal C-terminal amidation of an IgG1 heavy chain. Analytical Biochemistry, 2007. 360(1): p. 75-83.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "TNF-α antagonists beyond approved indications: stories of success and prospects for the future", Q J Med (2010) 103:917-928.
Kaschak et al: "Characterization of the basic charge variants of a human IgGI: Effect of copper concentration in cell culture media", MABS, vol. 3, No. 6, Nov. 1, 2011, pp. 577-583.
Kazuaki F et al "Enhancment of productivity of recombinant a-amidating enzyme by low temperature culture" Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I)144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009 (Mar. 6, 2009), pp. 639-648.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Kingkeohoi, S., Analysis of methylglyoxal metabolism in CHO celis grown in culture, Cytotechnology (2005) 48:1-13.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Kwon et al., "Production of lactic acid by *Lactobacillus rhamnosus* with vitamin-suppremented soybean hydrolysate", Enzyme Microb Technol. (2000), 26:209-215.

(56) References Cited

OTHER PUBLICATIONS

Lerner, "Antibodies without immunization" (1992) *Science*, 258:1313-1314.
Leusch, "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.
Li et al., "Cell Culture Processes for Monoclonal Antibody Production," mAbs, 2:5, 466-477, Sep./Oct. 2010.
Li, F. et al., "Current Therapeutic Antibody Production and Process Optimization" BioProcessing Journal, vol. 4(5):23-30 (2005).
Li, Feng, et al., "Cell Culture Processes for Monoclonal Antibody Production," mAbs 2:5, 466-479 (Sep.-Oct. 2010).
Lifely et al., "Glycosylation and Biological Activity of CAMPATH-1H Expressed in Different Cell Lines and Grown Under Different Culture Conditions", *Glycobiology*, 5(8):813-822 (1995).
Liu et al., "Recovery and purification process development for monoclonal antibody production," MABS (2010) 2(5):480-499.
Liu, H., et al., Heterogeneity of monoclonal antibodies. Journal of Pharmaceutical Sciences, 2008. 97(7): p. 2426-2447.
Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistry, 269, 32299-32305.
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low et al., "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007 (Aug. 18, 2007), pp. 15-29.
Luo et al., "Understanding of C-terminal lysine variants in antibody production using mammalian cells" Abstract of papers, ACS, Anaheim, CA, US, Mar. 2011, 1 page.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012 (Jul. 2012), pp. 1061-1068.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".
Manning, M., et al., *Stability of Protein Pharmaceuticals: An Update*. Pharmaceutical Research, 2010.27(4): p. 544-575.
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." in *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*Proteins: Structure, Function and Genetics*, 25:130-133.
Martinelle, K. et al., "Effect of different cell culture medium surfactants on cell growth and viability", Cells and Culture, Proceedings of the 20th ESACT Meeting v4 819-822, Jun. 17-20, 2007.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
McAtee et al., "Isolation of monoclonal antibody charge variants by displacement chromatography," Current Protocols in Protein Science, 8.10-8.10.13, 2012.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al., "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Mizuochi, T., et al., Structural and numerical variations of the carbohydrate moiety of immunoglobulin G. J Immunol, 1982. 129(5): p. 2016-20.
Moore, A., et al., "Effects of temperature shift on cell cycle, apoptosis and nucleotide pools in CHO cell batch cultures", Cytotechnology, 23:47-54, 1997.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Ni, W.; Analysis of Isoaspartic Acid by Selective Proteolysis with Asp-N and Electron Transfer Dissociation Mass Spectrometry; Anal. Chem. 2010, 82,7485-7491.
Nilsson, "Antibody engineering" (1995) *Current Opinion in Structural Biology*, 5:450-456.

(56) References Cited

OTHER PUBLICATIONS

Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Oh, D-K. et al., "Increased erythritol production in fed-batch cultures of *Torula* sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. Oct. 10, 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992 (Jan. 1, 1992), pp. 839-845.
PCT/US2013/069702 International Search Report & Written Opinion mailed Jan. 31, 2014, 13 pages.
Perchiacca et al., "Aggregation-resistance domain antibodies engineered with charged mutations; near the edges of the complementarity-determining regions," Protein Engineering Design & Selection, 25: 10 (591-601) 2012.
Perkins, M.; et. Al. Determination of the Origin of Charge Heterogeneity in a Murine Monoclonal Antibody; M. Pharm. Res. 2000, 17, 1110-1117.
Pietersz et al., "In vitro and in vivo Antitumor Activity of a Chimeric anti-CD19 Antibody", *Cancer Immunol. Immunother.*, 41:53-60 (1995).
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996 (Oct. 1, 1996), pp. 189-200.
Potter et al., "Antibody Production in the Baculovirus Expression System", *Intern. Rev. Immunol.*, 10:103-112 (1993).
Poul at al., "Design of Cassette Baculovirus Vectors for the Production of Therapeutic Antibodies in Insect Cells", *Immunotechnology*, 1:189-196 (1995).

Quan, C., et al., A study in glycation of a therapeutic recombinant humanized monoclonal antibody: Where it is, how it got there, and how it affects charge-based behavior. Analytical Biochemistry, 2008.373(2): p. 179-191.
Queen, C., "A humanized antibody that binds to the interleukin 2 receptor" (1989) *Proc. Natl. Acad. Sci. USA*, 86(24):10029-10033.
Rabbani, N.; Thornalley, P. J.; Glyoxalase in diabetes, obesity and related disorders; Semin. Cell Dev. Biol. 2011, 22, 309-317.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International.*, 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011 (Jan. 25, 2011), pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997 (Jan. 1, 1997), pp. 201-207.
Roy, B.M., et al., Toxic concentrations of exogenously supplied methy!glyoxal in hybridoma cell culture, Cytotechnology (2004) 46:97-107.
Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.
Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et aL, "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation

(56) References Cited

OTHER PUBLICATIONS

Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006 (Nov. 1, 2006), pp. 1161-1173.

Saxena, R. K. et al.; Microbial production and applications of 1 ,2-propanediol; Indian J. Microbiol. 2010,50,2-11.

Schiestl et al., "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995), 9 pages.

Senczuk et al., "Hydrophobic interaction chromatography in dual salt system increases protein binding capacity" Biotechnology and Bioengineering, 103(5), 930-935 (2009).

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shen, Amy Y. et al., "Recombinant DNA Technology and Cell Line Development," from "Cell Culture Technology for Pharmaceutical and Cell-Based Therapies," CRC Press, 1995, 15-40.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sigma Catalog "RPMI1640" (last accessed Jan. 22, 2015), 3 pages.

Sigma MSDS for RMPI1640 (last accessed Jan. 22, 2015), 6 pages.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sundaram et al., "An innovative approach for the characterization of the isoforms of a monoclonal antibody product," Mabs, 3(6):505-512, 2011.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al., "Expression and purification of a secreted functional mouse/human chimaeric antibody against bacterial endotoxin in baculovirus-infected insect cells", Biotechnol. Appl. Biochem. (1999), 30:59-64.

Taylor et al.,"Human immunoglobulin transgenes undergo rearrangement, somatic mutation and class switching in mice that lack endogenous IgM" (1994) *Int. Immunol.*, 6:579-591.

Teichmann, S. Declaration dated Dec. 17, 2010 from opposition proceedings in EP 0929578, 6 pages.

Tess database "HYCLONE" Trademark #76244963. Filing date Apr. 23, 2001. Live mark. Last accessed Jan. 21, 2015.

Tess database "HYCLONE" Trademark #85769283. Filing date Sep. 30, 2012. Live mark. Last accessed Jan. 21, 2015.

Tharmalingam et al.; "Pluronic Enhances the Robustness and Reduces the Cell Attachment of Mammalian Cells"; Molecular Biotechnology; 39(2):167-177 (2008).

The Kennedy Institute of Rheumatology, 1995 Annual Scientific Report, "Anti-TNF trials and studies of mechanisms of action".

The MW Calculator available at the Sequence Manipulation Suite (see <//bioinformatics.org/sms2/index.html), downloaded Feb. 25, 2014, 2 pages.

The pI Calculator available at the Sequence Manipulation Suite (see <//bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from http://www.ama-assn.org/resources/doc/usan/adalimumab.doc. 1 page.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

United States Food and Drug Administration (FDA) Biological Licensing Application File No. 125057 (Adalimumab) (Dec. 31, 2002) (Last Accessed Mar. 4, 2015 at <//www.fda.gov/Drugs/DevelopmentApprovalProcess/HowDrugsareDevelopedandApproved/ApprovalApplications/TherapeuticBiologicApplications/ucm080610.htm>), 1 page.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.

Van Lent PL, et al., "The impact of protein size and charge on its retention in articular cartilage" J Rheumatol. Aug. 1987;14(4):798-805.

Varasteh et al., Optimization of Anti-Rh D Immunoglobulin Stability in the Lyphiiization Process. Iranian Journal of Basic Medical Sciences, Spring 2008, vol. 11, No. 1. pp. 55-61.

(56) References Cited

OTHER PUBLICATIONS

Vasilli, P. et al., The Pathophysiology of Tumor Necrosis Factors, Annu. Rev. Immunol. 10:411-452 (1992).
Vaughan, "Human antibodies by design" (1998) *Nature Biotechnology*, 16:535-539.
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Wagner et al., "Antibodies generated from human immunoglobulin miniloci in transgenic mice" (1994) *Nucl. Acids Res*. 22:1389-1393.
Wagner et al., "The diversity of antigen-specific monoclonal antibodies from transgenic mice bearing human immunoglobulin gene miniloci" (1994) *Eur. J. Immunol.*, 24:2672-2681.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Ward, "Binding activities of a repertoire of single immunoglobulin variable domains secreted from *Escherichia coli*" (1989) *Nature*, 341:544-546.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Wedemayer et al., "Structural insights into the evolution of an antibody combining site" (1997) *Science*, 276:1665-1669.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Williams, A. et al., Ion-Exchange Chromatography, Oct. 1998, Supplement 44, pp. 10-10-1-10-10-30.
Winter, "Humanized antibodies" (1993) *Immunol. Today*, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yigzaw et al., "Exploitation of the adsorptive properties of depth filters for host cell protein removal during monoclonal antibody purification," Biotechnol Progress, (2006) 22(1):288-296.
Yuk, I.H. et al., Controlling Glycation of Recombinant Antibody in Fed Batch Cell Cultures, Nov. 2011, Biotechnoloqy and Bioenqineerinq, vol. 108, No. 11 pp. 2600-2610.
Yumioka et al., "Screening of effective column rinse solvent for Protein-A chromatography," Protein Expression and Purification, (2010) 70(2): 218-223.
Zang, T.; et al.; Chemical Methods for the Detection of Protein N-Homocysteinylation via Selective Reactions with Aldehydes; Anal. Chem. 2009, 81, 9065-9071.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Zou et al., "Dominant expression of a 1.3 Mb human Ig kappa locus replacing mouse light chain production" (1996) *FASEB J.*, 10:1227-1232.
Babcock, James et al., "Partial Replacement of Chemically Defined Media with Plant-Derived Protein Hydrolysates," *BioPharm International*, vol. 23: 6. Jun. 2010, 6 pages.
Bandyopadhyay S., et al. Physicochemical and functional characterization of a biosimilar adalimumab ZRC-3197, Biosimilars, 2015;5, pp. 1-18.
Brock, Jonathan et al., "Detection and identification of arginine modifications on methylglyoxal-modified ribonuclease by mass spectrometric analysis," Journal of Mass Spectrometry, 2007; 42: 89-100.
Dionex Application Note 125 (Monitoring Protein Deamidation by Cation-Exchange Chromatography. 2009; pp. 1-7).
Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.
Extended European Search Report for Application No. 13877986.3. Dated Aug. 4, 2014, 11 pages.
Fahrner et al., "Industrial purification of pharmaceutical antibodies: development, operation, and validation of chromatography processes" Biotechnology and Genetic Engineering Reviews, 18, 2001, pp. 301-327.
Gagnon, P., "Polishing methods for monoclonal IgG purification" Chapter 17, Taylor & Francis Group, LLC, pp. 491-505, 2007.
Gao et al. "Site-selective modifications of arginine residues in human hemoglobin induced by methylglyoxal." Biochemistry, 2006; pp. 15654-15660.
Goochee, C.F. "Bioprocess Factors Affecting Glycoprotein Oligosaccharide Structure." *Develop. Biol. Standard*, vol. 76 (1992). 95-104.
Grosvenor, Sally, "A New Era in Cell Culture Media Development," *BioPharm International*, Jul. 2012 vol. 25: 7, 7 pages.
Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.
Indian Patent Office—IPAIRS application status for 2285/MUM/2013—Application not yet published. Document found on internet at ipindiaonline.gov/in/patentsearch/search/index.aspx. Last accessed Apr. 13, 2015.
International Preliminary Report on Patentability for Application No. PCT/US2013/031365, dated Mar. 3, 2015, 9 pages.
International Preliminary Report on Patentability for Application No. PCT/US2013/031380, dated Sep. 15, 2015, 13 pages.
International Preliminary Report on Patentability for Application No. PCT/US2013/065720, dated Sep. 24, 2015, 8 pages.
International Preliminary Report on Patentability for Application No. PCT/US2013/065749 dated Sep. 15, 2015, 10 pages.
International Preliminary Report on Patentability for Application No. PCT/US2013/065797, dated Sep. 24, 2015, 8 pages.
International Preliminary Report on Patentability for Application No. PCT/US2013/069702, dated Sep. 15, 2015, 8 pages.

(56) References Cited

OTHER PUBLICATIONS

International Preliminary Report on Patentability for Application No. PCT/US2014/024151, dated Sep. 15, 2015, 9 pages.
International Preliminary Report on Patentability for Application No. PCT/US2014/024256, dated Sep. 15, 2015, pp. 1-9.
International Preliminary Report on Patentability for Application No. PCT/US2014/026606, dated Sep. 15, 2015, 13 pages.
International Preliminary Report on Patentability for Application No. PCT/US2014/026636, dated Sep. 15, 2015, 9 pages.
International Search Report and Written Opinion from PCT/US2015/039773 dated Sep. 25, 2015, pp. 1-14.
International Search Report for Application No. PCT/US2015/038819 Dated Sep. 2, 2015, 12 pages.
Liu et al. "Recovery and purificaiton process development for monoclonal antibody production" MABS, 2(5), pp. 480-499 (2010).
Mehta, et al. "Purifying therapeutic monoclonal antibodies," Chemical Engineering Progress; May 2008, 104, 5; pp. S14-20.
Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.
Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.
Roe, S. "Separation Based on Structure" Chapter 4, § 5.2, In, Protein Purification Methods; A Practical Approach, Harries, et al. Sep. 1989, p. 203.
Roy, Samar N. et al., "Secretion of Biologically Active Recombinant Fibrinogen by Yeast." The Journal of Biological Chemistry, vol. 270; 40 (1995). 23761-23767.
Sargent (pp. 1-3, Internet Archive captured Aug. 28, 2013, www.cellculturedish.com/2012/01 /cho-cells-the-top-expressionsystem-of-best-selling-biologic-drugs/).
Scientific Discussion. Retrieved from the Internet: www.ema.europa.eu/dics/en_GB/document_library/EPAR Sceintific_Discussion/human/00481/WC500050867.pdf [retrieved on Jun. 29, 2015], EMEA, 2004, 25 pages.
Seo, Jin Seok, et al., "Effect of culture pH on recombinant antibody production by a new human cell line, F2N78, grown in suspension at 33.0 ° C. and 37.0° C.," Appl. Microbiol Biotechnol., vol. 97 (2013). 5283-5291.
Shirato, Ken et al., "Hypoxic regulation of glycosylation via the N-acetylglucosamine cycle." J. Clin. Biochem. Nutr. vol. 48; 1 (2011). 20-25.
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
Wang, Tina et al., "Exploring Post-translational Arginine Modification Using Chemically Synthesized Methylglyoxal Hydroimidazolones," J. Am. Chem. Soc., 2012, 134, pp. 8958-8967.
Zhang, Y. et al., "Specificity and Mechanism of Metal Ion Activation in UDP-galactose: β-Galactoside-α-1,3-galactosyltransferase." J. Biological Chemistry vol. 276; 15 (2001). 11567-11574.
"Preliminary Data From Two Clinical Trials Demonstrate Abbott Laboratories' HUMIRA Improved Symptoms of Psoriatic Arthritis and Ankylosing Spondylitis" PR Newswire (2004).
Abbott Laboratories Announces Positive Results of Phase II HUMIRA (R) (adalimumab) Study in Psoriasis, P.R. Newswire. (2004).
Alessandri, L. et al., "Increased serum clearance of oligomannose species present on a human IgG1 molecule." mAbs, (2012), 4(4); 509-520.
Amersham Biosciences, Antibody Purification Handbook (2002), pp. 1-112.
An, Zhiqiang editor, "Therapeutic Monoclonal Antibodies: From Bench to Clinic," 2009 edition, John Wiley & Sons, Hoboken, NJ, US, pp. 73-76, section 3.4.3.

Anumula et al., "Quantitative glycan profiling of normal human plasma derived immunoglobulin and its fragments Fab and FcO" (2012) J. Immunol. Methods, 382:167-176.
Arakawa et al., Biotechnology applications of amino acids in protein purification and formulations, Amino Acids, vol. 33, pp. 587-605 (2007).
Arend et al., "Inhibition of the production and effects of interleukins-1 and tumor necrosis factor a in rheumatoid arthritis" (1995) Arth. Rheum., 38(2):151-160.
Ashkenazi et al., "Immunoadhesins: An alternative to human monoclonal antibodies" (1995) Methods, 8(2): 104-115.
Avgerinos, HUMIRA manufacturing: challenges and the path taken, Extended Reports from the 3rd International Symposium on Downstream Processing of Genetically Engineered Antibodies and Related Molecules (Oct. 3-5, 2004).
Babcock et al., Partial Replacement of Chemically Defined CHO Media with Plant-Derived Protein Hydrolysates, in Proceedings of the 21st Annual Meeting of the European Society for Animal Cell Technology (ESACT), Dublin, Ireland, Jun. 7-10, 2009, pp. 295-298 (Springer Netherlands).
Barb et al., "Branch-specific sialylation of IgG-Fc glycans by ST6Gal-I" Biochemistry, (2009) 48:9705-9707.
Bartelds et al., "Development of antidrug antibodies against adalimumab and association with disease activity and treatment failure during long-term follow-up" (2011) JAMA, 305(14):1460-1468.
Baynes et al., Role of Arginine in the Stabilization of Proteins against Aggregation, Biochemistry, vol. 44, pp. 4919-4925 (2005).
Bertolini et al., Stimulation of bone resorption and inhibition of bone formation in vitro by human tumour necrosis factors, (1986) Nature 319:516-518.
Bibila & Robinson, In Pursuit of the Optimal Fed-Batch Process for Monoclonal Antibody Production, Biotechnol. Prog., 11:1-13 (1995).
Bird et al. "Single-chain antigen-binding proteins." Science. (1988) 242:423-426.
Borys et al., Ammonia Affects the Glycosylation Patterns of Recombinant Mouse Placental Lactogen-I by Chinese Hamster Ovary Cells in a pH-Dependent Manner, Biotechnology and Bioengineering, 43:505-514 (1994).
Braun (2002), Anti-tumor necrosis factor a therapy for ankylosing spondylitis: international experience, Ann. Rheum. Dis. 61(Suppl. III):iii51-iii60.
Butler, Animal cell cultures: recent achievements and perspectives in the production of biopharmaceuticals, Appl. Microbiol. Biotechnol., 68: 283-291 (2005).
Butler, Optimisation of the Cellular Metabolism of Glycosylation for Recombinant Proteins Produced by Mammalian Cell Systems, Cytotechnology, 50:57-76 (2006).
Carpenter et al., Rational Design of Stable Protein Formulations: Theory and Practice, 101 pages, (2002).
Champion et al., Defining Your Product Profile and Maintaining Control Over It, Part 2, BioProcess Technical, vol. 3, pp. 52-57 (Sep. 2005).
Chen et al., Effects of Elevated Ammonium on Glycosylation Gene Expression in CHO Cells, Metabolic Engineering, 8:123-132 (2006).
Chun et al., Usability of size-excluded fractions of soy protein hydrolysates for growth and viability of Chinese hamster ovary cells in protein-free suspension culture, Bioresource Technology, 98:1000-1005 (2007).
Clincke et al. "Effect of iron sources on the glycosylation macroheterogeneity of human recombinant IFN-γ produced by CHO cells during batch processes," BMC Proceedings (Nov. 22, 2011) 5(Suppl 8):PI14, pp. 1-2.
Clincke et al. "Characterization of metalloprotease and serine protease activities in batch CHO cell cultures: control of human recombinant IFN-γ proteolysis by addition of iron citrate," BMC Proceedings (Nov. 22, 2011) 5(Suppl 8):P115, pp. 1-3.
Clinical trial No. NCT00085644 "Human Anti-tumor Necrosis Factor (TNF) Monoclonal Antibody Adalimumab in Subjects With Active Ankylosing Spondylitis (ATLAS)" (2004).

(56) References Cited

OTHER PUBLICATIONS

Clinical trial No. NCT00235105 "Adalimumab in Early Axial Spondyloarthritis (Without Radiological Sacroiliitis): Placebo Controlled Phase Over 3 Months Followed by a 9 Months Open Extension Phase" (2005).
Coffman et al., *High-Throughput Screening of Chromatographic Separations: 1. Method Development and Column Modeling*, Biotechnology & Bioengineering, 100:605-618 (2008).
Commercially Available HUMIRA product, approved by the FDA in Dec. 2002 and available in Jan. 2003.
CPMP Policy Statement on DNA and Host Cell Proteins (HCP) Impurities, Routine Testing versus Validation Studies, EMEA, Jun. 10, 1997.
Cromwell, *Avastin: highlights from development*, Extended Reports from the 3rd International Symposium on Downstream Processing of Genetically Engineered Antibodies and Related Molecules (Oct. 3-5, 2004).
Cruz et al., *Process development of a recombinant antibody/interleukin-2 fusion protein expressed in protein-free medium by BHK cells*, Journal of Biotechnology, 96:169-183 (2002).
Cumming, *Glycosylation of recombinant protein therapeutics: control and functional implications*, Glycobiology, 1(2):115-130 (1991).
Das et al., "Delivery of rapamycin-loaded nanoparticle down regulates ICAM-1 expression and maintains an immunosuppressive profile in human CD34+ progenitor-derived dendritic cells" (2008) J Biomed Mater Res A., 85(4):983-92.
Davis et al., Recombinant Human Tumor Necrosis Factor Receptor (Etanercept) for Treating Ankylosing Spondylitis, Arthritis & Rheumatism 48:3230-3236 (2003).
Del Val et al., *Towards the Implementation of Quality by Design to the Production of Therapeutic Monoclonal Antibodies with Desired Glycosylation Patterns*, American Institute of Chemical Engineers, Biotechnol. Prog., 26(6):1505-1527 (2010).
Eason et al., "Inhibition of the effects of Tnf in renal allograft recipients using recombinant human dimeric tumor necrosis factor receptors" (1995) Transplantation, 59(2):300-305.
Ebersbach et al., "Affilin-novel binding molecules based on human gamma-B-crystallin, an all beta-sheet protein" (2007) J. Mol. Biol., 372 (1): 172-85.
Elliot et al., "Randomised double-blind comparison of chimeric monoclonal antibody to tumour necrosis factor alpha (cA2) versus placebo in rheumatoid arthritis" (1994) Lancet, 344(8930):1105-1110.
Endres, *Soy Protein Products Characteristics, Nutritional Aspects, and Utilization*, 2001 (AOCS Press, Champaign, Illinois).
Ertani et al., *Biostimulant activity of two protein hydrolyzates in the growth and nitrogen metabolism of maize seedlings*, J. Plant Nutr. Soil Sci., 000:1-8 (2009).
Espinosa-Gonzalez, *Hydrothermal treatment of oleaginous yeast for the recovery of free fatty acids for use in advanced biofuel production*, Journal of Biotechnology, 187:10-15 (2014).
Falconer et al., *Stabilization of a monoclonal antibody during purification and formulation by addition of basic amino acid excipients*, vol. 86, pp. 942-948 (2011).
Farnan et al., Multiproduct High-Resolution Monoclonal Antibody Charge Variant Separations by pH Gradient Ion-Exchange Chromatography, Analytical Chem., vol. 81, No. 21, pp. 8846-8857 (2009).
Fauchère et al., *Amino acid side chain parameters for correlation studies in biology and pharmacology*, Int. J. Peptide Res., vol. 32, pp. 269-278 (1988).
Fava et al., "Critical role of peripheral blood phagocytes and the involvement of complement in tumour necrosis factor enhancement of passive collagen-arthritis" (1993) Clin. Exp. Immunol., 94(2):261-266.
Felver et al., "Plasma tumor necrosis factor a predicts decreased long-term survival in severe alcoholic hepatitis" (1990) Alcohol. Clin. Exp. Res. 14(2):255-259.
Fernandes, "Demonstrating Comparability of Antibody Glycosylation during Biomanufacturing," European Biopharmaceutical Review. (2005) pp. 106-110.
Fietze et al., "Cytomegalovirus infection in transplant recipients the role of tumor necrosis factor" (1994) Transplantation, 58(6):675-680.
Follmam et al., Factorial screening of antibody purification processes using three chromatography steps without protein A, J. Chromatography A, vol. 1024, pp. 79-85 (2004).
Foong et al., *Anti-tumor necrosis factor-alpha-loaded microspheres as a prospective novel treatment for Crohn's disease fistulae*, Tissue Engineering, Part C: Methods, 16(5):855-64 (2010).
Franek et al., Plant Protein Hydrolysates: Preparation of Defined Peptide Fractions Promoting Growth and Production in Animal Cells Cultures, Biotech. Progress, 16:688-692 (2000).
FrieslandCampina Domo. *Product Data Sheet: Proyield Pea PCE80B*. Paramus, NJ: Aug. 2011.
FrieslandCampina Domo. *Product Data Sheet: Proyield Soy SE70M-UF*. Paramus, NJ: Apr. 2011.
FrieslandCampina Domo. *Product Data Sheet: Proyield Wheat WGE80M-UF*. Paramus, NJ: Apr. 2011.
FrieslandCampina Domo. *Product Information Sheet: CNE50M-UF*. Zwolfe, NL: Jun. 2010.
Gagnon et al., *Technology trends in antibody purification*, J. Chromatography A., vol. 1221, pp. 57-70 (available online Oct. 2011).
Gawlitzek et al., *Ammonium Alters N-Glycan Structures of Recombinant TNFR-IgG: Degradative Versus Biosynthetic Mechanisms*, Biotechnology and Bioengineering, 68(6):637-646 (2000).
Gawlitzek et al., *Identification of Cell Culture Conditions to Control N-Glycosylation Site-Occupancy of Recombinant Glycoproteins Expressed in CHO cells*, 103:1164-1175 (2009).
Gibbs, *Production and Characterization of Bioactive Peptides from Soy Fermented Foods and Their Hydrolysates*, Dissertation, McGill University, Montreal Quebec (1999).
Gilar et al., "Characterization of glycoprotein digests with hydrophilic interaction chromatography and mass spectrometry" (2011) Analytical Biochem., 417:80-88.
Giroir et al., "Inhibition of tumor necrosis factor prevents myocardial dysfunction during burn shock" (1994) Am. J. Physiol., 267(1 Pt 2):H118-24.
Goetze, A. et al., "High-mannose glycans on the Fc region of therapeutic IgG antibodies increase serum clearance in humans." *Glycobiology* (2011), 21(7); 949-959.
Gong et al., *Fed-Batch Culture Optimization of a Growth-Associated Hybridoma Cell Line in Chemically Defined Protein-Free Media*, Cytotechnology, 52:25-38 (2006).
Goochee et al., *Environmental Effects on Protein Glycosylation*, Biotechnology, 8:421-427 (1990).
Gorfien et al., *Optimized Nutrient Additives for Fed-Batch Cultures*, BioPharm International, 16:34-40 (2003).
Grabulovski et al., "A Novel, Non-immunogenic Fyn SH3-derived Binding Protein with Tumor Vascular Targeting Properties" (2007) J Biol Chem 282, (5): 3196-3204.
Gramer et al. "Modulation of antibody galactosylation through feeding of uridine, manganese chloride, and galactose," Biotechnology and Bioengineering. (Jul. 1, 2011) 108(7):1591-1602.
Gross et al. "Involvement of various organs in the initial plasma clearance of differently glycosylated rat liver secretory proteins," Eur. J. Biochem. (1988) 173(3):653-659.
Gu et al., *Influence of Primatone RL Supplementation on Sialylation of Recombinant Human Interferon-γ Produced by Chinese Hamster Ovary Cell Culture Using Serum-Free Media*, Biotechnology and Bioengineering, 56(4):353-360 (1997).
Guidance for Industry—Q6B Specifications: Test Procedures and Acceptance Criteria for Biotechnological / Biological Products, Aug. 1999.
Guile et al., "A rapid high-resolution high-performance liquid chromatographic method for separating glycan mixtures and analyzing oligosaccharide profiles" (1996) Anal Biochem., 240(2):210-26.
Guse et al., *Purification and analytical characterization of an anti-CD4 monoclonal antibody for human therapy*, J. of Chromatography A, 661:13-23 (1994).

(56) References Cited

OTHER PUBLICATIONS

Haddadi et al., "Delivery of rapamycin by PLGA nanoparticles enhances its suppressive activity on dendritic cells" (2008) J Biomed Mater Res A., 84A(4):885-98.
Haibel (2005) *Arthritis and Rheumatism* 64(Suppl. III):316.
Haibel et al. (2004) *Arthritis and Rheumatism* 50(9):5217-18.
Hansen et al., "The role of tumor necrosis factor-alpha in acute endotoxin-induced hepatotoxicity in ethanol-fed rats" (1994) Hepatology, 20(2):461-474.
Hansen et al., *Extra- and intracellular amino acid concentrations in continuous Chinese hamster ovary cell culture*, Appl. Microbiol. Biotechnol., 41:560-564 (1994).
Harris et al., *Current Trends in Monoclonal Antibody Development and Manufacturing*, Chapter 12, pp. 193-205 (2010).
Hayter et al, *Chinese hamster ovary cell growth and interferon production kinetics in stirred batch culture*, Applied Microbiol. Biotech., 34:559-564 (1991).
Heeneman et al., *The concentrations of glutamine and ammonia in commercially available cell culture media*, J. Immunological Methods, 166:85-91(1993).
Hober, et al. "Protein A chromatography for antibody purification", J. Chromatography B, vol. 848 (2007) pp. 40-47.
Hong et al., *Substitution of glutamine by glutamate enhances production and galactosylation of recombinant IgG in Chinese hamster ovary cells*, Applied Microbiol. Biotech., 88:869-876 (2010).
Huang et al., *Nitrogen metabolism of asparagine and glutamate in Vero cells studied by 1H/15N NMR spectroscopy*, Applied Microbiol. Biotech., 77:427-436 (2007).
Hussain et al., "Hepatic expression of tumour necrosis factor-alpha in chronic hepatitis B virus infection" (1994) J. Clin. Pathol., 47:1112-1115.
Huston et al. "Protein engineering of antibody binding sites: recovery of specific activity in an anti-digoxin single-chain Fv analogue produced in *Escherichia coli*," Proc. Natl. Acad. Sci. USA(1988) 85:5879-5883.
International Conference on Harmonisation of Technical Requirements for Registration of Pharmaceuticals for Human Use, Specifications: *Test Procedures and Acceptance Criteria for Biotechnological / Biological Products Q6B*, Mar. 10, 1999.
International Preliminary Report on Patentability for Application No. PCT/US2014/059127, dated Apr. 14, 2016, 15 pages.
International Preliminary Report on Patentability for Application No. PCT/US2014/065793, dated May 17, 2016, 13 pages.
International Search Report and Written Opinion for Application No. PCT/US2014/058991, completed Dec. 18, 2014, 15 pages.
International Search Report and Written Opinion for Application No. PCT/US2014/065793, dated Jul. 27,2015, 20 pages.
International Search Report and Written Opinion from PCT/US2015/042846 dated Feb. 2, 2016, pp. 1-22.
International Search Report with Written Opinion corresponding to International Patent Application No. PCT/US2014/059127, mailed May 7, 2015, 21 pages.
Invitation to Pay Additional Fees for International Application No. PCT/US2014/058991, mailed Jan. 15, 2015, 6 pages.
Invitation to Pay Additional Fees for International Application No. PCT/US2014/059127, dated Jan. 15, 2015, 6 pages.
Invitation to Pay Additional Fees for International Application No. PCT/US2014/065793, dated May 4, 2015, 15 pages.
Jacob et al., Scale-up of Antibody Purification, Antibodies, vol. 1: Production & Purification, (2004).
Karnoup et al., *O-Linked glycosylation in maize-expressed human IgA1*, Glycobiology, 15(10):965-981 (2005).
Kaufman et al., "Amplification and expression of sequences cotransfected with a modular dihydrofolate reductase complementary dna gene" (1982) Mol. Biol., 159(4):601-621.
Kaufman et al., *Depletion of manganese within the secretory pathway inhibits O-linked glycosylation in mammalian cells*, Biochemistry, 33(33):9813-9 (1994).

Kelley et al., *Downstream Processing of Monoclonal Antibodies: Current Practices and Future Opportunities*, Process Scale Purification of Antibodies (2009).
Kim et al., *Glycosylation pattern of humanized IgG-like bispecific antibody produced by recombinant CHO cells*, Applied Microbiol. Biotech., 85:535-542 (2010).
Kipriyanov et al. "Recombinant single-chain Fv fragments carrying C-terminal cysteine residues: production of bivalent and biotinylated miniantibodies," Molecular Immunology, (1994) 31(14):1047-1058 F.
Kipriyanov et al., "Single-chain antibody streptavidin fusions: tetrameric bifunctional scFv-complexes with biotin binding activity and enhanced affinity to antigen," Human Antibodies and Hybridomas.(1995) 6(3):93-101.
Kobak, Osteonecrosis and monoarticular rheumatoid arthritis treated with intra-articular adalimumab, *S. Mod Rheumatol*, 18, 290-292, Feb. 20, 2008.
Koide et al., "Monobodies: antibody mimics based on the scaffold of the fibronectin type III domain" (2007), Methods Mol. Biol., 352: 95-109.
Konig et al., "Tumor necrosis factor α and interleukin-1 stimulate bone resorption in vivo as measured by urinary [3H] tetracycline excretion from prelabeled mice" (1988) J. Bone Miner. Res., 3(6):621-627.
Kramarczyk et al., *High-Throughput Screening of Chromatographic Separations: II. Hydrophobic Interaction*, 100: 708-720 (2008).
Krehenbrink et al., "Artificial Binding Proteins (Affitins) as Probes for Conformational Changes in Secretin PulD" (2008) J. Mol. Biol., 383 (5): 1058-68.
Kunkel et al., "Comparisons of the Glycosylation of a Monoclonal Antibody Produced under Nominally Identical Cell Culture Conditions in Two Different Bioreactors" (2000) Biotechnol. Prog., 16(3): 462-470.
Kunkel, Jeremy P., et al., "Dissolved oxygen concentration in serum-free continuous culture affects N-linked glycosylation of a monoclonal antibody," *Journal of Biotechnology*, 62 (1998), 55-71.
Kurano et al., *Growth behavior of Chinese hamster ovary cells in a compact loop bioreactor. 2. Effects of medium components and waste products*, J. Biotechnol., 15(1-2):113-128 (1990).
Lain et al., *Development of a High-Capacity MAb Capture Step Based on Cation-Exchange Chromatography*, BioProcess Int'l, vol. 7, pp. 26-34 (May 2009).
Lazar et al., *Matrix-assisted laser desorption/ionization mass spectrometry for the evaluation of the C-terminal lysine distributon of a recombinant monoclonal antibody*, Rapid Communications in Mass Spectrometry, vol. 18, pp. 239-244 (2004).
Leader et al., *Agalactosyl IgG in Aggregates from the Rheumatoid Joint*, Br. J. Rheumatol., 35:335-341 (1996).
Leavitt et al. "Impaired Intracellular Migration and Altered Solubility of Nonglycosylated Glycoproteins of Vesicular Stomatitis Virus and Sindbis Virus," J. Biol. Chem. (1977) 252(24):9018-9023.
Lerner et al., "Tumor necrosis factors α and β can stimulate bone resorption in cultured mouse calvariae by a Prostaglandin-independent mechanism" (1993) J. Bone Miner. Res., 8(2):147-155.
Lienqueo et al., *Mathematical correlations for predicating protein retention times in hydrophobic interaction chromatography*, 978:71-79 (2002).
Ling et al., *Analysis of Monoclonal Antibody Charge Heterogeneity Using Ion-Exchange Chromatography on a Fully Biocompatible HPLC System*, Dionex (2009).
Liu et al., "The significance of changes in serum tumour necrosis factor (TNF) activity in severely burned patients" (1994) Burns, 20(1):40-44.
Lobo-Alfonso et al., *Benefits and Limitations of Protein Hydrolysates as Components of Serum-Free Media for Animal Cell Culture Applications, Protein Hydrolysates in Serum Free Media*, GIBCO Cell Culture, Invitrogen Corporation, Grand Island, New York, Chapter 4:55-78 (2010).
Lowe et al. "A Genetic Approach to Mammalian Glycan Function," Annu. Rev. Biochem. (2003) 72:643-691.
Lu et al., *Recent Advancement in Application of Hydrophobic Interaction Chromatography for Aggregate Removal in Industrial Purification Process*, 10:427-433 (2009).

(56) References Cited

OTHER PUBLICATIONS

Lubinieki et al., *Comparability assessments of process and product changes made during development of two different monoclonal antibodies*, Biologicals, vol. 39, pp. 9-22 (2011).

Luksa et al., *Purification of human tumor necrosis factor by membrane chromatography*, J. Chromatography A, 661:161-168 (1994).

Lund et al., *Control of IgG/Fc Glycosylation: A Comparison of Oligosaccharides from Chimeric Human/Mouse and Mouse Subclass Immunoglobulin Gs*, Molecular Immunology, 30(8):741748 (1993).

MacDonald et al., "Tumour necrosis factor-alpha and interferon-gamma production measured at the single cell level in normal and inflamed human intestine" (1990) Clin. Exp. Immunol, 81(2):301-305.

Matsumoto et al., *Autoantibody Activity of IgG Rheumatoid Factor Increases with Decreasing Levels of Galactosylation and Sialylation*, J. Biochemistry, 128:621-628 (2000).

McCauley et al., "Altered cytokine production in black patients with keloids" (1992) J. Clin. Immunol., 12(4):300-308.

McClain et al., "Increased tumor necrosis factor production by monocytes in alcoholic hepatitis" (1989) Hepatology, 9(3):349-351.

McCue et al., *Effect of phenyl sepharose ligand density on protein monomer/aggregate purification and separation using hydrophobic interaction chromatography*, J. of Chromatography A, 1216:209-909 (2009).

McLeod, "Adalimumab, etanercept and infliximab for the treatment of ankylosing spondylitis: a systematic review and economic evaluation," Health Technol. Assess. 11(28):1-158 (2006).

Meert et al., *Characterization of Antibody Charge Heterogeneity Resolved by Preparative Immobilized pH Gradients*, Analytical Chem., vol. 82, pp. 3510-3518 (2010).

Melter et al., *Adsorption of monoclonal antibody variants on analytical cation-exchange resin*, J. Chromatography A, vol. 1154, pp. 121-131 (2007).

Millward et al. "Effect of constant and variable domain glycosylation on pharmacokinetics of therapeutic antibodies in mice," Biologicals.(2008) 36(1):41-47.

Mizrahi, *Primatone RL in mammalian cell culture media*, Biotechnol. Bioeng., 19:1557-1561 (1977).

Moller et al., "Monoclonal antibodies to human tumor necrosis factor α: In vitro and in vivo application" (1990) Cytokine 2(3):162-169.

Moloney and Haltiwanger, *The O-linked fucose glycosylation pathway: indentification and characterization of a uridien diphosphoglucose: fucose-β1,3-glucosyltransferase activity from Chinese hamster ovary cells*, Glycobiology, 9:679-87 (1999).

Morgan et al. "Designing Biobetter Monoclonal Antibody Therapeutics by Glycoengineering," International Pharmaceutical Industry. (2011) pp. 38-44.

Nixon et al., "Engineered protein inhibitors of proteases" (2006) Curr Opin Drug Discov Devel, 9(2): 261-8.

Nyberg et al., *Metabolic Effects on Recombinant Interferon-γ Glycosylation in Continuous Culture of Chinese Hamster Ovary Cells*, Biotech. Bioeng., 62(3):336-347 (1999).

Nygren et al., "Alternative binding proteins: affibody binding proteins developed from a small three-helix bundle scaffold" (2008) FEBS J., 275 (11): 2668-76.

Onda et al., *Reduction of the Nonspecific Animal Toxicity of Anti-Tac (Fv)-PE38 by Mutations in the Framework Regions of the Fv Which Lower the Isoelectric Point*, J. Immunology, vol. 163, pp. 6072-6077 (1999).

Pacesetter, Beckman Coulter Newsletter, vol. 3, Issue 1 (Apr. 1999).

Packer et al., "A general approach to desalting oligosaccharides released from glycoproteins" (1998) Glycoconj J., 15(8):737-47.

Proteus, "Protein A Antibody Purification Handbook," Pro-Chem Inc., 2005, pp. 1-52.

Raju et al. "Galactosylation variations in marketed therapeutic antibodies," MABS. (May 1, 2012) 4(3):385-391.

Raju et al., "Glycoengineering of Therapeutic Glycoproteins: In Vitro Galactosylation and Sialylation of Glycoproteins with Terminal N-Acetylglucosamine and Galactose Residues" (2001) Biochemistry, 40(30):8868-8876.

Raju, *Terminal sugars of Fc glycans influence antibody effector functions of IgGs*, Current Opinion in Immunology, 20:471-478 (2008).

Rankin et al., "The therapeutic effects of an engineered human anti-tumour necrosis factor alpha antibody(CDP571) in rheumatoid arthritis" (1995) Br. J. Rheumatol., 34:334-342.

Rao et al., *mAb Heterogeneity Characterization: MabPac Strong Cation-Exchanger Columns Designed to Extend Capabilities of mAb Analysis*, Tutorials (Mar. 15, 2011).

Rao et al., *Separation of Monoclonal Antibodies by Weak Cation-Exchange Chromatography Using ProPac and ProSwift Columns*, Dionex (available online 2010).

Remy et al., " Zinc-finger nucleases: A powerful tool for genetic engineering of animals" (2010) Transgenic Res., 19(3): 363-71.

Restelli, Veronica, et al., "The Effect of Dissolved Oxygen on the Production and the Glycosylation Profile of Recombinant Human Erythropoietin Produced From CHO Cells," Biotechnology and Bioengineering, vol. 94, No. 3, (2006) 481-494.

Rivinoja et al, *Elevated Golgi pH Impairs Terminal NL Glycosylation by Inducing Mislocalization of Golgi Glycosyltransferases*, J. Cell. Physiol., 220:144-154 (2009).

Robinson et al., *Characterization of a Recombinant Antibody Produced in the Course of a High Yield Fed-Batch Process*, Biotech. Bioeng., 44:727-735 (1994).

Rodriguez et al., *Enhanced Production of Monomeric Interferon-â by CHO Cells through the Control of Culture Conditions*, Biotechnol. Prog., 21:22-30 (2005).

Rosolem et al., *Manganese uptake and redistribution in soybean as affected by glyphosate*, Rev. Bras. Ciênc. Solo, 34:1915-1922 (2010).

Rouiller et al. "Effect of hydrocortisone on the production and glycosylation of an Fc-Fusion protein in CHO cell cultures," Biotechnology Progress.(May 2012) 28(3):803-813.

Rudd et al. "Glycosylation and the Immune System," Science. (2001) 291(5512):2370-2376.

Rudwaleit et al., Adalimumab is effective and well tolerated in treating patients with ankylosing spondylitis who have advanced spinal fusion, *Rhematology*; 48; 551-557 (2009).

Russell et al., "Targets for sepsis therapies: Tumor necrosis factor versus interleukin-1" (1993) Curr. Opin. Biotech., 4:714-721.

Santiago et al., "Targeted gene knockout in mammalian cells by using engineered zinc-finger nucleases" (2008) Proc. Natl. Acad. Sci. USA., 105(15):5809-14.

Santora et al., *Determination of Recombinant Monoclonal Antibodies and Noncovalent Antigen TNFα Trimer Using Q-TOF Mass Spectrometry*, Spectroscopy, 17(5):50-57 (2002).

Scales et al., "Hepatic ischemia/reperfusion injury: importance of oxidant/tumor necrosis factor interactions" (1994) Am. J. Physiol., 267 (6 Pt 1):G1122-1127.

Schenerman et al., *CMC Strategy Forum Report*, BioProcess Technical (2004).

Schlaeger E.-J., *The protein hydrolysate, Primatone RL, is a cost-effective multiple growth promoter of mammalian cell culture in serum-containing and serum-free media and displays anti-apoptosis properties*, J. Immunol. Meth., 194:191-199 (1996).

Serrick et al., "The early release of interleukin-2, tumor necrosis factor-alpha and interferon-gamma after ischemia reperfusion injury in the lung allograft" (1994) Transplantation, 58(11):1158-1162.

Shankar et al., " Evaluation of the role of second messenger systems in tumor necrosis factor-stimulated resorption of fetal rat limb bones" (1993) Bone, 14(6):871-876.

Sheffield Bioscience, Bio-Science Technical Manual: Supplements for cell culture, fermentation, and diagnostic media, 43 pages (2011).

Shen et al., *Characterization of yeastolate fractions that promote insect cell growth and recombinant protein production*, Cytotechnology, 54:25-34 (2007).

(56) References Cited

OTHER PUBLICATIONS

Sheron et al., "Increased production of tumour necrosis factor alpha in chronic hepatitis B virus infection" (1991) J. Hepatol., 12(2):241-245.
Shi et al., *Real Time Quantitative PCR as a Method to Evaluate Xenotropic Murine Leukemia Virus Removal During Pharmaceutical Protein Purification*, Biotechnology & Bioengineering, vol. 87, No. 7, pp. 884-896 (Sep. 2004).
Shibuya et al., "The elderberry (*Sambucus nigra* L.) bark lectin recognizes the Neu5Ac(alpha 2-6)Gal/GalNAc sequence"(1987) J. Biol. Chem., 262(4): 1596-1601.
Shields et al. "Lack of Fucose on Human IgGI N-Linked Oligosaccharide Improves Binding to Human FcyRIII and Antibody-dependent Cellular Toxicity," J. Biol. Chem. (2002) 277(30) :26733-26740.
Shim, H., "One target, different effects: a comparison of distinct therapeutic antibodies against the same targets." Experimental and Molecular Medicine, vol. 43, p. 539-549, Oct. 2011.
Shukla et al., *Downstream processing of monoclonal antibodies—Application of platform approaches*, J. of Chromatography B, 848:28-39 (2007).
Shukla et al., eds., *Process Scale Bioseparations for the Biopharmaceutical Industry*, (Taylor & Francis Group, Boca Raton FL) (2006).
Shukla et al., *Recent advances in large-scale production of monoclonal antibodies and related proteins*, Trends in Biotechnology, 28(5):253-261 (2010).
Shukla et al., *Strategies to Address Aggregation During Protein a Chromatography*, BioProcess International, 3:36-44 (2005).
Siemensma et al., Towards an Understanding of How Protein Hydrolysates Stimulate More Efficient Biosynthesis in Cultured Cells: *Protein Hydrolysates in Biotechnology,Bio-Science*, 36 pages (2010).
Silverman et al., "Multivalent avimer proteins evolved by exon shuffling of a family of human receptor domains" (2005) Nat. Biotechnol., 23 (12): 1556-61.
Skerra et al., "Alternative binding proteins: Anticalins—harnessing the structural plasticity of the lipocalin ligand pocket to engineer novel binding activities kerra" (2008) FEBS J., 275 (11): 2677-83.
Stumpp et al., "DARPins: A new generation of protein therapeutics" (2008) Drug Discov. Today, 13 (15-16): 695-701.
Sun et al., "Bowel necrosis induced by tumor necrosis factor in rats is mediated by platelet-activating factor" (1988) J. Clin. Invest., 81(5):1328-1331.
Suthanthiran et al., "Renal transplantation" (1994) New Engl. J. Med., 331(6):365-376.
Takashima et al., "Characterization of Mouse Sialyltransferase Genes: Their Evolution and Diversity" (2008) Biosci. Biotechnol. Biochem., 72(5):1155-1167.
Tang et al., *Conformational characterization of the charge variants of a human IgG1 monoclonal antibody using H/D exchange mass spectrometry*, mAbs, vol. 5, pp. 114-125 (2013).
Taylor et al. "A transgenic mouse that expresses a diversity of human sequence heavy and light chain immunoglobulins," Nucleic Acids Research,(1992) 20(23):6287-6295.
Tebbey, Paul W., et al., "Consistency of quality for the glycosylated monoclonal antibody Humira (adalimumab)," MAbs, Sep. 3, 2015;7(5); 805-11.
The Difference-Between, "Poly vs. Polyalcohol- What's the difference?" pp. 1-2, downloaded from http://the-difference-between.com/polyalcohol/polyol on Apr. 16, 2016.
Thiansilakul et al., *Compositions, functional properties and antioxidative activity of protein hydrolysates prepared from round scad (Decapterus maruadsi)*, Food Chemistry, 103:1385-1394 (2007).
Tian et al., *Spectroscopic evaluation of the stabilization of humanized monoclonal antibodies in amino acid formulations*, Int'l J. of Pharmaceutics, vol. 335, pp. 20-31 (2007).

To , et al., Hydrophobic interaction chromatography of proteins: I. The effects of protein and adsorbent properties on retention and recovery, J. of Chromatography A, 1141:191-205 (2007).
Tracey et al., "Shock and tissue injury induced by recombinant human cachectin" (1986) Science, 234(4775):470-474.
Tritsch et al., *Spontaneous decomposition of glutamine in cell culture media*, Experimental Cell Research, 28:360-364 (1962).
Tsubaki et al., *C-terminal modification of monoclonal antibody drugs: Amidated species as a general product0related substance*, Int'l J. Biological Macromolecules, vol. 52, pp. 139-147 (2013).
Tugcu et al., *Maximizing Productivity of Chromatography Steps for Purification of Monoclonal Antibodies*, vol. 99, No. 3, pp. 599-613 (available online Aug. 2007).
Urech, D.M. et al., Anti-inflammatory and cartilage-protecting effects of an intra-articularly injected anti-TNFa single-chain Fv antibody (ESBA105) designed for local therapeutic use, Ann Rheum Dis, 69, 443-449, Mar. 16, 2009.
Urlaub et al., "Isolation of Chinese hamster cell mutants deficient in dihydrofolate reductase activity" (1980) Proc. Natl. Acad. Sci. USA, 77:4216-4220.
Van der Heijde et al., Adalimumab effectively reduces the signs and symptoms of active ankylosing spondylitis in patients with total spinal ankylosis, Arthritis & Rheumatism 67:1218-1221 (2008).
Van der Heijde et al., Efficacy and Safety of Adalimumab in Patients with Ankylosing Spondylitis, Arthritis & Rheumatism 54:2136-46 (2006).
Van der Heijde et al., Efficacy and Safety of Infliximab in Patients with Ankylosing Spondylitis, Arthritis & Rheumatism 52:582-591 (2005).
Van Der Poll et al., "Activation of coagulation after administration of tumor necrosis factor to normal subjects" (1990) N. Engl. J. Med., 322(23):1622-1627.
Van Der Poll et al., "Comparison of the early dynamics of coagulation activation after injection of endotoxin and tumor necrosis factor in healthy humans" (1991) Prog. Clin. Biol. Res., 367:55-60.
Van Dulleman et al., "Treatment of Crohn's disease with anti-tumor necrosis factor chimeric monoclonal antibody (cA2)" (1995) Gastroenterology, 109(1):129-135.
Varki et al. Essentials of Glycobiology, 2nd edition, (1999) CSHL, Retrieved from the internet: ncbi.nlm.nih.gov/books/NBK1908/, 4 pages.
Wallick et al. "Glycosylation of a VH residue of a monoclonal antibody against alpha (1—6) dextran increases its affinity for antigen," J. Exp. Med.(1988) 168(3):1099-1109.
Walsh et al. "Effect of the carbohydrate moiety on the secondary structure of ?2-glycoprotein. I. Implications for the biosynthesis and folding of glycoproteins," Biochemistry. (1990) 29(26):6250-6257.
Wang et al., "The immobilized leukoagglutinin from the seeds of Maackia amurensis binds with high affinity to complex-type Asn-linked oligosaccharides containing terminal sialic acid-linked alpha-2,3 to penultimate galactose residues" (1988) J Biol. Chem., 263(10): 4576-4585.
Wang et al., *Antibody Structure, Instability and Formulation*, J. Pharm. Sci., vol. 96, No. 1, pp. 1-26 (2007).
Warnock et al., "In vitro galactosylation of human IgG at 1 kg scale using recombinant galactosyltransferase" (2005) Biotechnol. Bioeng., 92(7):831-842.
Wei et al., *Glyco-engineering of human IgG1-Fc through combined yeast expression and in vitro chemoenzymatic glycosylation*, National Institute of Health Public Access Author Manuscript, Biochemistry, 47(39):10294-10304 (2008).
Weikert et al., "Engineering Chinese hamster ovary cells to maximize sialic acid content of recombinant glycoproteins" (1999) Nature Biotechnology, 17(11): 1116-1121.
Weinstein et al., "Primary structure of beta-galactoside alpha 2,6-sialyltransferase. Conversion of membrane-bound enzyme to soluble forms by cleavage of the NH2-terminal signal anchor" (1987) J. Biol. Chem. 262(36):17735-17743.
Weitzhandler et al., *Protein variant separations by cation-exchange chromatography on tentacle-type polymeric stationary phases*, Proteomics, vol. 1, pp. 179-185 (2001).

(56) References Cited

OTHER PUBLICATIONS

Wong et al., *Impact of Dynamic Online Fed-Batch Strategies on Metabolism, Productivity and N-Glycosylation Quality in CHO Cell Cultures*, Biotechnol. Bioeng., 89(2):164-177 (2005).

Wyss, et al. "The structural role of sugars in glycoproteins," Curr. Opin. Biotechnol. (1996), 7(4); 409-416.

Xie et al., *High Cell Density and High Monoclonal Antibody Production Through Medium Design and Rational Control in a Bioreactor*, Biotechnol. Bioeng., 51:725-729 (1996).

Yang et al., *Effect of Ammonia on the Glycosylation of Human Recombinant Erythropoietin in Culture*, Biotech. Progress, 16:751-759 (2000).

Yao et al., "The potential etiologic role of tumor necrosis factor in mediating multiple organ dysfunction in rats following intestinal ischemia-reperfusion injury" (1995) Resuscitation, 29(2):157-168.

Zhang et al. "A novel function for selenium in biological system: Selenite as a highly effective iron carrier for Chinese hamster ovary cell growth and monoclonal antibody production," Biotechnology and Bioengineering. (2006) 95(6):1188-1197.

Zhang et al., "CHO glycosylation mutants as potential host cells to produce therapeutic proteins with enhanced efficacy" (2013) Advances in Biochemical Engineering/Biotechnology, 131:63-87.

Zhang et al., *Mass Spectrometry for Structural Characterization of Therapeutic Antibodies*, Mass Spectrometry Reviews, 28:147-176 (2009).

Zhang, F. et al., "The Effect of Dissolved Oxygen (DO) Concentration on the Glycosylation of Recombinant Protein Produced by the Insect Cell-Baculovirus Expression System." *Biotechnology and Bioengineering*, (2002), 77(2); 219-224.

Zhang, Y. et al., *Effects of peptone on hybridoma growth and monoclonal antibody formation*, Cytotechnology, 16:147-150 (1994).

Zhou, *Implementation of Advanced Technologies in Commercial MonoclonalAntibody Production*, Biotech. J., 3:1185-1200 (2008).

Zhu, *Mammalian cell protein expression for biopharmaceutical production*, Biotech.Adv., 30:1158-1170 (2012).

Andersen et al., *Protein Glycosylation: Analysis, Characterization, and Engineering*, Encyclopedia of Industrial Biotechnology (2011), pp. 1-49.

Emea, *Avastin Scientific Discussion* (2005), pp. 1-61.

Exposure Factors Handbook, U.S. Environmental Protection Agency (1997), pp. 1-50.

\* cited by examiner

US 9,688,752 B2

LOW ACIDIC SPECIES COMPOSITIONS AND METHODS FOR PRODUCING AND USING THE SAME USING DISPLACEMENT CHROMATOGRAPHY

RELATED APPLICATION INFORMATION

This application is a continuation of U.S. application Ser. No. 14/079,076, filed on Nov. 13, 2013 which, in turn, is a continuation of U.S. application Ser. No. 14/077,576, filed on Nov. 12, 2013, which in turn claims priority to U.S. Provisional Application Ser. No. 61/892,833, filed on Oct. 18, 2013, the entire contents of each of which are expressly incorporated herein by reference.

BACKGROUND OF THE INVENTION

The production of compositions comprising proteins for biopharmaceutical applications involves the use of upstream process technologies (e.g., cell culture) and downstream process technologies (e.g., protein purification) that are known to produce proteins exhibiting varying levels of protein variants and impurities within the composition. Such protein variants include, but are not limited to, the presence of charge variants (e.g., basic variants and acidic species, including variants) and process-related impurities. For example, in monoclonal antibody (mAb) preparations, charge variants can be detected by various methods, such as ion exchange chromatography, for example, WCX-10 HPLC (a weak cation exchange chromatography) or IEF (isoelectric focusing). Because of their similar chemical characteristics to the antibody product molecules of interest, reduction of charge variants is a challenge in monoclonal antibody production.

Reduction of charge variants and/or product- or process-related impurities is particularly advantageous in the context of commercially produced recombinant biotherapeutics, as they have the potential to impact numerous product characteristics, including, but not limited to, product stability, product safety and product efficacy. Accordingly, there remains a need in the art for low acidic species compositions and high-efficiency methods of producing protein compositions, e.g., antibodies, having low levels of acidic species.

SUMMARY OF THE INVENTION

The present invention is based on the optimization of displacement chromatography process technologies for protein production, e.g., production of antibodies or antigen-binding portions thereof, resulting in the production of compositions comprising proteins that comprise low percentages of acidic species. These low acidic species compositions have improved therapeutic efficacy and improved biological properties, for example, increased cartilage tissue penetration, reduced cartilage destruction, reduced synovial proliferation, reduced bone erosion, increased protection against the development of arthritis as measured by arthritic scores and/or histopathology scores, reduced cell infiltration, reduced proteoglycan loss, reduced chondrocyte death, and/or increased TNFα affinity, as compared to a non-low acidic species composition.

Displacement chromatography is a chromatographic separation technology that involves the use of a displacer molecule to aid in the separation of a mixture, e.g., an antibody-containing solution derived from cell culture harvest. The displacer molecule is conventionally selected to have a higher affinity for the stationary phase (i.e., the chromatographic support) as compared to the components present in the material to be separated. Due to its higher affinity, the displacer molecule competes with protein mixture components for the binding sites on the stationary phase. Under appropriate conditions, the displacer induces the components of the mixture to develop into consecutive zones of concentrated and purified species in the order of decreasing binding affinity ahead of the displacer front. This ordered displacement of the components of the mixture results in the formation of a so-called "displacement train." In contrast to traditional elution mode chromatography, the displacement process takes advantage of the nonlinearity of the adsorption isotherm, allowing for higher column loading levels without compromising the purity and recovery of the component of interest. Finally, washing of the displacement train with the displacing buffer from the column allows for the component of interest to be isolated by collecting (and pooling if necessary) the proper fraction(s) of the displaced eluate.

Accordingly, in one aspect, the invention provides a method for producing a low acidic species composition comprising an antibody, or antigen-binding portion thereof, by contacting a first sample comprising the antibody, or antigen-binding portion thereof, with a chromatography media, wherein the antibody, or antigen-binding portion thereof, binds to the chromatography media; displacing the antibody, or antigen-binding portion thereof, bound to the chromatography media with a displacing buffer comprising at least one displacer molecule; and collecting a chromatography sample, wherein the chromatography sample comprises a composition of the antibody, or antigen-binding portion thereof, which contains less than about 10% acidic species, thereby producing a low acidic species composition comprising an antibody, or antigen-binding portion thereof.

In one embodiment, the chromatography media is selected from the group consisting of anion exchange adsorbent material, cation exchange adsorbent material and mixed mode media. In another embodiment, the cation exchange (CEX) adsorbent material is selected from the group consisting of a CEX resin and a CEX membrane adsorber. In another embodiment, the CEX resin is Poros XS resin.

In another embodiment, the chromatography media is a mixed mode media comprising cation exchange (CEX) and hydrophobic interaction functional groups. In one embodiment, the mixed mode media is Capto MMC resin. In another embodiment, the mixed mode media is selected from the group consisting of a CEX-based mixed mode resin and a CEX-based mixed mode membrane adsorber. In another embodiment, the mixed mode media is selected from the group consisting of CaptoMMC ImpRes, Nuvia cPrime, and Toyopearl Trp-650M resins.

In one embodiment, the pH of the displacing buffer is lower than the isoelectric point of the antibody, or antigen-binding portion thereof. In another embodiment, the pH of the displacing buffer is in the range of about 6.0 to about 8.0.

In one embodiment, the displacing buffer carries positive charge and wherein the concentration of the displacer in the displacing buffer is at least about 0.1 mM. In another embodiment, the displacer is a quaternary ammonium salt and the concentration of the displacer in the displacing buffer about 0.1 mM to about 10 mM. In another embodiment, the displacer is protamine sulfate and the concentration of the protamine sulfate in the displacing buffer is about 0.1 mM to 5 about mM.

In one embodiment, the conductivity of the displacing buffer is about 2 mS/cm to about 20 mS/cm. In another embodiment, the chromatography media is in a column, wherein the column length is in the range of about 10 cm to about 30 cm, and wherein flow residence time is in the range of about 5 min to about 25 min.

In one embodiment, one displacing buffer is used.

In another embodiment, a first displacing buffer and a second displacing buffer are used, and wherein the first and second displacing buffers comprise different concentrations of displacer. In one embodiment, the first displacing buffer comprises a lower displacer concentration of displacer than the second displacing buffer. In one embodiment, the first displacing buffer comprises about 0.5 mM Expell SP1™. In another embodiment, the first displacing buffer comprises about 0.25 mM protamine sulfate.

In one embodiment, the method is run in a two-step displacement chromatography mode.

In another embodiment, the method is run in a multiple-step displacement chromatography mode or a linear displacement chromatography mode.

In one embodiment, the chromatography sample comprises a reduced level of host cell proteins as compared to the first sample. In another embodiment, the chromatography sample comprises a reduced level of one or more of charge variants, structure variants or fragmentation variants as compared to the first sample. In one embodiment, the chromatography sample comprises a reduced level of acidic species region AR1, and wherein the charge variants comprise deamidation variants, glycation variants, afucosylation variants, MGO variants or citric acid variants. In another embodiment, the chromatography sample comprises a reduced level of the acidic species region AR1, and wherein the structure variants comprise glycosylation variants or acetonation variants. In one embodiment, the chromatography sample comprises a reduced level of the acidic species region AR1, and wherein the fragmentation variants comprise Fab fragment variants, C-terminal truncation variants or variants missing a heavy chain variable domain. In another embodiment, the chromatography sample comprises a reduced level of the acidic species region AR2, and wherein the charge variants comprise deamidation variants or glycation variants.

In another embodiment, the chromatography sample comprises a reduced level of basic species as compared to the first sample. In one embodiment, the reduced level of basic species comprise a reduced level of a lysine species Lys 0 as compared to the first sample.

In another embodiment, the chromatography sample comprises a reduced level of aggregates as compared to the first sample. In another embodiment, the chromatography sample comprises a reduced level of antibody fragments as compared to the first sample.

In one embodiment, the antibody, or antigen-binding portion thereof, is an anti-TNFα antibody, or antigen-binding portion thereof. In one embodiment, the antibody, or antigen-binding portion thereof, has dissociates from human TNFα with a $K_d$ of about $1\times10^{-8}$ M or less and a $K_{off}$ rate constant of $1\times10^{-3}$ $S^{-1}$ or less. In another embodiment, the anti-TNFα antibody, or antigen-binding portion thereof, comprises a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4. In another embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2. In another embodiment, the anti-TNFα antibody, or antigen-binding portion thereof, is adalimumab, or an antigen binding-portion thereof.

In another aspect, the present invention provides a low acidic species (low AR) composition comprising an antibody, or antigen-binding portion thereof, where the composition comprises about 15% or less AR. In one aspect of this embodiment, the low AR composition comprises about 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. In one aspect of this embodiment, the present invention provides a low AR composition comprising an antibody, or antigen-binding portion thereof, where the composition comprises about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In one embodiment, the low AR composition comprises a first acidic species region (AR1) and a second acidic species region (AR2). In one aspect of this embodiment, the low AR composition comprises about 0.1% or less AR1 and about 3% or less AR2, or about 0.0% AR1 and about 1.4% or less AR2. In a related embodiment, the low AR composition comprises about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. In one aspect of this embodiment, the present invention provides a low AR composition comprising an antibody, or antigen-binding portion thereof, where the composition comprises about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In one aspect of this embodiment, the low AR composition comprises about 15% or less 3.5% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, about 1.9%, 1.8%, 1.7%, 1.6%, 1.5%, 1.4%, 1.3%, 1.2%, 1.1%, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the present invention provides a low AR composition comprising an antibody, or antigen-binding portion thereof, where the composition comprises about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding 0%, 0.9%, 0.8%, 0.7%, 0.6%, 0.5%, 0.4%, 0.3%, 0.2% or 0.1% AR2. In another embodiment, the low AR composition comprises about 0% AR2.

In another embodiment, the low AR composition, e.g., a low AR composition of adalimumab, comprises about 1.4% or less AR. For example, in one aspect of this embodiment, the low AR composition, e.g., a low AR composition of adalimumab comprising about 1.4% or less AR can comprise about 0.0% AR1 and about 1.4% or less AR2.

In one embodiment, the acidic species in the low AR composition comprise one or more variants selected from the group consisting of charge variants, structure variants, aggregation variants and fragmentation variants. For example, in one embodiment, the charge variants in the low AR composition are AR1 species and comprise, for example, deamidation variants, glycation variants, afucosylation variants, MGO variants or citric acid variants. In another embodiment, the structure variants in the low AR composition are AR1 species and comprise, for example, glycosylation variants or acetonation variants. In still another embodiment, the fragmentation variants in the low AR composition are AR1 and comprise, for example, Fab fragment variants, C-terminal truncation variants or variants missing a heavy chain variable domain.

In another embodiment, the acidic species in the low AR composition are AR2 variants, and comprise, for example, charge variants such as deamidation variants or glycation variants.

In another aspect, the present invention provides compositions comprising an antibody, or antigen-binding portion thereof, wherein the composition is substantially free of acidic species such as process-related impurities, including, for example, host cell proteins (HCPs), host cell nucleic acids, chromatographic materials, and/or media components, as well as product related impurities such as aggregates etc.

In one embodiment, the antibody, or antigen-binding portion thereof, of the compositions disclosed herein is an anti-TNFα antibody, or antigen-binding portion thereof. For example, in one aspect of this embodiment, the anti-TNFα antibody, or antigen-binding portion thereof, dissociates from human TNFα with a $K_d$ of about $1\times10^{-8}$ M or less and a $K_{off}$ rate constant of $1\times10^{-3}$ S$^{-1}$ or less. In another aspect of this embodiment, the anti-TNFα antibody, or antigen-binding portion thereof, comprises a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4.

In still another aspect of this embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2. In yet another aspect of this embodiment, the anti-TNFα antibody, or antigen-binding portion thereof, is adalimumab, or an antigen binding-portion thereof.

In one embodiment, the low AR composition of the invention comprises adalimumab, and has a percentage of AR that is not the same as the percentage of AR present in adalimumab formulated as HUMIRA® as currently approved and described in the "Highlights of HUMIRA® Prescribing Information" for HUMIRA® (adalimumab) Injection (Revised January 2008), the contents of which are hereby incorporated herein by reference.

In another embodiment, the low AR composition of the invention comprises adalimumab, and has a percentage of AR that is lower than the percentage of AR present in adalimumab formulated as HUMIRA® as currently approved and described in the "Highlights of HUMIRA® Prescribing Information" for HUMIRA® (adalimumab) Injection (Revised January 2008), the contents of which are hereby incorporated herein by reference.

In another embodiment, the present invention provides low AR compositions comprising an anti-TNFα antibody, or antigen-binding portion thereof, comprising a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4, wherein the composition comprises less than about 10% AR. In one aspect of this embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2, wherein the composition comprises less than about 10% AR. In another aspect of this embodiment, the anti-TNFα antibody, or antigen-binding portion thereof, is adalimumab, or an antigen binding-portion thereof, and the composition comprises less than about 10% AR. In one aspect of this embodiment, the low AR composition comprising an anti-TNFα antibody, or antigen-binding portion thereof, comprises about 0.1% or less AR1 and about 3% or less AR2, or about 0.0% AR1 and about 1.4% or less AR2.

In one embodiment, the acidic species in the low AR composition comprising an antibody, or antigen-binding portion thereof (e.g., an anti-TNFα antibody, or antigen binding portion thereof, such as adalimumab) comprise one or more variants selected from the group consisting of charge variants, structure variants and fragmentation variants. For example, in one aspect of this embodiment, the charge variants in the low AR composition are AR1 species and comprise, for example, deamidation variants, glycation variants, afucosylation variants, methylglyoxal (MGO) variants or citric acid variants. For example, when the low AR composition comprises adalimumab, the deamidation variants can result from deamidation occurring at asparagine residues comprising Asn393 and Asn329 of adalimumab and at glutamine residues comprising Gln3 and Gln6. In another aspect of this embodiment, when the low AR composition comprises adalimumab, the glycation variants can result from glycation occurring at Lys98 and Lys151 of adalimumab.

In another aspect of this embodiment, the structure variants in the low AR composition comprising an antibody, or antigen-binding portion thereof (e.g., an anti-TNFα antibody, or antigen binding portion thereof, such as adalimumab) are AR1 species and comprise, for example, glycosylation variants or acetonation variants.

In still another aspect of this embodiment, the fragmentation variants in the low AR composition comprising an antibody, or antigen-binding portion thereof (e.g., an anti-TNFα antibody, or antigen binding portion thereof, such as adalimumab), are AR1 species and comprise, for example, Fab fragment variants, C-terminal truncation variants or variants missing a heavy chain variable domain.

In another embodiment, the acidic species in the low AR composition comprising an antibody, or antigen-binding portion thereof (e.g., an anti-TNFα antibody, or antigen binding portion thereof, such as adalimumab), are AR2 species, and comprise charge variants, such as deamidation variants or glycation variants. For example, when the low AR composition comprises adalimumab, the deamidation variants can result from deamidation occurring at asparagine residues comprising Asn393 and Asn329 of adalimumab and at glutamine residues comprising Gln3 and Gln6. In another aspect of this embodiment, when the low AR composition comprises adalimumab, the glycation variants result from glycation occurring at Lys98 and Lys151 of adalimumab.

In one embodiment, the percent of acidic species in a low AR composition is determined using ion exchange chromatography, for example WCX-10 HPLC. In another aspect of this embodiment, the percent acidic species in a low AR composition is determined using isoelectric focusing (IEF).

In one embodiment, the low AR compositions of the invention comprise product preparation-derived acidic species. For example, in one aspect of this embodiment, the acidic species are cell culture-derived acidic species. In another aspect of this embodiment, the acidic species of the low AR compositions are storage-derived acidic species which are primarily generated when stored under process, intermediate or shelf storage conditions prior to use.

In still another embodiment, the invention provides low AR compositions that further comprise a pharmaceutically acceptable carrier.

In another aspect, the present invention provides methods for treating a subject having a disorder in which TNFα is detrimental, by administering to the subject a low AR composition of the invention, e.g., a low AR adalimumab composition, thereby treating the subject having a disorder in which TNFα is detrimental. In one aspect of this embodiment, the disorder in which TNFα is detrimental is selected from the group consisting of rheumatoid arthritis (RA), psoriasis, psoriatic arthritis, ankylosing spondylitis, juvenile idiopathic arthritis (JIA), ulcerative colitis, Crohn's Disease, active axial spondyloarthritis (active axSpA) and non-radiographic axial spondyloarthritis (nr-axSpA).

The present invention is further illustrated by the following detailed description and claims.

DETAILED DESCRIPTION OF THE INVENTION

Figure 1:
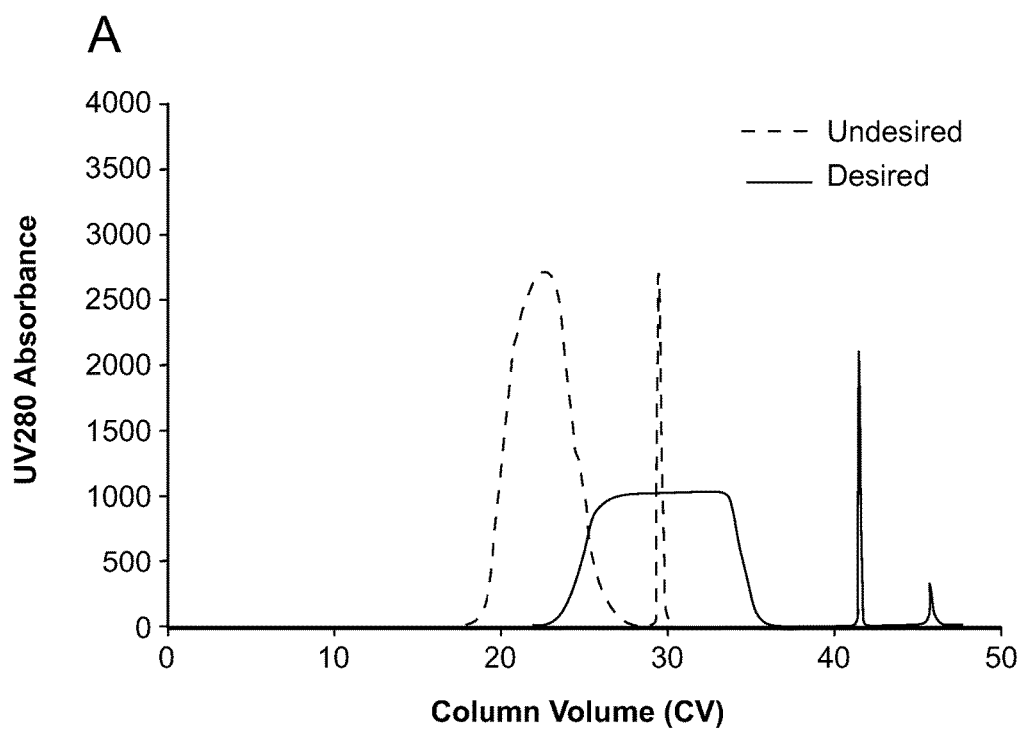
FIG. 1 depicts (a) comparison of a desired and an undesired displacement chromatogram for Adalimumab on Poros XS resin using Expell SP1™; (b) charge variants distribution in eluate fractions derived from the undesired displacement chromatography process for Adalimumab (Poros XS resin & Expell SP1™).
Figure 1:
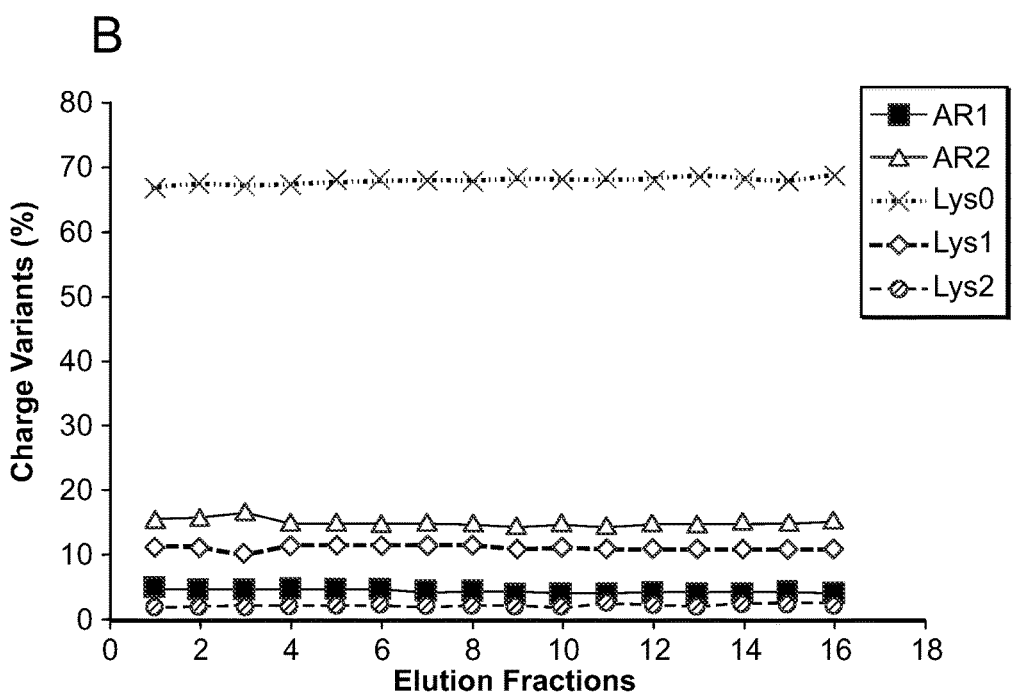

The present invention is based on the identification and optimization of displacement chromatography technologies for protein production, e.g., production of proteins, e.g., antibodies or antigen-binding portions thereof, e.g., adalimumab, resulting in compositions that comprise low percentages of protein charge variants, e.g., acidic species (AR), and basic species, and/or low levels of product- and process-related impurities (e.g., aggregates, fragments, host cell proteins and media components). In one embodiment, the displacement chromatography methods of the invention can surprisingly be used in large-scale protein purification processes due to superior resolution of closely related species using practically relevant chromatography resins and conditions. In one embodiment, the displacement chromatography methods of the invention can surprisingly be used in large-scale protein purification processes due to reduced buffer volume for a given separation, thereby providing improved process efficiency.

The compositions of the present invention exhibit increased therapeutic efficacy when administered to a subject. For example, compositions comprising anti-TNFα antibodies, or antigen binding portions thereof, comprising low AR are capable of increased therapeutic efficacy in the treatment and prevention of a disorder in which TNFα is detrimental, e.g., rheumatoid arthritis (RA), juvenile idiopathic arthritis (JIA), psoriasis, psoriatic arthritis, ankylosing spondylitis, Crohn's disease, and ulcerative colitis. Accordingly, the instant invention provides compositions comprising proteins that comprise low AR and/or low levels of product- and process-related impurities, and methods for producing and using the same.

In one embodiment, the low AR compositions of the invention comprise about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. In one aspect of this embodiment, the low AR compositions of the invention comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In another embodiment, the low AR composition comprises a first acidic species region (AR1) and a second acidic species region (AR2). In one aspect of this embodiment, the low AR composition comprises about 0.1% or less AR1 and about 3% or less AR2. In another aspect of this embodiment, the low AR composition comprises about 0.0% AR1 and about 1.4% or less AR2.

In another aspect of this embodiment, the low AR composition comprises about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1 or less, 0.3% or less AR1 or less, 0.2% or less AR1 or less, 0.1% or less AR1, or 0.0% AR1, and ranges within one or more of the preceding. In one aspect of this embodiment, the low AR compositions of the invention comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In yet another aspect of this embodiment, the low AR composition comprises about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the low AR compositions of the invention comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10%

AR2, or about 10% to about 15% AR2, and ranges within one or more of the preceding.

In another embodiment, the low AR composition, e.g., a low AR composition of adalimumab, comprises about 1.4% or less AR. For example, in one aspect of this embodiment, the low AR composition, e.g., a low AR composition of adalimumab comprising about 1.4% or less AR comprises about 0.0% AR1 and about 1.4% or less AR2.

In one embodiment, the protein is an antibody or antigen binding portion thereof, such as the adalimumab antibody, or an antigen binding portion thereof.

I. Definitions

In order that the present invention may be more readily understood, certain terms are first defined.

As used herein, the terms "acidic species", "acidic region", and "AR," refer to the variants of a protein, e.g., an antibody or antigen-binding portion thereof, which are characterized by an overall acidic charge. For example, in monoclonal antibody (mAb) preparations, such acidic species can be detected by various methods, such as ion exchange, for example, WCX-10 HPLC (a weak cation exchange chromatography), or IEF (isoelectric focusing). Acidic species of an antibody may include charge variants, structure variants, and/or fragmentation variants. Exemplary charge variants include, but are not limited to, deamidation variants, afucosylation variants, methylglyoxal (MGO) variants, glycation variants, and citric acid variants. Exemplary structure variants include, but are not limited to, glycosylation variants and acetonation variants. Exemplary fragmentation variants include any truncated protein species from the target molecule due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants include variants containing unpaired disulfides, host cell proteins, and host cell nucleic acids, chromatographic materials, and media components.

Figure 2:
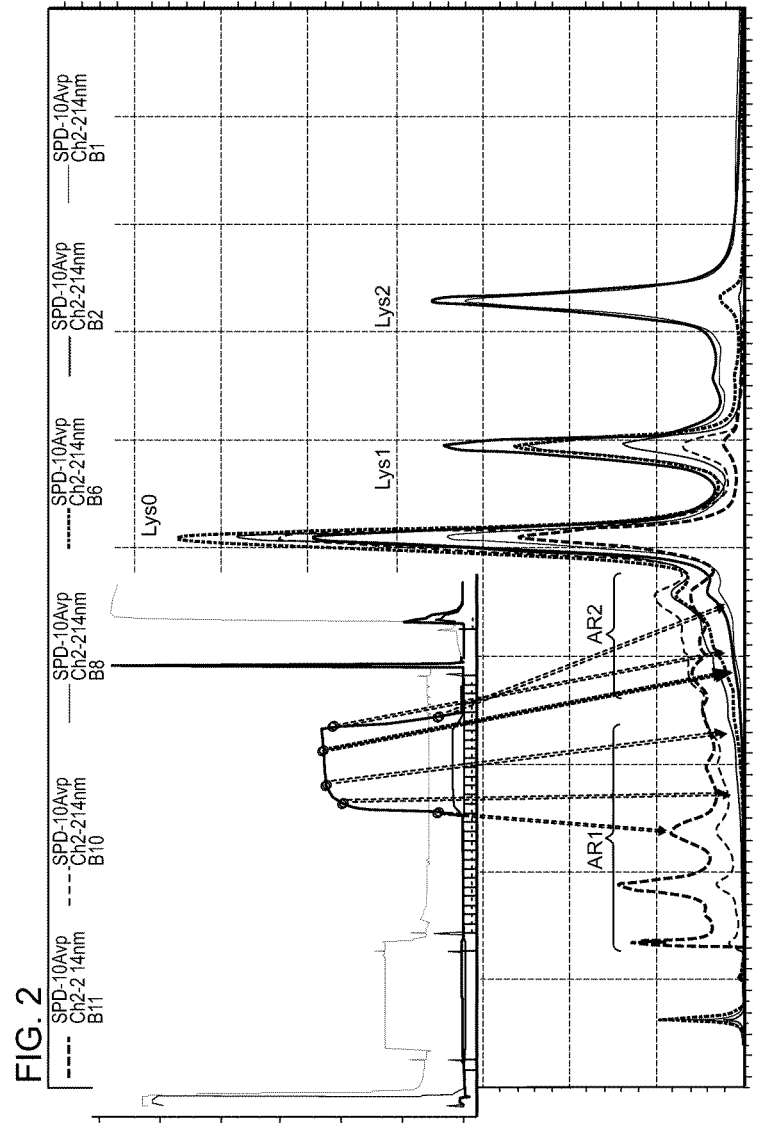
FIG. 2 depicts CEX-HPLC chromatograms of Expell SP1™-displaced Adalimumab sample fractions.

In certain embodiments, a protein composition can comprise more than one type of acidic species variant. For example, but not by way of limitation, the total acidic species can be divided based on chromatographic retention time of the peaks appearing, for example, in a WCX-10 Weak Cation Exchange HPLC of the protein preparation. FIG. 2 depicts a non-limiting example of such a division wherein the total acidic species associated with the expression of adalimumab is divided into a first acidic species region (AR1) and a second acidic species region (AR2).

AR1 can comprise, for example, charge variants such as deamidation variants, MGO modified species, glycation variants, and citric acid variants, structural variants such as glycosylation variants and acetonation variants, and/or fragmentation variants. In another embodiment, AR2 can comprise, for example, charge variants such as glycation variants and deamidation variants.

With respect, in particular, to adalimumab (and antibodies sharing certain structural characteristics of adalimumab, e.g., one or more CDR and/or heavy and light chain variable regions of adalimumab), AR1 charge variants can comprise, but are not limited to, deamidation variants, glycation variants, afucosylation variants, MGO variants or citric acid variants. In one embodiment, deamidation variants result from deamidation occurring at asparagine residues comprising Asn393 and Asn329 and at glutamine residues comprising Gln3 and Gln6. In another embodiment, the glycation variants result from glycation occurring at Lys98 and Lys151. AR1 structure variants can comprise, but are not limited to, glycosylation variants or acetonation variants.

AR1 fragmentation variants can comprise Fc and Fab fragments, fragments missing a Fab, fragments missing a heavy chain variable domain, C-terminal truncation variants, variants with excision of N-terminal Asp in the light chain, and variants having N-terminal truncation of the light chain.

AR2 charge variants can comprise, but are not limited to, deamidation variants or glycation variants, wherein the deamidation variants can result from deamidation occurring at asparagine residues comprising Asn393 and Asn329 and at glutamine residues comprising Gln3 and Gln6, and the glycation variants can result from glycation occurring at Lys98 and Lys151.

The term "acidic species" does not include process-related impurities. The term "process-related impurity," as used herein, refers to impurities that are present in a composition comprising a protein but are not derived from the protein itself. Process-related impurities include, but are not limited to, host cell proteins (HCPs), host cell nucleic acids, chromatographic materials, and media components. A "low process-related impurity composition," as used herein, refers to a composition comprising reduced levels of process-related impurities as compared to a composition wherein the impurities were not reduced. For example, a low process-related impurity composition may contain about 10%, 9%, 8%, 7%, 6%, 5%, 4%, 3%, 2%, 1%, 0.5%, or less of process-related impurities. In one embodiment, a low process-related impurity composition is free of process-related impurities or is substantially free of process-related impurities.

The acidic species may be the result of product preparation (referred to herein as "preparation-derived acidic species"), or the result of storage (referred to herein as "storage-derived acidic species"). Preparation-derived acidic species are acidic species that are formed during the preparation (upstream and/or downstream processing) of the protein, e.g., the antibody or antigen-binding portion thereof. For example, preparation-derived acidic species can be formed during cell culture ("cell culture-derived acidic species"). Storage-derived acidic species are acidic species that may or may not be present in the population of proteins directly after preparation, but are formed or generated while the sample is being stored. The type and amount of storage-derived acidic species can vary based on the formulation of the sample. Formation of storage-derived acidic species can be partially or completely inhibited when the preparation is stored under particular conditions. For example, an aqueous formulation can be stored at a particular temperature to partially or completely inhibit AR formation. For example, formation or storage-derived AR can be partially inhibited in an aqueous formulation stored at between about 2° C. and 8° C., and completely inhibited when stored at −80° C. In addition, a low AR composition can be lyophilized or freeze-dried to partially or completely inhibit the formation of storage-derived AR.

The term "low acidic species composition," or "low AR composition," as used herein, refers to a composition comprising an antibody or antigen-binding portion thereof, wherein the composition contains less than about 15% acidic species. As used herein, the percent AR in the low AR composition refers to the weight of the acidic species in a sample in relation to the weight of the total antibodies contained in the sample. For example, the percent AR can be calculated using weak cation exchange chromatography such as WCX-10, as described herein and also in Example 1 of U.S. Provisional Patent Application 61/893,068, entitled "Low Acidic Species Compositions and Methods for Producing the Same", filed on Oct. 18, 2013, the entire contents of which are expressly incorporated herein by reference.

In one embodiment, a low AR composition of the invention may comprise about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. A low AR composition of the invention may also comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

A low AR composition of the invention may comprise about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. A low AR composition of the invention may also comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

A low AR composition of the invention may also comprise about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. A low AR composition of the invention may also comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

In one embodiment, a low AR composition comprises between about 0.0% and about 3% AR1. In another embodiment, a low AR composition comprises about between about 0.0% and about 3% AR2. In a preferred embodiment, a low acidic species composition comprises about 3% or less AR2.

In another embodiment, the low AR composition comprises about 1.4% or less AR. For example, in one embodiment, the composition comprises about 1.4% AR2 and about 0.0% AR1.

In one embodiment, a low AR composition of the invention may comprise about 15% or less, 14% or less, 13% or less, 12% or less, 11% or less, 10% or less, 9% or less, 8% or less 7% or less, 6% or less, 5% or less, 4.5% or less, 4% or less, 3.5% or less, 3% or less, 2.5% or less, 2% or less, 1.9% or less, 1.8% or less, 1.7% or less, 1.6% or less, 1.5% or less, 1.4% or less, 1.3% or less, 1.2% or less, 1.1% or less, 1% or less, 0.9% or less, 0.8% or less, 0.7% or less, 0.6% or less, 0.5% or less, 0.4% or less, 0.3% or less, 0.2% or less, 0.1% or less, or 0.0% of one or more of a deamidation variant, an afucosylation variant, an MGO variant, a glycation variant, a citric acid variant, a glycosylation variant, an acetonation variant, or a fragmentation variant, and ranges within one or more of the preceding. In one aspect of this embodiment, a low AR composition of the invention may also comprise about 0.0% to about 10%, about 0.0% to about 5%, about 0.0% to about 4%, about 0.0% to about 3%, about 0.0% to about 2%, about 3% to about 5%, about 5% to about 8%, or about 8% to about 10%, or about 10% to about 15%, of one or more of a deamidation variant, an afucosylation variant, an MGO variant, a glycation variant, a citric acid variant, a glycosylation variant, an acetonation variant, or a fragmentation variant, and ranges within one or more of the preceding. For example, a low AR composition of the invention may comprise less than 15% of a deamidation variant, while each of the other acidic variants, alone or in combination, are at a percentage that is greater than 15%.

The term "non-low acidic species composition," as used herein, refers to a composition comprising an antibody or antigen-binding portion thereof, which contains more than about 13% acidic species. For example, a non-low acidic species composition may contain about 16% or more, 17% or more, 18% or more, 19% or more, 20% or more, 21% or more, 22% or more, 23% or more, 24% or more, or 25% or more acidic species. In one embodiment, a non-low acidic species composition can comprise about 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, or 25% or more of AR1. In another embodiment, a non-low acidic species composition can comprise about 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, or 25% or more of AR2, and ranges within one or more of the preceding.

In one embodiment, a low AR composition has improved biological and functional properties, including increased efficacy in the treatment or prevention of a disorder in a subject, e.g., a disorder in which TNFα activity is detrimental, as compared to a non-low acidic species composition. In one embodiment, the low AR composition comprises an anti-TNFα antibody, or antigen-binding portion thereof, such as adalimumab or a fragment thereof. For example, in one embodiment, a low AR composition comprising an antibody, or antigen-binding portion thereof, exhibits increased cartilage penetration, decreased bone erosion, and/or reduced cartilage destruction, as compared to a non-low acidic species composition comprising the same antibody or antigen binding portion thereof, when administered to a subject suffering from a disorder in which TNFα activity is detrimental.

As used herein, the term "increased cartilage penetration" refers to increased penetration of cartilage in vivo by a low AR composition as compared to a non-low AR composition comprising the same antibody or antigen binding portion thereof.

As used herein, the term "reduced cartilage destruction" refers to measurable decrease in destruction of cartilage tissue in vivo by a low AR composition as compared to a non-low AR composition comprising the same antibody or antigen binding portion thereof. As used herein, the term "decreased bone erosion" refers to measurable decrease, in vivo, of the erosion of bone tissue by a low AR composition as compared to a non-low acidic species composition comprising the same antibody or antigen binding portion thereof. For example, an in vivo model of a disease or disorder in which TNFα activity is detrimental, e.g., a mouse model of arthritis, can be used to measure cartilage penetration, bone erosion, and/or cartilage destruction by a composition comprising an anti-TNFα antibody or antigen binding portion thereof. One non-limiting example of an art-recognized mouse model of arthritis is the human TNF transgenic 197 mouse model of arthritis (TNF-Tg197) (see Keffer, J. et al., EMBO J (1991) 10:4025-4031, the contents of which are expressly incorporated herein by reference, for further description of the TNF-Tg197 model of arthritis).

In another embodiment, a low AR composition comprising an antibody, or antigen-binding portion thereof, exhibits increased protection against the development of arthritis, as measured by arthritic scores, and/or histopathology scores as compared to a non-low acidic species composition when administered to an animal model of arthritis, e.g., the TNF-Tg197 model of arthritis. As used herein, "arthritic scores" refer to signs and symptoms of arthritis in an animal model of arthritis. As used herein, "histopathology scores" refer to radiologic damage involving cartilage and bone as well as local inflammation.

In another embodiment, a low AR composition comprising an antibody, or antigen-binding portion thereof, exhibits reduced synovial proliferation, reduced cell infiltration, reduced chondrocyte death, and/or reduced proteoglycan loss as compared to a non-low acidic species composition. In another embodiment, a low AR composition comprising an anti-TNFα antibody, or antigen-binding portion thereof, exhibits increased TNFα affinity as compared to a non-low acidic species composition.

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, or synovial fluid of the subject), which can be detected, for example, using an anti-TNFα antibody as described above. There are numerous examples of disorders in which TNFα activity is detrimental. In one embodiment, the disorder in which TNFα activity is detrimental is an autoimmune disorder. In one embodiment, the autoimmune disorder is selected from the group consisting of rheumatoid arthritis, juvenile idiopathic arthritis, rheumatoid spondylitis, ankylosing spondylitis, psoriasis, osteoarthritis, gouty arthritis, an allergy, multiple sclerosis, psoriatic arthritis, autoimmune diabetes, autoimmune uveitis, nephrotic syndrome, juvenile rheumatoid arthritis, Crohn's disease and ulcerative colitis. Disorders in which TNFα activity is detrimental are set forth in U.S. Pat. No. 6,090,382 and also in the "Highlights of HUMIRA® Prescribing Information" for HUMIRA® (adalimumab) Injection (Revised January 2008) the entire contents of which are hereby incorporated herein by reference. The use of TNFα antibodies and antibody portions obtained using methods of the invention for the treatment of specific disorders is discussed in further detail below.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., in the case of adalimumab, hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is adalimumab.

As used herein, the term "adalimumab," also known by its trade name HUMIRA® (AbbVie) refers to a human IgG$_1$ antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The HUMIRA® Prescribing Information, the contents of each of which are expressly incorporated by reference herein. The light chain variable region of adalimumab is provided herein as SEQ ID NO:1, and the heavy chain variable region of adalimumab is provided herein as SEQ ID NO:2. The light chain of adalimumab is provided herein as SEQ ID NO:11, and the heavy chain of adalimumab is provided herein as SEQ ID NO:12. Adalimumab comprises a light chain variable region comprising a CDR1 of SEQ ID NO:7, a CDR2 of SEQ ID NO:5, and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. Adalimumab is described in U.S. Pat. Nos. 6,090,382; 6,258,562; 6,509,015; 7,223, 394; 7,541,031; 7,588,761; 7,863,426; 7,919,264; 8,197, 813; 8,206,714; 8,216,583; 8,420,081; 8,092,998; 8,093,045; 8,187,836; 8,372,400; 8,034,906; 8,436,149; 8,231,876; 8,414,894; 8,372,401, and PCT Publication No. WO2012/065072, the entire contents of each which are expressly incorporated herein by reference in their entireties. Adalimumab is also described in the "Highlights of Prescribing Information" for HUMIRA® (adalimumab) Injection (Revised January 2008) the contents of which are hereby incorporated herein by reference.

In one embodiment, adalimumab dissociates from human TNFα with a Kd of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC50 of 1×10-M or less. In another embodiment, adalimumab dissociates from human TNFα with a $K_{off}$ of $5\times10^4$ s$^{-1}$ or less, or with a $K_{off}$ of $1\times10^4$ s$^{-1}$ or less. In still another embodiment, adalimumab neutralizes human TNFα cytotoxicity in a standard in vitro L929 assay with an IC50 of $1\times10^{-8}$ M or less, an IC50 of $1\times10^{-9}$ M or less or an IC50 of $1\times10^{-10}$ M or less.

Analysis of adalimumab has shown that it has three main basic variants (i.e., Lys 0, Lys 1, and Lys 2), referred to herein as "lysine variant species." As used herein, the term "lysine variant species" refers to an antibody, or antigen-binding portion thereof, comprising heavy chains with either zero, one or two C-terminal lysines. For example, the "Lys 0" variant comprises an antibody, or antigen-binding portion thereof, with heavy chains that do not comprise a C-terminal lysine. The "Lys 1" variant comprises an antibody, or antigen-binding portion thereof, with one heavy chain that comprises a C-terminal lysine. The "Lys 2" variant comprises an antibody with both heavy chains comprising a C-terminal lysine. Lysine variant species can be detected by various methods, such as ion exchange, for example, by weak cation exchange chromatography (such as WCX-10) of the expression product of a host cell expressing the antibody, or antigen-binding portion thereof. For example, but not by way of limitation, FIG. 2 depicts analysis of adalimumab wherein the three lysine variants, as well as the two acidic species regions, are resolved from each other.

A composition of the invention may comprise more than one lysine variant species of an antibody, or antigen-binding portion thereof. For example, in one embodiment, the composition may comprise a Lys 2 variant of an antibody, or antigen-binding portion thereof. The composition may comprise a Lys 1 variant of an antibody, or antigen-binding portion thereof. The composition may comprise a Lys 0 variant of an antibody, or antigen-binding portion thereof. In another embodiment, the composition may comprise both Lys 1 and Lys 2, or Lys 1 and Lys 0, or Lys 2 and Lys 0 variants of an antibody, or antigen-binding portion thereof. In another embodiment, the composition may comprise all three lysine variant species, i.e., Lys 0, Lys 1 and Lys 2, of an antibody, or antigen-binding portion thereof.

In one embodiment, the invention comprises a composition comprising an antibody, or antigen-binding portion thereof, wherein the composition comprises less than about 50% lysine variant species that lack a C-terminal lysine (Lys 0). In another embodiment, the composition comprises less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% 10%, 9%, 8%, 7%, 6%, 5%, 4%, 3%, 2% or 1% lysine variant species that lack a C-terminal lysine ("Lys 0"). In another embodiment, the composition comprises about 50% to about 0%, about 40% to about 10%, about 30% to about 20%, about 40% to about 20%, or about 30% to about 15% lysine variant species that lack a C-terminal lysine (Lys 0). In one embodiment, the composition comprises 0% lysine variant species that lack a C-terminal lysine (Lys 0). As used herein, the percent lysine variant species in the composition refers to the weight of the specific lysine variant species in a sample in relation to the weight of the total lysine variant species sum (i.e., the sum of Lys 0, Lys 1 and Lys 2) contained in the sample or composition. For example, the percent lysine variant species can be calculated using weak cation exchange chromatography such as WCX-10, as described herein.

In another embodiment, the composition comprises less than about 25% lysine variant species that have one C-terminal lysine (Lys 1). In another embodiment, the composition comprises less than about 24%, 23%, 22%, 21%, 20%, 19%, 18%, 17%, 16%, 15%, 14%, 13%, 12%, 11% 10%, 9%, 8%, 7%, 6%, 5%, 4%, 3%, 2% or 1% lysine variant species that have one C-terminal lysine (Lys 1). In another embodiment, the composition comprises about 25% to about 0%, about 20% to about 5%, about 15% to about 10%, about 20% to about 10%, about 15% to about 5%, or about 25% to about 5% lysine variant species that have one C-terminal lysine (Lys 1). In one embodiment, the composition comprises 0% lysine variant species that have one C-terminal Lysine (Lys 1).

In another embodiment, the composition comprises at least about 70% lysine variant species that have two C-terminal lysines (Lys 2). In another embodiment, the composition comprises at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% lysine variant species that have two C-terminal lysines (Lys 2). In one embodiment, the composition comprises about 70% to about 100%, about 70% to about 90%, about 70% to about 80%, about 80% to about 100%, about 85% to about 100%, about 90% to about 100%, about 95% to about 100%, about 80% to about 90%, about 85% to about 95%, about 75% to about 85%, or about 97% to about 100% lysine variant species that have two C-terminal lysines (Lys 2). In one embodiment, the composition comprises 100% lysine variant species that have two C-terminal lysines (Lys 2).

As used herein, the term "upstream process technology," in the context of protein, e.g., antibody, preparation, refers to activities involving the production and collection of proteins (e.g. antibodies) from cells (e.g., during cell culture of a protein of interest). As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host, the host can be maintained under conditions suitable for expression of the relevant nucleotide coding sequences, and the collection and purification of the desired recombinant protein.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization) can be removed by a variety of means, including but not limited to, centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit.

As used herein, the term "downstream process technology" refers to one or more techniques used after the upstream process technologies to purify the protein, e.g., antibody, of interest. For example, downstream process technology includes purification of the protein product, using, for example, displacement chromatography, affinity chromatography, including Protein A affinity chromatography, ion exchange chromatography, such as anion or cation exchange chromatography, hydrophobic interaction chromatography, or displacement chromatography.

The phrase "isolated nucleic acid molecule," as used herein in reference to nucleic acids encoding antibodies or antibody portions (e.g., VH, VL, CDR3), e.g., those that bind hTNFα, includes a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, e.g., an isolated nucleic acid of the invention encoding a VH region of an anti-TNFα antibody contains no other sequences encoding other VH regions that bind antigens other than, for example, hTNFα. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant protein" refers to a protein produced as the result of the transcription and translation of a gene carried on a recombinant expression vector that has been introduced into a host cell. In certain embodiments the recombinant protein is an antibody, e.g., a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment).

The term "preparative scale," as used herein, refers to a scale of purification operation that can be readily scaled-up and implemented at large scale manufacturing while still providing desired separation. For instance, one skilled in the field may develop a process using, e.g., a 0.5 cm (i.d.)×20 cm (L) column in the lab, and transfer it to large scale production using, e.g., a 30 cm (i.d.)×20 cm (L) column packed with the same resin and operated with the same set of buffers, same linear flow rates (or residence times) and buffer volumes. In preparative scale separation, column bed height is typically ≤about 30 cm and column pressure drop≤about 5 bar.

The phrase "displacing buffer", "displacer buffer", "displacing wash buffer", or "displacer wash buffer", as used herein, refers to a buffer that comprises a displacer molecule.

The phrase "displacer molecule", as used herein, refers to a molecule employed to displace from the chromatographic support components of the mixture to be separated. Selection of a particular displacer molecule will, therefore, be dependent on the chromatographic support employed as well as the protein system. Regardless of which chromatographic support is employed, displacer molecules will generally be selected such that they have a high affinity for the support. However, in certain embodiments, a displacer molecule may be selected that has a reduced affinity for the support, so long as it retains the ability to induce a displacement train that includes the protein of interest. In certain non-limiting embodiments, the displacer molecule will be employed in the context of protein separations in ion exchange chromatography and can be selected from, but not limited to, the group consisting of: polyelectrolytes; polysaccharides; low-molecular-mass dendrimers; amino acids; peptide; antibiotics; and aminoglycosidepolyamines. In certain embodiments the displacer is selected from, but not limited to, the group consisting of: Expell SP1™ (for CEX and for mixed mode); Expell Q3 (for anion-exchange chromatography (AEX) and for mixed mode); Propel Q2 (for AEX and for mixed mode); and protamine sulfate (for CEX and for mixed mode). Exemplary displacer molecules are described in U.S. Pat. No. 7,632,409, WO 99/47574, WO 03074148, WO2007/055896, WO 2007/064809; and U.S. Pat. No. 6,881,540.

As used herein, the term"aggregates" means agglomeration or oligomerization of two or more individual molecules, including but not limiting to, protein dimers, trimers, tetramers, oligomers and other high molecular weight species. Protein aggregates can be soluble or insoluble.

II. LOW ACIDIC SPECIES COMPOSITIONS OF THE INVENTION

The present invention provides low AR compositions comprising a protein, e.g., an antibody, or antigen-binding portion thereof, such as adalimumab, where the composition comprises about 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding. A low AR composition of the invention may also comprise about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In one embodiment, a low AR composition of the invention may comprise about 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. A low AR composition of the invention may also comprise about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In another embodiment, a low AR composition of the invention may also comprise about 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. A low AR composition of the invention may also comprise about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

A low AR composition of the invention may further comprise more than one lysine variant species of an antibody, or antigen-binding portion thereof. For example, in a preferred embodiment, the composition may comprise a Lys 2 variant of an antibody, or antigen-binding portion thereof. The composition may comprise a Lys 1 variant of an antibody, or antigen-binding portion thereof. The composition may comprise a Lys 0 variant of an antibody, or antigen-binding portion thereof. In another embodiment, the composition may comprise both Lys 1 and Lys 2, or Lys 1 and Lys 0, or Lys 2 and Lys 0 variants of an antibody, or antigen-binding portion thereof. In another embodiment, the composition may comprise all three lysine variant species, i.e., Lys 0, Lys 1 and Lys 2, of an antibody, or antigen-binding portion thereof.

In one embodiment, a low AR composition of the invention comprises less than about 50% lysine variant species that lack a C-terminal lysine (Lys 0). In another embodiment, the composition comprises less than about 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% 10%, 9%, 8%, 7%, 6%, 5%, 4%, 3%, 2% or 1% lysine variant species that lack a C-terminal lysine ("Lys 0"). In another embodiment, the composition comprises about 50% to about 0%, about 40% to about 10%, about 30% to about 20%, about 40% to about 20%, or about 30% to about 15% lysine variant species that lack a C-terminal lysine (Lys 0). In one embodiment, the composition comprises 0% lysine variant species that lack a C-terminal lysine (Lys 0).

In one embodiment, a low AR composition comprises less than about 25% lysine variant species that have one C-terminal lysine (Lys 1). In another embodiment, the composition comprises less than about 24%, 23%, 22%, 21%, 20%, 19%, 18%, 17%, 16%, 15%, 14%, 13%, 12%, 11% 10%, 9%, 8%, 7%, 6%, 5%, 4%, 3%, 2% or 1% lysine variant species that have one C-terminal lysine (Lys 1). In another embodiment, the composition comprises about 25% to about 0%, about 20% to about 5%, about 15% to about 10%, about 20% to about 10%, about 15% to about 5%, or about 25% to about 5% lysine variant species that have one C-terminal lysine (Lys 1). In one embodiment, the composition comprises 0% lysine variant species that have one C-terminal Lysine (Lys 1).

In another embodiment, a low AR composition of the invention comprises at least about 70% lysine variant species that have two C-terminal lysines (Lys 2). In another embodiment, the composition comprises at least about 10%, 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% lysine variant species that have two C-terminal lysines (Lys 2). In one embodiment, the composition comprises about 70% to about 100%, about 70% to about 90%, about 70% to about 80%, about 80% to about 100%, about 85% to about 100%, about 90% to about 100%, about 95% to about 100%, about 80% to about 90%, about 85% to about 95%, about 75% to about 85%, or about 97% to about 100% lysine variant species that have two C-terminal lysines (Lys 2). In one embodiment, the composition comprises 100% lysine variant species that have two C-terminal lysines (Lys 2).

As demonstrated herein, these low AR compositions of the invention have improved biological properties. For example, the low AR compositions of the invention are characterized by increased cartilage tissue penetration, reduced cartilage destruction, reduced synovial proliferation, reduced bone erosion, increased protection against the development of arthritic scores and/or histopathology scores, reduced cell infiltration, reduced proteoglycan loss, reduced chondrocyte death, and/or increased TNFα affinity, as compared to non-low acidic species compositions. In addition, the compositions of the present invention exhibit increased therapeutic efficacy when administered to a subject.

In one embodiment, the protein in the low AR composition of the invention is an antibody or antigen binding portion thereof. For example, the antibody, or antigen binding portion thereof may be an anti-TNFα antibody, or antigen binding portion thereof, such as adalimumab, or an antigen binding portion thereof. In one aspect of this embodiment, the antibody, or antigen binding portion thereof, can comprise a light chain variable region comprising the sequence set forth as SEQ ID NO:1, and a heavy chain variable region comprising the sequence set forth as SEQ ID NO:2. In another aspect of this embodiment, the antibody can comprise a light chain variable region comprising a CDR1 having the sequence set forth as SEQ ID NO:7, a CDR2 having the sequence set forth as SEQ ID NO:5, and a CDR3 having the sequence set forth as SEQ ID NO:3. In another aspect of this embodiment, the antibody can comprise a heavy chain variable region comprising a CDR1 having the sequence set forth as SEQ ID NO:8, a CDR2 having the sequence set forth as SEQ ID NO:6 and a CDR3 having the sequence set forth as SEQ ID NO:4.

The antibody, or antigen binding portion thereof, used in the low AR compositions of the invention, may be a human, humanized, or chimeric antibody.

The antibodies that can be used in the low AR compositions of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Somatic cell hybridization procedures can be used. In principle, other techniques for producing monoclonal antibody can be employed as well, including viral or oncogenic transformation of B lymphocytes.

One exemplary animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody used in the low AR compositions of the invention can be a human, a chimeric, or a humanized antibody. Chimeric or humanized antibodies used in the low AR compositions of the invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies to be used in the low AR compositions of the invention are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and Xeno-Mouse® (Amgen). The antibodies, or antigen-binding portions thereof, used in the low AR compositions of the invention can also be produced using the methods described in U.S. Pat. No. 6,090,382, the entire contents of which is expressly incorporated herein by reference.

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies to be used in the low AR compositions of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibody Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies to be used in the low AR compositions of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the human antibodies to be used in the low AR compositions of the invention are anti-TNFα antibodies and antibody portions thereof, anti-TNFα-related antibodies and antibody portions, and human antibodies and antibody portions with equivalent properties to anti-TNFα antibodies, such as high affinity binding to hTNFα with low dissociation kinetics and high neutralizing capacity. In one aspect, the invention provides low AR compositions containing an isolated human antibody, or an antigen-binding portion thereof, that dissociates from hTNFα with a Kd of about $1\times10^{-8}$ M or less and a Koff rate constant of $1\times10^{-3}$ $s^{-1}$ or less, both determined by surface plasmon resonance. In specific non-limiting embodiments, an anti-TNFα antibody to be used in the low AR compositions of the invention competitively inhibits binding of adalimumab to TNFα under physiological conditions. In one embodiment, the low AR compositions of the invention comprise adalimumab, or an antigen binding fragment thereof.

Antibodies or fragments thereof to be used in the low AR compositions of the invention can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

To express an antibody or antigen-binding fragment thereof to be used in the low AR compositions of the invention, DNAs encoding the protein, such as DNAs encoding partial or full-length light and heavy chains in the case of antibodies, are inserted into one or more expression vector such that the genes are operatively linked to transcriptional and translational control sequences. (See, e.g., U.S. Pat. No. 6,090,382, the entire teaching of which is incorporated herein by reference.) In this context, the term "operatively linked" is intended to mean that a gene encoding the protein of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the protein of interest will comprising multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but not limited to, antibody constant region sequences. For example, one approach to converting the anti-TNFα antibody or anti-TNFα antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

A recombinant expression vector may also carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, to be used in the low AR compositions of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Mammalian cells can be used for expression and production of the recombinant protein used in the low AR compositions of the invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or U.S. Pat. No. 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antibody, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/ amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Some antibodies can be secreted directly from the cell into the surrounding growth media; others are made intracellularly. For antibodies made intracellularly, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

III. Preparation of Low AR Compositions Using Displacement Chromatography

In certain embodiments, the low AR compositions of the present invention may be produced using downstream process technologies (e.g., displacement chromatography), following cell culture of a protein.

The methods described herein for the production of compositions comprising low AR and/or low process-related impurities comprise the purification of a protein, such as an antibody or antigen-binding portion thereof, using displacement chromatography.

The methods described herein for the production of compositions comprising low AR and/or low process-related impurities also comprise the purification of a protein, such as an antibody or antigen-binding portion thereof, using displacement chromatography in combination with, for example, other types of chromatography, such as multimodal (MM) chromatography, wherein the MM media comprises both ion exchange and hydrophobic interaction functional groups, and an aqueous salt solution. In one embodiment, the same or substantially the same aqueous salt solution is used as a loading buffer and a wash buffer.

In further embodiments, the methods described herein for the production of compositions comprising low AR and/or low process-related impurities comprise the purification of a protein, such as an antibody or antigen-binding portion thereof, using displacement chromatography in combination with chromatography comprising an anion exchange (AEX) resin and an aqueous salt solution. In one embodiment, the same or substantially the same aqueous salt solution is used as a loading buffer and a wash buffer.

In yet further embodiments, the methods described herein for the production of compositions comprising low AR and/or low process-related impurities comprise the purification of a protein, such as an antibody or antigen-binding portion thereof, using displacement chromatography in combination with chromatography comprising a cation exchange (CEX) adsorbent resin and an aqueous salt solution. In one embodiment, the same or substantially the same aqueous salt solution is used as a loading buffer and a wash buffer, and the target protein bound to the CEX adsorbent resin is eluted with a buffer having a higher conductivity and/or pH than the loading/wash buffer.

In still further embodiments, the methods described herein for production of compositions comprising low AR and/or low process-related impurities comprise the purification of a protein, such as an antibody or antigen-binding portion thereof, using displacement chromatography in combination with several media, for example by using an anion exchange (AEX) resin, and chromatography using a cation exchange (CEX) adsorbent resin, in a suitable buffer, such as, for example, a Tris/Formate buffer system. In one embodiment, the sample is purified affinity chromatography media, e.g., Protein A, prior to the ion chromatography resins. For example, in one embodiment, the methods described herein for production of compositions comprising low AR comprise the exemplary process reflected in FIG. 190 of U.S. Provisional Application No. 61/893,068, entitled "Low Acidic Species Compositions and Methods for Producing and Using the Same", filed on Oct. 18, 2013, the entire contents of which are expressly incorporated herein by reference.

In one embodiment, the method for producing a low AR composition comprising an antibody, or antigen binding portion thereof, comprises contacting a first sample comprising the antibody, or antigen binding portion thereof, to affinity chromatography media in a load buffer (for example a low concentration Tris/Formate buffer), and eluting the sample from the affinity chromatography media as a first eluted sample, contacting the first eluted sample to a first chromatography media, such as an AEX chromatography resin, in a load buffer, and eluting the sample from the AEX chromatography resin as a second eluted sample. The second eluted sample is then contacted with a second chromatography media, such as a CEX chromatography resin, in a load buffer, and the sample is eluted from the CEX chromatography resin as a third eluted sample. In one embodiment, the CEX chromatography resin is eluted one, two, three or more times. In one embodiment, the process optionally includes one or more intermediate filtration steps, pH adjustment steps and inactivation steps.

In one embodiment, the displacement chromatography steps, alone or in combination with other purification steps, produce a low AR composition comprising an antibody, or antigen binding portion thereof, which contains 15% or less AR, 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% AR, 0.3% or less AR, 0.2% or less AR, 0.1% or less AR, or 0.0% AR, and ranges within one or more of the preceding. In one aspect of this embodiment, the low AR composition of the invention comprises about 0.0% to about 10% AR, about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding.

In one embodiment, the displacement chromatography steps, alone or in combination with other purification steps, produce a low AR composition comprising an antibody, or antigen binding portion thereof, which contains 15% or less AR1, 14% or less AR1, 13% or less AR1, 12% or less AR1, 11% or less AR1, 10% or less AR1, 9% or less AR1, 8% or less AR1, 7% or less AR1, 6% or less AR1, 5% or less AR1, 4.5% or less AR1, 4% or less AR1, 3.5% or less AR1, 3% or less AR1, 2.5% or less AR1, 2% or less AR1, 1.9% or less AR1, 1.8% or less AR1, 1.7% or less AR1, 1.6% or less AR1, 1.5% or less AR1, 1.4% or less AR1, 1.3% or less AR1, 1.2% or less AR1, 1.1% or less AR1, 1% or less AR1, 0.9% or less AR1, 0.8% or less AR1, 0.7% or less AR1, 0.6% or less AR1, 0.5% or less AR1, 0.4% or less AR1, 0.3% or less AR1, 0.2% or less AR1, 0.1% or less AR1, or 0.0% AR1, and ranges within one or more of the preceding. In one aspect of this embodiment, the low AR composition of the invention comprises about 0.0% to about 10% AR1, about 0.0% to about 5% AR1, about 0.0% to about 4% AR1, about 0.0% to about 3% AR1, about 0.0% to about 2% AR1, about 3% to about 5% AR1, about 5% to about 8% AR1, or about 8% to about 10% AR1, or about 10% to about 15% AR1, and ranges within one or more of the preceding.

In one embodiment, the displacement chromatography steps, alone or in combination with other purification steps, produce a low AR composition comprising an antibody, or antigen binding portion thereof, which contains 15% or less AR2, 14% or less AR2, 13% or less AR2, 12% or less AR2, 11% or less AR2, 10% or less AR2, 9% or less AR2, 8% or less AR2, 7% or less AR2, 6% or less AR2, 5% or less AR2, 4.5% or less AR2, 4% or less AR2, 3.5% or less AR2, 3% or less AR2, 2.5% or less AR2, 2% or less AR2, 1.9% or less AR2, 1.8% or less AR2, 1.7% or less AR2, 1.6% or less AR2, 1.5% or less AR2, 1.4% or less AR2, 1.3% or less AR2, 1.2% or less AR2, 1.1% or less AR2, 1% or less AR2, 0.9% or less AR2, 0.8% or less AR2, 0.7% or less AR2, 0.6% or less AR2, 0.5% or less AR2, 0.4% or less AR2, 0.3% or less AR2, 0.2% or less AR2, 0.1% or less AR2, or 0.0% AR2, and ranges within one or more of the preceding. In one aspect of this embodiment, the low AR composition of the invention comprises about 0.0% to about 10% AR2, about 0.0% to about 5% AR2, about 0.0% to about 4% AR2, about 0.0% to about 3% AR2, about 0.0% to about 2% AR2, about 3% to about 5% AR2, about 5% to about 8% AR2, or about 8% to about 10% AR2, or about 10% to about 15% AR2, and ranges within one or more of the preceding.

Protein Purification Generally

Following upstream processing of a protein of interest, downstream process technologies can be used to purify the protein. For example, but not by way of limitation, once a clarified solution or mixture comprising the protein of interest, for example, an antibody or antigen binding fragment thereof, has been obtained, separation of the protein of interest from the process-related impurities, aggregates, fragments, and/or charge variant species (e.g., acidic species and basic species) can be effected using displacement chromatography, either alone or in combination with different purification techniques, including, but not limited to, affinity separation steps, ion exchange separation steps, mixed mode separation steps, and hydrophobic interaction separation steps, singularly or in combination. The separation steps separate mixtures of proteins on the basis of their charge, degree of hydrophobicity, or size, or any combination thereof, depending on the particular form of separation, including chromatographic separation. In one aspect of the invention, separation is performed using chromatography, including cationic, anionic, and hydrophobic interaction. Several different chromatography resins are available for each of these techniques, allowing accurate tailoring of the purification scheme to the particular protein involved. Each of the separation methods result in the protein traversing at different rates through a column, to achieve a physical separation that increases as they pass further through the column, or adhere selectively to the separation medium. The proteins are then differentially eluted by different solvents. In some cases, the antibody is separated from impurities when the impurities preferentially adhere to the column and the antibody less so, i.e., the desired antibody variant is present in the Flow Through.

In certain embodiments, a low AR composition is produced using displacement chromatography to identify the particular conditions, e.g., displacers, displacer concentration, salt concentration, pH, temperature, load amount and conditions, and washing conditions, sufficient to elicit the desired fractionation profile, e.g., fractionation of acidic species and lysine variants, of a sample comprising the protein of interest and at least one process-related impurity. In certain embodiments, the method further comprises pooling the resulting fractions comprising the desired low AR composition.

The purification process may begin at the separation step after the antibody has been produced using upstream production methods described herein and in U.S. Provisional Application No. 61/893,068, entitled "Low Acidic Species Compositions and Methods for Producing and Using the Same", filed on Oct. 18, 2013, the entire contents of which are incorporated herein by reference, and/or by alternative production methods conventional in the art. Once a clarified solution or mixture comprising the protein of interest, e.g., an antibody, has been obtained, separation of the protein of interest from process-related impurities, such as the other proteins produced by the cell, as well as product-related substances, such as acidic or basic variants, is performed.

In certain non-limiting embodiments, such separation is performed using cation exchange (CEX), anion exchange (AEX), and/or mixed mode (MM) chromatography. In certain embodiments, a combination of one or more different purification techniques, including affinity separation step(s), ion exchange separation step(s), mixed-mode step(s), and/or hydrophobic interaction separation step(s) can also be employed. Such additional purification steps separate mixtures of proteins on the basis of their charge, degree of hydrophobicity, and/or size. In one aspect of the invention, such additional separation steps are performed using chromatography, including hydrophobic, anionic or cationic interaction (or a combination thereof). Numerous chromatography resins are commercially available for each of these techniques, allowing accurate tailoring of the purification scheme to the particular protein involved. Each of the separation methods allow proteins to either traverse at different rates through a column, achieving a physical separation that increases as they pass further through the column, or to adhere selectively to a separation resin (or medium).

The proteins are then differentially eluted using different eluents. In some cases, the protein of interest is separated from impurities when the impurities specifically adhere to the column's resin and the protein of interest does not, i.e., the protein of interest is contained in the effluent, while in other cases the protein of interest will adhere to the column's resin, while the impurities and/or product-related substances are extruded from the column's resin during a wash cycle.

Primary Recovery and Virus Inactivation

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be performed at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 μm filter such as Sartorius's 0.45/0.2 μm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, buffer/detergent treatment, UV and γ-ray irradiation and the addition of certain chemical inactivating agents such as β-propiolactone or e.g., copper phenanthroline as described in U.S. Pat. No. 4,534,972. In certain embodiments of the present invention, the sample matrix is exposed to detergent viral inactivation during the primary recovery phase. In other embodiments, the sample matrix may be exposed to low pH inactivation during the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, prior to continuing the purification process. Additionally, the mixture may be diluted with water for injection (WFI) to obtain a desired conductivity.

Affinity Chromatography

In certain embodiments, it will be advantageous to subject a sample produced by the techniques of the instant invention to affinity chromatography to further purify the protein of interest away from acidic species before a displacement chromatography step. In certain embodiments the chromatographic material is capable of selectively or specifically binding to the protein of interest ("capture"). Non-limiting examples of such chromatographic material include: Protein A, Protein G, chromatographic material comprising, for example, an antigen bound by an antibody of interest, and chromatographic material comprising an Fc binding protein. In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin is MabSelect™ from GE Healthcare. Suitable resins include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies. A non-limiting example of a suitable column packed with MabSelect™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™.

Protein A Affinity Chromatography

In certain embodiments, particularly where the protein of interest is an antibody, the composition, e.g., a primary recovery sample, is subjected to Protein A affinity chromatography before displacement chromatography to produce the low AR compositions of the invention. There are a variety of commercial sources for Protein A resin. Suitable resins include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies.

The Protein A column can be equilibrated with a suitable buffer prior to sample loading. Following the loading of the column, the column can be washed one or multiple times using a suitable sets of buffers. The Protein A column can then be eluted using an appropriate elution buffer. For example, glycine-HCL or citric acid can be used as an elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

The invention is not limited to capture of the protein of interest using Protein A chromatography. A non-Protein A chromatography capture step can also be carried out. For example, cation exchange capture and non-chromatographic methods, such as aqueous two phase extraction or precipitation, or other methods known in the art, can be used.

Displacement Chromatography

In certain embodiments of the present invention, a protein sample, e.g., a primary recovery sample from cell culture, a Protein A eluate sample, or a sample having undergone one or more of the other purification strategies outlined herein, is subjected to displacement chromatography to produce the low AR compositions of the invention. In certain embodiments, the displacer molecule is selected to have a higher affinity for the stationary phase (i.e., the chromatographic support) than the components present in the material to be separated. In certain embodiments, the displacer induces the components of the mixture to develop into consecutive zones of concentrated and purified species in the order of decreasing binding affinity ahead of the displacer front (a "displacement train"). In certain embodiments, the displacement process allows for higher column loading levels (as compared to conventional high-resolution chromatographic separations such as bind and linear gradient elution mode) without compromising the purity and recovery of the component of interest. In certain embodiments, washing of the displacement train from the column using the displacer solution allows for the component of interest to be isolated by collecting (and pooling if necessary) the proper fraction(s) of the displaced eluate. Along with acidic species, other product-related substances, such as basic species, product aggregates, and/or product fragments, and process-related impurities, such as HCPs, can be selectively collected or reduced using displacement chromatography.

Displacement chromatography in described, in general, in Brgles et al., Journal of Chromatography A, 1218 (2011) 2389-2395; Gajdosik et al., Journal of Chromatography A, 1239 (2012) 1-9; Gerstner et al., Biotechnol. Prog., (1992), 8, 540-545; Kundu et al., Analytical Biochemistry, 248, 111-116, (1997); and Vogt et al., Journal of Chromatography A, 760 (1997) 125-137.

In certain embodiments, the displacer will be employed in the context of an ion exchange, e.g., anion exchange or cation exchange, or mixed mode chromatographic separation. A detailed description of ion exchange chromatography and a listing of exemplary chromatographic supports which can be employed in the context of displacement chromatography are presented below. A detailed description of mixed mode chromatography and a listing of exemplary chromatographic supports which can be employed in the context of displacement chromatography are also presented below. In certain non-limiting embodiments, a cation exchange, an anion exchange, or a mixed mode displacement chromatography step is employed to effectively reduce product-related substances (e.g., acidic species and/or basic species such as lysine variant species) from, e.g., a monoclonal antibody feed stream. In specific embodiments, conventional (or relatively weak) binding conditions can be employed and cationic molecules having high affinity for a CEX, AEX, or multimodal ligand (such as Expell SP1™ and protamine sulfate) can be employed to induce the formation of a product-related substances displacement train. In certain of such embodiments, the acidic species variant population is enriched in the front followed by the main isoform, and, thereafter, the basic population. Thus, in certain embodiments, exclusion of those earlier fractions from the remainder eluate results in an AR-reduced product. Alternatively, exclusion of the fractions following the main isoform results in a lysine species variant-reduced product. In certain embodiments, the fragments and aggregates are reduced in an AR-reduced product. In certain embodiments, the HCPs are reduced in an AR-reduced product.

In certain embodiments, the displacer concentration will be selected from the range of about 0.1 mM to about 10 mM, or about 0.25 mM to about 10 mM. In certain embodiments, the displacer concentration will be selected from a range of about 0.1 mM to about 5 mM, or about 0.25 mM to about 3 mM. In certain embodiments, the displacer concentration will be selected from a range of about 0.1 mM to about 5 mM, or about 0.25 mM to about 2 mM. In certain embodiments, the displacer concentration will be selected from a range of about 0.1 mM to about 2 mM, or about 0.25 mM to about 1 mM. In certain embodiments, the displacer concentration will be selected from a concentration of about 0.1 mM to about 1 mM, or about 0.25 mM to about 0.5 mM.

In certain embodiments the displacer is Expell SP1™ and the displacer concentration will be selected from the range of about 0.1 mM to about 10 mM, or about 0.25 mM to about 10 mM. In certain embodiments, the displacer is protamine sulfate and the displacer concentration will be selected from the range of about 0.1 mM to about 5 mM, or about 0.25 mM to about 5 mM.

In certain embodiments, a displacing buffer is used in one-step displacement process. In certain embodiments, the total volume of the one-step displacing buffer is in the range of about 20 CVs to about 50 CVs, or about 25 CVs to about 40 CVs, or about 30 CVs. In another embodiment, the total volume of the one-step displacing buffer is about 15 CVs, about 20 CVs, about 25 CVs, about 30 CVs, about 35 CVs, about 40 CVs, about 45 CVs, or about 50 CVs.

Although displacement chromatography conventionally employs a displacer at a fixed concentration to achieve component separation, an improved method using multiple displacing buffers is also disclosed herein. For example, a two-step displacement method is employed where a first displacer concentration is employed for a certain initial number of column volumes (CVs) and a second, higher, displacer concentration is employed for a subsequent number of CVs. The total volume of the displacing buffers needed to complete the displacement process is significantly (e.g., 25-45%) less than that needed when using one displacing buffer in the one-step displacement process in order to achieve comparable separation performances. In certain embodiments, the first displacer concentration is about 0.25 mM, about 0.3 mM, about 0.35 mM, about 0.4 mM, about 0.45 mM, or about 0.5 mM. In certain embodiments, the second displacer concentration is about 0.5 mM, about 1 mM, about 1.5 mM, about 2 mM, about 2.5 mM, about 3 mM, about 3.5 mM, about 4 mM, about 4.5 mM, or about 5 mM.

In certain embodiments, a two-step displacement method is employed where the first displacer concentration is employed for up to about 10 CVs. In certain embodiments, the first displacer concentration is employed for up to about 25 CVs. In another embodiments, the first displacer concentration is employed for up to about 10, 11 12, 13, 14, 15, 16, 17, 18, 19, 20, 21, 22, 23, 24 or 25 CVs.

In certain embodiments, the second displacer concentration is employed for up to about 10 CVs. In certain embodiments, the second displacer concentration is employed for up to about 25 CVs. In another embodiment, the second displacer concentration is employed for up to about 10, 1112, 13, 14, 15, 16, 17, 18, 19, 20, 21, 22, 23, 24 or 25 CVs.

In certain embodiments, the total required displacing buffer volume is about 13 CVs for a two-step displacement process. In certain embodiments, the total required displacer buffer volume is about 15 CVs for a two-step displacement process. In certain embodiments, the total required displacer buffer volume is about 33 CVs for a two-step displacement process. In another embodiment, the total required displacing buffer volume is about 10, 11, 12, 13, 14, 115, 16, 17, 18, 19, 20, 21, 22, 23, 24, 25, 26, 27, 28, 29, 30, 31, 32, 33, 34 or 35 CVs for a two-step displacement process.

One of skill in the art would understand that further reduction in required buffer volumes for each displacement step is expected. In certain embodiments, multiple steps of increasing displacer concentration are employed. As outlined in the Examples section, below, incorporation of additional displacement concentration steps into the purification strategy can allow for unexpectedly efficient charge variant, product aggregate, product fragment, and/or HCP clearance. For example, in one embodiment, three, four, five, six, seven, eight, nine or ten displacement concentration steps are used.

In certain embodiments, a linear gradient displacement method is employed where an initial, low, displacer concentration is followed by the addition of displacer at increasing concentrations in accordance with a linear gradient. For example, but not by way of limitation, the displacer concentration can range from about 0 mM to about 1 mM over the course of about 40 CVs. Again, as outlined in the Examples section, below, incorporation of a linear displacer concentration gradient into the purification strategy can allow for unexpectedly efficient charge variant, product aggregate, product fragment, and/or HCP clearance.

In certain embodiments, a displacement buffer consisting of two or more displacers is used. In certain embodiments, different displacers are used in the multi-step displacement process. For example, a displacement buffer consisting of two, three, four, five, six, seven, eight, nine or ten displacers may be used. Alternatively, two, three, four five, six, seven, eight, nine or ten displacers may be used in a multi-step displacement process.

In certain embodiments of the present invention, the pH of the displacing wash buffer is below the pI of the protein of interest. In certain embodiments, the pH of the displacing wash buffer is in the range of about 5.0 to about 9.0, about 6.0 to about 8.0, about 7.0 to about 7.7, or about 7.5 to about 7.7. In another embodiment, the pH of the displacing wash buffer is about 5, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

In certain embodiments of the present invention, the conductivity of the displacing wash buffer is between about 1 to about 86 mS/cm, about 2 to about 20 mS/cm, about 2 to about 7 mS/cm, or about 5 to about 6.6 mS/cm. In another embodiment, the conductivity of the displacing wash buffer is about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85 or 86 mS/cm.

In certain embodiments of the present invention, the column bed height is between about 10 cm to about 30 cm, about 15 cm to about 25 cm, about 20 cm to about 30 cm, or about 25 cm. In another embodiment, the column bed height is about 10, 11, 12, 13, 14, 15, 16, 17, 18, 19, 20, 21, 22, 23, 24, 25, 26, 27, 28, 29, 30, 31, 32, 33, 34 or 35 cm.

In certain embodiments of the present invention, the flow residence time is between about 2 minutes to about 25 minutes, about 5 minutes to about 20 minutes, about 10 minutes to about 20 minutes, or about 15 minutes to about 20 minutes. In another embodiment, the flow residence time is about 1, 2, 3, 4, 5, 6, 7, 8, 9, 10, 11, 12, 13, 14, 15, 16, 17, 18, 19, 20, 21, 22, 23, 24 or 25 minutes.

In certain embodiments, the displacer buffer pH and displacer concentration can affect the displacement profile and, as a result, impact clearance of process-related impurities and/or product-related substances, such as charge variants, in unexpected ways. Thus, effective operating regimes with regard to the reduction of process-related impurities and/or product-related substances depend on the specific protein-resin-displacer system. For example, but not by way of limitation, when a feed stream containing Adalimumab is separated using displacement chromatography, significant AR reduction ($\Delta$AR %) can be achieved using a displacing buffer with pH in the range of 6-8 with displacer concentration as low as 0.25-0.5 mM. In fact, as described in Example 2 below, the extent of Adalimumab AR reduction increases significantly as pH varies from 6.5 to 7.5, for example, over a 6% decrease in AR level can be achieved at pH 7.5 with a product yield ~75%. In certain embodiments, as outlined in the Examples presented below, the total AR level (%) in Adalimumab product pool can be reduced by over 10% with an acceptable processing yield ($\geq$75%) from a CEX displacement chromatography process, or 4-7% from a mixed mode displacement chromatography process. Similarly, for mAb X, FIG. 32 indicates that $\Delta$AR % surprisingly increases from 3.3 to 6.5% as pH varies from 7 to 7.7 in a mixed mode displacement chromatography process.

In certain embodiments, conditions selected for reducing AR are also capable of reducing process-related impurities and/or other product-related substances. For example, but not by way of limitation, conditions selected for AR reduction are also capable of reducing process-related impurities, such as HCPs. In additional, non-limiting examples, conditions selected for AR reduction are also capable of reducing product-related impurities, such as aggregates and/or fragments.

In certain embodiments, displacement chromatography can be used as the sole method of purification of the protein of interest. In certain embodiments, displacement chromatography can be used in combination with other purification strategies, such as, but not limited to, the alternative purification techniques described herein, to reduce process-related impurities and/or other product-related substances. In one embodiment, displacement chromatography is used following Protein A affinity steps.

In certain embodiments, fractions are collected during the displacement step and are combined (pooled) after appropriate analysis to provide a protein preparation, which is also referred to herein as a purified or partially-purified sample, that contains a desired level of the protein of interest and which can include one or more process-related impurities and/or other product-related substances. In certain embodiments, one or more process monitoring tools can be used in connection with the techniques described herein to facilitate the identification of an effective product pooling strategy. In certain embodiments, such monitoring can include on-line or in-line process monitoring. For example, but not by way of limitation, spectroscopy methods such as UV, NIR, FTIR, Fluorescence, and Raman may be used to monitor levels of product-related species, e.g., acidic species and lysine variants, in an on-line, at line or in-line mode. These methods allow for the production of data that can then be used to control the level of product-related species in the pooled material collected. In certain embodiments, specific signals arising from the chemical modification of the proteins such as glycation, MGO modification, deamidation, glycosylation may be specifically measurable by spectroscopic methods through such in-line, on-line or at-line methods, enabling real time or near-real time control of product quality of the resulting product.

In certain embodiments, the purification and/or pooling techniques described herein allow for the reduction of process-related impurities and/or other product-related substances. In certain embodiments, the purification and/or pooling techniques described herein allow for reduction of process-related impurities and the selective inclusion of particular product-related substances. For example, but not by way of limitation, the purification and/or pooling techniques described herein allow for modulation of the concentration of product-related substances in the purified sample, e.g., increasing or decreasing the amount of AR and/or basic species. In certain embodiments, the concentration of particular AR and/or basic species, e.g., Lys 0, Lys 1, and/or Lys 2, are modulated (increased or decreased) in the purified sample. In certain embodiments, such techniques can be used to ensure product uniformity over the course of multiple production runs.

Anion Exchange (AEX) Chromatography

In certain embodiments, the low AR compositions of the invention are produced by subjecting a primary protein recovery sample to at least one anion exchange separation step after the above-described displacement chromatography step. In another embodiment, the anion exchange step will occur before the above-described displacement chromatography step. In one embodiment, the anion exchange chromatography step will occur after the above-described Protein A affinity and displacement chromatography steps.

The use of an anionic exchange material versus a cationic exchange material, such as those cation exchange materials discussed in detail below, is based on the local charges of the protein of interest in a given solution. Therefore, it is within the scope of this invention to employ an anionic exchange step prior to the use of a cationic exchange step, or a cationic exchange step prior to the use of an anionic exchange step. Furthermore, it is within the scope of this invention to employ only an anionic exchange step, only an cationic exchange step, or any serial combination of the two (including serial combinations of one or both ion exchange steps with the other chromatographic separation technologies described herein).

In performing the separation, the initial protein composition can be contacted with the anion exchange material by using any of a variety of techniques, e.g., using a batch purification technique or a chromatographic technique.

For example, in the context of batch purification, anion exchange material is prepared in, or equilibrated to, the desired starting buffer. Upon preparation, or equilibration, a slurry of the anion exchange material is obtained. The protein of interest, e.g., antibody, solution is contacted with the slurry to allow for protein adsorption to the anion exchange material. The solution comprising the acidic species that do not bind to the AEX material is separated from the slurry, e.g., by allowing the slurry to settle and removing the supernatant. The slurry can be subjected to one or more washing steps and/or elution steps.

In the context of chromatographic separation, a chromatographic apparatus, commonly cylindrical in shape, is employed to contain the chromatographic support material (e.g., AEX material) prepared in an appropriate buffer solution. The chromatographic apparatus, if cylindrical, can have a diameter of about 5 mm to about 2 meters, and a height of 5 cm to 50 cm, and in certain embodiments, particularly for large scale processing, a height of ≤30 cm is employed. Once the chromatographic material is added to the chromatographic apparatus, a sample containing the protein of interest, e.g., an antibody, is contacted to the chromatographic material to induce the separation. Any portion of the solution that does not bind to the chromatographic material, e.g., which may comprise, depending on the AEX material being employed, the protein of interest, acidic species, is separated from the chromatographic material by washing the material and collecting fractions from column. The chromatographic material can be subjected to one or more wash steps. If desired, the chromatographic material can then be contacted with a solution designed to desorb any components of the solution that have bound to the chromatographic material.

In certain embodiments, a wash step can be performed in the context of AEX chromatography using conditions similar to the load conditions or alternatively by decreasing the pH and/or increasing the ionic strength/conductivity of the wash in a step wise or linear gradient manner. The resulting Flow Through and wash fractions can be analyzed and appropriate fractions pooled to achieve the desired reduction in charged variant species. In certain embodiments, the aqueous salt solution used as both the loading and wash buffer has a pH that at or near the isoelectric point (pI) of the protein of interest. In certain embodiments the pH is about 0 to 2 units higher or lower than the pI of the protein of interest. In certain embodiments, it will be in the range of 0 to 0.5 units higher or lower. In certain embodiments, it will be at the pI of the antibody.

In certain non-limiting embodiments, the anionic agent is selected from the group consisting of acetate, formate, or combinations thereof. In certain non-limiting embodiments, the cationic agent is selected from the group consisting of Tris, arginine, or combinations thereof. In one embodiment, the buffer solution is a Tris/formate buffer. In another embodiment, the buffer is selected from the group consisting of pyridine, piperazine, L-histidine, Bis-tris, Bis-tris propane, imidazole, N-Ethylmorpholine, TEA (triethanolamine), Tris, Morpholine, N-Methyldiethanolamine, AMPD (2-amino-2-methyl-1,3-propanediol), diethanolamine, ethanolamine, AMP (2-amino-2-methyl-1-propanol), piperazine, 1,3-Diaminopropane and piperidine.

A packed anion-exchange chromatography column, anion-exchange membrane device, anion-exchange monolithic device, or depth filter media can be operated either in bind-elute mode, flow-through mode, or a hybrid mode wherein the product exhibits binding to the chromatographic material, yet can be washed from the column using a buffer that is the same or substantially similar to the loading buffer. In the bind-elute mode, the column or the membrane device is first conditioned with a buffer with appropriate ionic strength and pH under conditions where certain proteins will be immobilized on the resin based matrix. For example, in certain embodiments, during the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or stepwise (step elution). In the flow-through mode, the column or the membrane device is operated at selected pH and conductivity such that the protein of interest does not bind to the resin or the membrane while the acidic species will either be retained on the column or will have a distinct elution profile as compared to the protein of interest. In the context of this hybrid strategy, acidic species will bind to the chromatographic material (or Flow Through) in a manner distinct from the protein of interest, e.g., while the protein of interest and certain aggregates and/or fragments of the protein of interest may bind the chromatographic material, washes that preferentially remove the protein of interest can be applied. The column is then regenerated before next use.

Non-limiting examples of anionic exchange substituents include diethylaminoethyl (DEAE), quaternary aminoethyl (QAE) and quaternary amine (Q) groups. Additional non-limiting examples include: Poros 50PI and Poros 50HQ, which are a rigid polymeric bead with a backbone consisting of cross-linked poly[styrene-divinylbenzene]; Capto Q Impres and Capto DEAE, which are a high flow agarose bead; Toyopearl QAE-550, Toyopearl DEAE-650, and Toyopearl GigaCap Q-650, which are a polymeric base bead; Fractogel® EMD TMAE Hicap, which is a synthetic polymeric resin with a tentacle ion exchanger; Sartobind STIC® PA nano, which is a salt-tolerant chromatographic membrane with a primary amine ligand; Sartobind Q nano; which is a strong anion exchange chromatographic membrane; CUNO BioCap; which is a zeta-plus depth filter media constructed from inorganic filter aids, refined cellulose, and an ion exchange resin; and X0HC, which is a depth-filter media constructed from inorganic filter aid, cellulose, and mixed cellulose esters. The detailed information is listed in Table A.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the methods of the instant invention can be used to selectively remove, significantly reduce, or essentially remove all of AR in the Flow Through and wash fractions while enriching for the same in the flow elution fraction, thereby producing protein compositions that have reduced AR or are free of AR. In certain embodiments relating to the purification of adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments relating to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including but not limited to those relating to adalimumab, the methods of the instant invention can be used to selectively remove, significantly reduce, or essentially remove all of the MGO variants in the Flow Through and wash fractions while enriching for the same in the elution fraction, thereby producing protein compositions that have reduced MGO or are free of MGO variants (for example, see U.S. Patent Application Ser. No. 61/777,883, filed on Mar. 12, 2013). In certain embodiments, including, but not limited to those relating to adalimumab, the methods

TABLE A

List of AEX Adsorbent Properties

| AEX Adsorbent | Vendor | Media Type | Ligand Type | Particle/ Pore Size | Catalog Number |
|---|---|---|---|---|---|
| Poros PI | Applied Biosystems | Resin | Weak | ~50 μm | 1-2459-11 |
| Poros HQ | | | Strong | ~50 μm | 1-2559-11 |
| Capto DEAE | GE | | Weak | ~90 μm | 17-5443-10 |
| CaptoQ Impres | | | Strong | ~90 μm | 17-5316-10 |
| QAE-550 | Tosoh | | Strong | ~100 μm | 43271 |
| DEAE-650 | | | Weak | ~65 μm | 43201 |
| GigaCap Q-650 | | | Strong | ~75 μm | 21854 |
| TMAE HiCap | EMD/Millipore | | Strong | ~40-90 μm | 1.16881.0013 |
| Sartobind STIC ® PA Nano | Sartorius | Membrane | Weak | 3-5 μm | 92STPA42DN-11-A |
| Sartobind Q Nano | | | Strong | 3-5 μm | 92IEXQ42DN-11 |
| CUNO BioCap 25 | 3M | Depth Filter | NA | NA | BC0025L60ZA05A |
| X0HC | Millipore | | NA | NA | MX0HC23CL3 |

In certain embodiments, the protein load of the mixture comprising protein of interest is adjusted to a total protein load to the column of between about 50 and 500 g/L, or between about 75 and 350 g/L, or between about 200 and 300 g/L. In certain embodiments, the protein concentration of the load protein mixture is adjusted to a protein concentration of the material loaded to the column of about 0.5 and 50 g/L, between about 1 and 20 g/L, or between 3 and 10 g/L. In certain embodiments, the protein concentration of the load protein mixture is adjusted to a protein centration of the material to the column of about 37 g/L.

of the instant invention can be used to selectively remove, significantly reduce, or essentially remove all of the glycated variants (Schiff's base and permanently glycated forms) in the Flow Through and wash fractions while enriching for the same in the elution fraction, thereby producing protein preparations with reduced or free of glycated variants.

In certain embodiments, the loading, pH, conductivity of the AEX chromatography step, as well as elution pH conductivity, can be modified to achieve a desired distribution of product-relates substances (AR or lysine variants) For example, but not by way of limitation, certain embodiments are directed to the modulation of the lysine distribution of purified sample of a protein of interest, e.g., increasing Lys 0 and decreasing Lys 1 and Lys 2. In certain embodiments, the methods of the present invention allow for the preparation of samples wherein the amount of Lys 0 is decreased, while the amount of Lys 1 and/or Lys 2 is increased.

In certain embodiments, an AEX chromatographic separation can be performed and combinations of fractions can be pooled to achieve a combination of desired process-related impurity and/or product-relates substance levels, in addition to, or in place of merely modulating charge variant concentration.

Spectroscopy methods such as UV, NIR, FTIR, Fluorescence, and Raman may be used to monitor levels of AR species in an on-line, at-line or in-line mode, which can then be used to control the level of charge variants, e.g., acidic species, in the pooled material collected from the AEX effluent.

In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of AEX and CEX and MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, and/or UF/DF steps so as to achieve the desired AR, product quality, ion concentration, and/or viral reduction.

AEX chromatography can be used in conjunction with recycle chromatography modes and continuous chromatography modes.

Cation Exchange (CEX) Chromatography

The low AR compositions of the invention can be produced by subjecting the composition, e.g., a primary recovery sample, to at least one cation exchange separation step after the above-described displacement chromatography step. In another embodiment, the cation exchange step will occur before the above-described displacement chromatography step. In one embodiment, the cation exchange chromatography step will occur after the above-described Protein A affinity and displacement chromatography steps.

The use of a cationic exchange material versus an anionic exchange material, such as those anionic exchange materials discussed in detail above, is based on the local charges of the protein of interest in a given solution. Therefore, it is within the scope of this invention to employ a cationic exchange step prior to the use of an anionic exchange step, or an anionic exchange step prior to the use of a cationic exchange step. Furthermore, it is within the scope of this invention to employ only a cationic exchange step, only an anionic exchange step, or any serial combination of the two (including serial combinations of one or both ion exchange steps with the other chromatographic separation technologies described herein).

In performing the separation, the initial protein mixture can be contacted with the cation exchange material by using any of a variety of techniques, e.g., using a batch purification technique or a chromatographic technique, as described above in connection with Protein A or AEX.

In certain embodiments, the aqueous salt solution used as both the loading and wash buffer has a pH that is lower than the isoelectric point (pI) of the protein of interest. In certain embodiments, the pH is about 0 to 5 units lower than the pI of the protein. In certain embodiments, it is in the range of 1 to 2 units lower. In certain embodiments, it is in the range of 1 to 1.5 units lower.

In certain embodiments, the concentration of the anionic agent in aqueous salt solution is increased or decreased to achieve a pH of between about 3.5 and 10.5, or between about 4 and 10, or between about 4.5 and 9.5, or between about 5 and 9, or between about 5.5 and 8.5, or between about 6 and 8, or between about 6.5 and 7.5. In certain embodiments, the concentration of anionic agent is increased or decreased in the aqueous salt solution to achieve a pH of 5, or 5.5, or 6, or 6.5, or 6.8, or 7.5. Buffer systems suitable for use in the CEX methods include, but are not limited to, tris formate, tris acetate, ammonium sulfate, sodium chloride and sodium sulfate.

In certain embodiments, the conductivity and pH of the aqueous salt solution is adjusted by increasing or decreasing the concentration of a cationic agent. In certain embodiments, the cationic agent is maintained at a concentration of between about range of 20 mM to 500 mM, or between about 50 to 350 mM or between about 100 to 300 mM or between about 100 to 200 mM.

In certain non-limiting embodiments, the cationic agent is selected from the group consisting of sodium, Tris, tromethalmine, ammonium, arginine, or combinations thereof. In certain non-limiting embodiments, the anionic agent is selected from the group consisting of formate, acetate, citrate, chloride anion, sulphate, phosphate or combinations thereof.

A packed cation-exchange chromatography column or a cation-exchange membrane device can be operated either in bind-elute mode, flow-through mode, or a hybrid mode wherein the product exhibits binding to the chromatographic material, yet can be washed from the column using a buffer that is the same or substantially similar to the loading buffer. The details of these modes are outlined above.

Cationic substituents include carboxymethyl (CM), sulfoethyl (SE), sulfopropyl (SP), phosphate (P) and sulfonate (S). Additional cationic materials include, but are not limited to: Capto SP ImpRes, which is a high flow agarose bead; CM Hyper D grade F; which is a ceramic bead coated and permeated with a functionalized hydrogel, 250-400 ionic groups µeq/mL; Eshmuno S, which is a hydrophilic polyvinyl ether base matrix with 50-100 µeq/mL ionic capacity; Nuvia C Prime, which is a hydrophobic cation exchange media composed of a macroporous highly cross-linked hydrophilic polymer matrix 55-75 µeq/mL; Nuvia S, which has a UNOsphere base matrix with 90-150 µeq/mL ionic groups; Poros HS; which is a rigid polymetic bead with a backbone consisting of cross-linked poly[styrene-divinyl-benzene]; Poros XS; which is a rigid polymetic bead with a backbone consisting of cross-linked poly[styrene-divinyl-benzene]; Toyo Pearl Giga Cap CM 650M, which is a polymeric base bead with 0.225 meq/mL ionic capacity; Toyo Pearl Giga Cap S 650M which is a polymeric base bead; Toyo Pearl MX TRP, which is a polymeric base bead. Detailed information concerning the aforementioned materials is listed in Table B. It is noted that CEX chromatography can be used with MM resins, described herein.

TABLE B

Cationic Materials

| Resin | Vendor | Type | Particle Size | Catalog Number |
|---|---|---|---|---|
| Capto SP ImpRes | GE | Strong | ~40 μm | 17-5468-10 |
| CM Hyper D | Pall | Weak | ~50 μm | 20050-027 |
| Eshmuno S | Millipore | Strong | ~85 μm | 1.20078 |
| Nuvia C Prime | Biorad | Mix Mode | ~70 μm | 156-3401 |
| Nuvia S | Biorad | Strong | ~85 μm | 156-0315 |
| Poros HS | Applied Biosystems | Weak | ~50 μm | 13359-06 |
| Poros XS | Applied Biosystems | Strong | ~50 μm | 4404337 |
| Toyo Pearl Giga Cap CM 650M | Tosoh | Weak | ~75 μm | 21946 |
| Toyo Pearl Giga Cap S 650M | Tosoh | Strong | ~75 μm | 21833 |
| Toyo Pearl MX Trp 650M | Tosoh | Mix Mode | ~75 μm | 22817 |

In certain embodiments, the protein load of the mixture comprising protein of interest is adjusted to a total protein load to the column of between about 5 and 150 g/L, or between about 10 and 100 g/L, between about 20 and 80 g/L, between about 30 and 50 g/L, or between about 40 and 50 g/L. In certain embodiments, the protein concentration of the load protein mixture is adjusted to a protein concentration of the material loaded to the column of about 0.5 and 50 g/L, or between about 1 and 20 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the methods of the instant invention can be used to selectively remove, significantly reduce, or essentially remove all of AR in the Flow Through and wash fractions while enriching for the same in the elution fraction, thereby producing protein compositions that have reduced AR or are free of AR. In certain embodiments relating to the purification of adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments relating to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including, but not limited to those relating to adalimumab, the methods of the instant invention can be used to selectively remove, significantly reduce, or essentially remove all of the MGO variants in the elution fractions while enriching for the same in the Flow Through and wash fractions, thereby producing protein preparations with reduced or free of MGO variants. In certain embodiments, including, but not limited to those relating to adalimumab, the methods of the instant invention can be used to selectively remove, significantly reduce, or essentially remove all of the glycated variants (Schiff's base and permanently glycated forms) in the elution fractions while enriching for the same in the Flow Through and wash fractions, thereby producing protein preparations with reduced or free of glycated variants.

In certain embodiments, the loading, pH, conductivity of the CEX chromatography step, as well as elution pH conductivity, can be modified to achieve a desired distribution of acidic species. For example, but not by way of limitation, certain embodiments are directed to the modulation of the lysine distribution of a purified sample of a protein of interest, e.g., increasing Lys 0 and decreasing Lys 1 and Lys 2. In certain embodiments, the methods of the present invention allow for the preparation of samples wherein the amount of Lys 0 is decreased, while the amount of Lys 1 and/or Lys 2 is increased.

In certain embodiments, a CEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of product-related charge variants, aggregates, low molecular weight variants (e.g., fragments of the protein of interest) in an on-line, at-line or in-line mode, which can then be used to control the level of charge variants, e.g., acidic species, in the pooled material collected from the CEX effluent. In certain embodiments, specific signals arising from the chemical modification of the proteins such as glycation, MGO modification, deamidation, glycosylation may be specifically measurable by spectroscopic methods through such in-line, on-line or at-line methods, enabling realtime or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of CEX and AEX and/or MM methods can be used to prepare product-related substance-modulated materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional chromatography, filtration, pH adjustment, UF/DF steps so as to achieve the desired product quality, AR, ion concentration, and/or viral reduction.

CEX chromatography can be used in conjunction with recycle chromatography and continuous chromatography modes.

Mixed Mode Chromatography

Mixed mode ("MM") chromatography may also be used to prepare the low AR compositions of the invention. MM chromatography, also referred to herein as "multimodal chromatography", is a chromatographic strategy that utilizes a support comprising a ligand that is capable of providing at least two different, and in certain embodiments co-operative, sites that interact with the substance to be bound. In certain embodiments, one of these sites gives an attractive type of charge-charge interaction between the ligand and the substance of interest and the other site provides for electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc.

In certain embodiments, the resin employed for a mixed mode separation is Capto Adhere. Capto Adhere is a strong anion exchanger with multimodal functionality. Its base matrix is a highly cross-linked agarose with a ligand (N-Benzyl-N-methyl ethanol amine) that exhibits many functionalities for interaction, such as ionic interaction, hydrogen bonding and hydrophobic interaction. In certain embodiments, the resin employed for a mixed mode separation is selected from PPA-HyperCel and HEA-HyperCel. The base matrices of PPA-HyperCel and HEA-HyperCel are high porosity cross-linked cellulose. Their ligands are Phenylpropylamine and Hexylamine, respectively. Phenylpropylamine and Hexylamine offer different selectivity and hydrophobicity options for protein separations. Additional mixed mode chromatographic supports include, but are not limited to, Nuvia C Prime, Toyo Pearl MX Trp 650M, and Eshmuno® HCX.

In certain embodiments, the mixed mode chromatography resin is comprised of ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

In certain embodiments, the protein load of the mixture comprising protein of interest is adjusted to a total protein load to the column of between about 50 and 750 g/L, or between about 75 and 500 g/L, or between about 100 and 300 g/L. In certain embodiments, the protein concentration of the load protein mixture is adjusted to a protein concentration of the material loaded to the column of about 1 and 50 g/L, or between about 9 and 25 g/L.

In certain embodiments, additives such as poly ethylene glycol, detergents, amino acids, sugars, chaotropic agents can be added to enhance the performance of the separation, so as to achieve better recovery or product quality.

In certain embodiments, including, but not limited to those relating to adalimumab, the MM methods of the instant invention can be used to selectively remove, significantly reduce, or essentially remove all of AR in the Flow Through and wash fractions while enriching for the same in the flow elution fraction, thereby producing protein compositions that have reduced AR or are free of AR. In certain embodiments relating to the purification of adalimumab, the methods of the instant invention can be used to selectively remove, significantly reduce, or essentially remove all of AR1 charge variants in the Flow Through and wash fractions while enriching for the same in the flow elution fraction, thereby producing protein compositions that have reduced AR1 or are free of AR1 variants. In certain embodiments relating to adalimumab, the methods of the instant invention can be used to selectively remove, significantly reduce, or essentially remove all of AR2 charge variants in the flow-through and wash fractions while enriching for the same in the flow elution fraction, thereby producing protein compositions that have reduced AR2 or are free of AR2 variants.

In certain embodiments, including, but not limited to those relating to adalimumab, the MM methods of the instant invention can be used to selectively remove, significantly reduce, or essentially remove all of the MGO variants in the Flow Through and wash fractions while enriching for the same in the elution fraction, thereby producing protein preparations with reduced or free of MGO variants. In certain embodiments, including, but not limited to those relating to adalimumab, the methods of the instant invention can be used to selectively remove, significantly reduce, or essentially remove all of the glycated variants (Schiff's base and permanently glycated forms) in the Flow Through and wash fractions while enriching for the same in the elution fraction, thereby producing protein preparations with reduced or free of glycated variants.

In certain embodiments, the loading, pH, conductivity of the MM chromatography step, wash pH and conductivity, as well as elution pH conductivity, can be modified to achieve a desired distribution of acidic species. For example, but not by way of limitation, certain embodiments are directed to the modulation of the lysine distribution of a purified sample of a protein of interest, e.g., increasing Lys 0 and decreasing Lys 1 and Lys 2. In certain embodiments, the methods of the present invention allow for the preparation of samples wherein the amount of Lys 0 is decreased, while the amount of Lys 1 and/or Lys 2 is increased.

In certain embodiments, a MM chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of AR species in an on-line, at-line or in-line mode, which can then be used to control the level of charge variants, e.g., acidic species, in the pooled material collected from the MM effluent. In certain embodiments, specific signals arising from the chemical modification of the proteins such as glycation, MGO modification, deamidation, glycosylation may be specifically measurable by spectroscopic methods through such in-line, on-line or at-line methods, enabling real time or near-real time control of product quality of the resulting product. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of mixed mode and AEX and CEX methods can be used to prepare the low AR compositions of the invention, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, AR, ion concentration, and/or viral reduction.

MM chromatography can be used in conjunction with recycle chromatography and continuous chromatography modes.

Continuous and Recycle Chromatography

Continuous and recycle chromatography modes can be used to produce the low AR compositions of the invention, and are described below. These methods result in significant improvements in recovery of the protein, e.g., antibody, of interest while maintaining the AR reduction levels. These continuous and recycle chromatography modes are applicable to chromatography methods where (a) the low acidic species component of interest is collected in the unbound fraction during the chromatography (Flow Through/wash chromatography) or (b) where the low acidic species component of interest is first bound to the media and subsequently recovered by washing the media with conditions that elute the bound component.

Continuous and Recycle Chromatography—Flow Through/Wash Chromatography

In the case where the low acidic species component of interest is collected in the unbound fraction, the following approach is employed which prevents loss of the material loaded on the column.

In one embodiment, a recycle chromatography mode is used wherein the column is loaded and the unbound fractions that results in the target AR level are collected. Subsequently, instead of regenerating the column and losing the product, the column is washed under conditions that result in recovery of the product remaining bound to the column. This product recovered under these conditions contains significantly higher AR levels than the original feed material. This wash fraction is adjusted to the appropriate conditions to achieve the separation desired on subsequent processing (typically similar conditions to the initial preparation) and combined with the original feed material and loaded on the column again (after preparing the column appropriately for the next cycle). The amount of material prepared for the next cycle, combining the wash fraction from the first cycle and the fresh material is adjusted to the target loading capacity for the column to achieve the desired separation (typically similar to the capacity targeted for the first cycle).

In performing the second cycle, a similar strategy is employed, collecting the unbound fraction so as to achieve the target AR level and then subsequently washing the column under conditions to recover the product remaining on the column.

In one embodiment, this recycle chromatography mode is continued until all the load materials are used. The number of cycles can be controlled by designing the column size appropriately.

In employing the recycle chromatography mode, the recovery of the product loaded on the column is significantly improved while achieving the target AR levels.

Several variations of the recycle chromatography mode can be employed. In one embodiment, the fractions that are collected targeting a certain AR level can be determined based on predetermined criteria or based on at-line, off-line or on-line analysis of the effluent of the column or the collected pool.

In another embodiment, the wash conditions used for the first cycle can be adjusted to recover the desired amount of product at the desired product quality, only limited by the feasibility of preparing an appropriate load mixture for the subsequent step. In one aspect of this embodiment, the wash condition may be similar to the load condition. In another aspect of this embodiment, the wash condition can be stringent to recover all of the product species (desired and undesired) remaining on the column.

In still another embodiment, the loading amount, the loading conditions and the washing conditions used for the subsequent cycles can be modified to achieve the desired purity, given that that loading material for the subsequent cycles are likely to contain higher levels of AR.

In another embodiment, the last cycle of the operation can be performed under different conditions such that the target purity and target recovery can be achieved to optimize overall recovery and purity.

The methods for producing the low AR composition of the invention can also be implemented in a continuous chromatography mode. In this mode, at least two columns are employed (referred to as a "first" column and a "second" column). In one embodiment, the feed material is loaded onto the first column, and the unbound fraction from the first column is collected such that the pool material contains the target AR level. The column is then washed under conditions that recover the remaining product. This material is then dynamically diluted with appropriate solutions to achieve the desired loading conditions, mixed with fresh feed material and directed to the second column. The unbound fraction from the second column is collected to achieve the target AR level. The second column is then washed under conditions to recover the product and diluted with appropriate solutions, mixed with fresh materials dynamically and directed to the first column (which is prepared to receive the load after regeneration/cleaning). In one embodiment, this cycling is continued until all the load material is used. The last cycle can be operated in a "typical" mode, with appropriate adjustments to the load and wash conditions as necessary.

In certain embodiments this continuous chromatography mode can be carried out such that the wash material containing the higher AR levels can be directed back into the load tank after appropriate dilution. This material can then be loaded subsequently or concurrently onto the second column, such that the operation of the two columns are not in tandem, reducing complexity of the operation.

This continuous chromatography mode, while similar to the recycle chromatography mode, can be carried out more efficiently, and therefore has a reduced processing time.

For this continuous chromatography mode, several variations can be employed. In one embodiment, the fractions that are collected targeting a certain AR level can be determined based on predetermined criteria or based on at-line, off-line or on-line analysis of the effluent of the column or the collected pool.

In another embodiment, the wash conditions used for the first cycle can be adjusted to recover the desired amount of product at the desired product quality, only limited by the feasibility of preparing an appropriate load mixture for the subsequent step. In one aspect of this embodiment, the wash conditions may be similar to the load conditions. In another aspect of the embodiment, the wash conditions can be stringent to recover all of the product species (desired and undesired) remaining on the column.

In still another embodiment, the loading amount, the loading conditions and the washing conditions used for the subsequent cycles can be modified to achieve the desired purity, given that that loading material for the subsequent cycles are likely to contain higher levels of AR.

In another embodiment, the last cycle of the operation can be performed under different conditions such that the target purity/recovery can be achieved to optimize overall recovery and and/or purity.

In one embodiment, the media choice for the recycle or continuous modes can be one of many chromatographic resins with pendant hydrophobic and anion exchange functional groups, monolithic media, membrane adsorbent media or depth filtration media.

In certain embodiments, membrane or depth filter based media ("convective media") can be used in the recycle or continuous chromatography modes because selectivity of separation is not required to be high given the fact that the less enriched portions of the product are "recycled" while the pure fractions are selectively pooled.

Continuous and Recycle Chromatography—Elution Chromatography

In the elution mode of chromatography or separation, as exemplified by the CEX technology for AR reduction, the conditions are chosen for the load and wash steps such that the AR enriched material is collected in the Flow Through and/or wash fractions, while the AR reduced material is collected in the elution fraction. In the typical implementation of the CEX technology, about 10 to 40% of the product (the desired charge variant) may be lost in the Flow Through/Wash fractions. Two modes of operation, namely the recycle chromatography mode and the continuous chromatography mode provide improved recovery, while maintaining the target AR levels.

In the recycle chromatography mode, the load material is, in general, processed over multiple cycles. In implementing the recycle chromatography mode, the load material is prepared such that the eluate contains the target product purity or AR level. Under these conditions, the AR enriched material is collected in the Flow Through/wash fractions. This material is pooled and additional fresh load material is added to achieve the appropriate loading capacity for the next cycle of chromatography on the same column. In particular, in one embodiment, the column is eluted under conditions where the bound product (having low AR levels) is recovered, and subsequently regenerated and equilibrated to prepare for the next cycle.

In the next cycle, the combined load (Flow Through/wash from cycle 1 above, as well as fresh material) is loaded to the target capacity. The Flow Through/wash fractions are collected and pooled. The column is eluted to obtain the second eluate, again containing the target low AR composition. In one embodiment, this sequence is continued until all the load materials are processed.

In another embodiment, by implementing the recycle chromatography mode, the material that would otherwise be discarded as AR enriched material is further purified to "recover" pure protein product, thereby improving the overall recovery of the protein. In one embodiment, the level of recovery depends on the number of cycles employed.

For the recycle chromatography mode, several variations can be employed. In one embodiment, the entire pool of the Flow Through/wash fractions are preferably combined with fresh materials to maximize recovery of the entire operation. However, a portion of the flow through wash can be discarded to achieve higher purity or efficiency. For example, in one embodiment, certain fractions containing very high levels of AR species can be discarded. To enable such selective pooling, off-line, in-line or at line methods can be used to directly or indirectly measure the levels of AR.

In another embodiment, the loading amount and the conditions for loading, washing and eluting can be modified for the second and subsequent cycles to accommodate the higher levels of AR that will be present in the loading pool.

In still another embodiment, the last cycle of the method can be performed under conditions such that the target purity and recovery can be achieved to optimize overall recovery and purity.

A continuous chromatography mode provides additional advantages in terms of time efficiency. In this mode of operation, two or more columns are used. Specifically, as with the recycle mode, an appropriate condition for the load capacity, load, wash and elution conditions are chosen for the operation. The Flow Through and wash fractions (or a portion thereof) is directed to the load tank containing the fresh material. After completion of the load and wash steps, the first column is eluted and subsequently regenerated. Meanwhile, the second column is loaded with the material that is a mix of fresh material and the wash and Flow Through from the previous cycle. The wash and Flow Through from the second column is again directed back to the load tank. The second column is then eluted and regenerated. The first column is then ready to be loaded and the cycle continues. This continuous chromatography mode is efficient as the product is processed continuously and the purified product is obtained in a semi-continuous manner.

Several variations of the continuous chromatography mode can be employed. In one embodiment, the entire pool of the Flow Through/wash fractions is combined with fresh materials to maximize recovery of the entire operation. However, a portion of the Flow Through wash can be discarded to achieve higher purity or efficiency. For example, certain fractions containing very high levels of AR species can be discarded. To enable such selective pooling, off-line, in-line or at line methods can be used to measure directly or indirectly the levels of acidic species.

In another embodiment, the loading amount, conditions for loading, washing and eluting can be modified for the second and subsequent cycles to accommodate the higher levels of AR that will be present in the loading pool.

In still another embodiment, the last cycle of the operation can be performed under different conditions to optimize overall recover and purity.

The recycle chromatography mode and the continuous chromatography mode are not limited to use with any particular chromatography resin. The media used for the recycle or continuous modes can be one of many chromatographic resins with pendant hydrophobic and anion exchange functional groups, monolithic media, membrane adsorber media or depth filtration media.

In certain embodiments, membrane depth filter-based media ("convective media") can be used with the recycle or continuous modes as the selectivity of separation is not required to be high given the fact that the less enriched portions of the product are "recycled" while the pure fractions are selectively pooled.

Recycle chromatography mode and the continuous chromatography mode can be used in conjunction with AEX, CEX, or MM chromatography methods, as described herein, to produce the low AR compositions of the invention.

Hydrophobic Interaction Chromatography

The low AR compositions of the invention may also be prepared using a hydrophobic interaction chromatography (HIC) step in addition to the displacement chromatography step.

In performing the separation, the sample mixture is contacted with the HIC material, e.g., using a batch purification technique or using a column or membrane chromatography. Prior to HIC purification it may be desirable to adjust the concentration of the salt buffer to achieve desired protein binding to the resin or the membrane.

Whereas ion exchange chromatography relies on the local charge of the protein of interest for selective separation, hydrophobic interaction chromatography employs the hydrophobic properties of the proteins to achieve selective separation. Hydrophobic groups on the protein interact with hydrophobic groups of the resin or the membrane. The more hydrophobic a protein is the stronger it will interact with the column or the membrane. Thus the HIC step removes process-related impurities (e.g., HCPs) as well as product-related substances (e.g., aggregates and fragments).

Like ion exchange chromatography, a HIC column or membrane device can also be operated in product a bind-elute mode, a flow-through, or a hybrid mode wherein the product exhibits binding to the chromatographic material, yet can be washed from the column using a buffer that is the same or substantially similar to the loading buffer. The details of these modes are outlined above in connection with AEX purification.

As hydrophobic interactions are strongest at high ionic strength, this form of separation is conveniently performed following salt elution step, such as those that are typically used in connection with ion exchange chromatography. Alternatively, salts can be added into a low salt level feed stream before this step. Adsorption of the antibody to a HIC column is favored by high salt concentrations, but the actual concentrations can vary over a wide range depending on the nature of the protein of interest, salt type and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH_3CO_3^-$; $Cl^-$; $Br^-$; $NO_3^-$; $ClO_4^-$; $I^-$; $SCN^-$.

In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4$>$Na_2SO_4$>$NaCl$>$NH_4Cl$>$NaBr$>$NaSCN$. In general, salt concentrations of between about 0.75 M and about 2 M ammonium sulfate or between about 1 and 4 M NaCl are useful.

HIC media normally comprise a base matrix (e.g., cross-linked agarose or synthetic copolymer material) to which hydrophobic ligands (e.g., alkyl or aryl groups) are coupled. A suitable HIC media comprises an agarose resin or a membrane functionalized with phenyl groups (e.g., a Phenyl Sepharose™ from GE Healthcare or a Phenyl Membrane from Sartorius). Many HIC resins are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (Bio-Rad, California); WP HI-Propyl (C3)™ (J. T. Baker, New Jersey); and Toyopearl™ ether, phenyl or butyl (TosoHaas, PA).

Viral Filtration

Viral filtration is a dedicated viral reduction step in the entire purification process. This step is usually performed post chromatographic polishing steps. Viral reduction can be achieved via the use of suitable filters including, but not limited to, Planova 20N™, 50 N or BioEx from Asahi Kasei Pharma, Viresolve™ filters from EMD Millipore, ViroS art CPV from Sartorius, or Ultipor DV20 or DV50™ filter from Pall Corporation. It will be apparent to one of ordinary skill in the art to select a suitable filter to obtain desired filtration performance.

Ultrafiltration/Diafiltration

Certain embodiments of the present invention employ ultrafiltration and diafiltration steps to further concentrate and formulate the protein of interest, e.g., an antibody product, in addition to the displacement chromatography steps. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter membrane pores while proteins, such as antibodies, are retained above the membrane surface.

Diafiltration is a method of using membrane filters to remove and exchange salts, sugars, and non-aqueous solvents, to separate free from bound species, to remove low molecular-weight species, and/or to cause the rapid change of ionic and/or pH environments. Microsolutes are removed most efficiently by adding solvent to the solution being diafiltered at a rate approximately equal to the permeate flow rate. This washes away microspecies from the solution at a constant volume, effectively purifying the retained protein of interest. In certain embodiments of the present invention, a diafiltration step is employed to exchange the various buffers used in connection with the instant invention, optionally prior to further chromatography or other purification steps, as well as to remove impurities from the protein preparations.

One of ordinary skill in the art can select appropriate membrane filter device for the UF/DF operation. Examples of membrane cassettes suitable for the present invention include, but not limited to, Pellicon 2 or Pellicon 3 cassettes with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

Exemplary Purification Strategies

In certain embodiments, primary recovery can proceed by sequentially employing pH reduction, centrifugation, and filtration steps to remove cells and cell debris (including HCPs) from the production bioreactor harvest. In certain embodiments, the present invention is directed to subjecting a sample mixture from said primary recovery to Protein A affinity followed by displacement chromatography. Certain embodiments of the present invention will include further purification steps. Examples of additional purification procedures which can be performed prior to, during, or following the displacement chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

Specific examples of such combinations of strategies is presented below, with specific data relating to particular combinations useful in the context of the instant invention included in Examples 1-8 and in Tables 80-87 and 76-78 of U.S. Provisional Application No. 61/893,068, entitled "Low Acidic Species Compositions and Methods for Producing and Using the Same", filed on Oct. 18, 2013, the entire contents of which are expressly incorporated herein by reference.

In certain embodiments, the unbound Flow Through and wash fractions can be further fractionated and a combination of fractions providing a target product purity can be pooled.

In certain embodiments, the protein concentration can be adjusted to achieve a differential partitioning behavior between the antibody product and the product-related substances, such that the purity and/or yield can be further improved. In certain embodiments, the loading can be performed at different protein concentrations during the loading operation to improve the product quality/yield of any particular purification step.

In certain embodiments, the column temperature can be independently varied to improve the separation efficiency and/or yield of any particular purification step.

In certain embodiments, the loading and washing buffer matrices can be different or composed of mixtures of chemicals, while achieving similar "resin interaction" behavior such that the above novel separation can be effected. For example, but not by way of limitation, the loading and washing buffers can be different, in terms of ionic strength or pH, while remaining substantially similar in function in terms of the washout of the product achieved during the wash step. In certain embodiments, additives such as amino acids, sugars, PEG, etc can be added to the load or wash steps to modulate the partitioning behavior to achieve the separation efficiency and/or yield.

In certain embodiments, the loading & washing steps can be controlled by in-line, at-line or off-line measurement of the product related impurity/substance levels, either in the column effluent, or the collected pool or both, so as to achieve the target product quality and/or yield. In certain embodiments, the loading concentration can be dynamically controlled by in-line or batch or continuous dilutions with buffers or other solutions to achieve the partitioning necessary to improve the separation efficiency and/or yield.

IV. Methods of Assaying Sample Purity

Assaying Host Cell Protein

The present invention also provides methods for determining the residual levels of host cell protein (HCP) concentration in the low AR compositions of the invention. As described above, HCPs are desirably excluded from the final target substance product. Exemplary HCPs include proteins originating from the source of the antibody production. Failure to identify and sufficiently remove HCPs from the target antibody may lead to reduced efficacy and/or adverse reactions in a subject.

As used herein, the term "HCP ELISA" refers to an ELISA where the second antibody used in the assay is specific to the HCPs produced from cells, e.g., CHO cells, used to generate the antibody of interest. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HCPs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

Assaying Acidic Species (AR)

The levels of acidic species in the chromatographic samples produced using the techniques described herein may be analyzed as described in the Examples section. In certain embodiments a CEX-HPLC method is employed. For example, but not by way of limitation, cation exchange chromatography can be performed on a Dionex ProPac WCX-10, Analytical column 4 mm×250 mm (Dionex, CA).

An Agilent 1200 HPLC system can then be used as the HPLC. In certain embodiments, mobile phases such as 10 mM Sodium Phosphate dibasic pH 7.5 (Mobile phase A) and 10 mM Sodium Phosphate dibasic, 500 mM Sodium Chloride pH 5.5 (Mobile phase B) can be used. In certain embodiments, a binary gradient (94% A, 6% B: 0-20 min; 84% A, 16% B: 20-22 min; 0% A, 100% B: 22-28 min; 94% A, 6% B: 28-34 min) can be used with detection at 280 nm. In certain embodiments, quantitation is based on the relative area percent of detected peaks. In certain embodiments, the peaks that elute at relative residence time less than a certain time are together represented as the acidic peaks.

Assaying Size Variants

In certain embodiments, the levels of aggregates, monomer, and fragments in the chromatographic samples produced using the techniques described herein are analyzed. In certain embodiments, the aggregates, monomer, and fragments are measured using a size exclusion chromatographic (SEC) method for each molecule. For example, but not by way of limitation, a TSK-gel G3000SW×L, 5 µm, 125 Å, 7.8×300 mm column (Tosoh Bioscience) can be used in connection with certain embodiments, while a TSK-gel Super SW3000, 4 µm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

Any additional technique, such as mass spectroscopy, can be used for assaying size variants.

V. Methods of Treatment Using the Low AR Compositions of the Invention

The low AR compositions of the invention may be used to treat any disorder in a subject for which the therapeutic protein comprised in the composition is appropriate for treating. \

A "disorder" is any condition that would benefit from treatment with the protein. This includes chronic and acute disorders or diseases including those pathological conditions which predispose the subject to the disorder in question. In the case of an anti-TNFα antibody, or antigen binding portion thereof, such as adalimumab, a therapeutically effective amount of the low AR composition may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the low AR compositions or a low process-related impurity compositions of the invention may be used to treat an autoimmune disease, such as rheumatoid arthritis, juvenile idiopathic arthritis, or psoriatic arthritis, an intestinal disorder, such as Crohn's disease or ulcerative colitis, a spondyloarthropathy, such as ankylosing spondylitis, or a skin disorder, such as psoriasis.

Disorders in which TNFα activity is detrimental are well known in the art and described in detail in U.S. Pat. No. 8,231,876 and U.S. Pat. No. 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina, and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, cardiomyopathy, coronary artery spasm, coronary artery disease, valvular disease, arrhythmias, and cardiomyopathies), spondyloarthropathies (including ankylosing spondylitis, psoriatic arthritis/spondylitis, enteropathic arthritis, reactive arthritis or Reiter's syndrome, and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis), hepatic disorders (including hepatitis, alcoholic hepatitis, viral hepatitis, alcoholic cirrhosis, a1 antitypsin deficiency, autoimmune cirrhosis, cryptogenic cirrhosis, fulminant hepatitis, hepatitis B and C, and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), pemphigus vulgaris, scleroderma, atopic dermatitis (eczema), sarcoidosis, erythema nodosum, hidradenitis suppurative, lichen planus, Sweet's syndrome, scleroderma and vitiligo), vasculitides (including Behcet's disease), and other disorders, such as juvenile rheumatoid arthritis (JRA), endometriosis, prostatitis, choroidal neovascularization, sciatica, Sjogren's syndrome, uveitis, wet macular degeneration, osteoporosis, osteoarthritis, active axial spondyloarthritis (active axSpA) and non-radiographic axial spondyloarthritis (nr-axSpA).

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering a low AR composition comprising an anti-TNFα antibody, or antigen binding portion thereof, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab, also referred to as HUMIRA®.

The low AR compositions can be administered by a variety of methods known in the art. Exemplary routes/modes of administration include subcutaneous injection, intravenous injection or infusion. In certain aspects, a low AR compositions may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a low AR composition of the invention is 0.01-20 mg/kg, or 1-10 mg/kg, or 0.3-1 mg/kg. With respect to low AR compositions comprising an anti-TNFα antibody, or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg, and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

VI. Pharmaceutical Formulations Containing the Low AR Compositions of the Invention The present invention further provides preparations and formulations comprising the low AR compositions of the invention. It should be understood that any of the antibodies and antibody fragments described herein, including antibodies and antibody fragments having any one or more of the structural and functional features described in detail throughout the application, may be formulated or prepared as described below. When various formulations are described in this section as including an antibody, it is understood that such an antibody may be an antibody or an antibody fragment having any one or more of the characteristics of the antibodies and antibody fragments described herein. In one embodiment, the antibody is an anti-TNFα antibody, or antigen-binding portion thereof.

In certain embodiments, the low AR compositions of the invention may be formulated with a pharmaceutically acceptable carrier as pharmaceutical (therapeutic) compositions, and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

The low AR compositions of the invention are present in a form known in the art and acceptable for therapeutic uses. In one embodiment, a formulation of the low AR compositions of the invention is a liquid formulation. In another embodiment, a formulation of the low AR compositions of the invention is a lyophilized formulation. In a further embodiment, a formulation of the low AR compositions of the invention is a reconstituted liquid formulation. In one embodiment, a formulation of the low AR compositions of the invention is a stable liquid formulation. In one embodiment, a liquid formulation of the low AR compositions of the invention is an aqueous formulation. In another embodiment, the liquid formulation is non-aqueous. In a specific embodiment, a liquid formulation of the low AR compositions of the invention is an aqueous formulation wherein the aqueous carrier is distilled water.

The formulations of the low AR compositions of the invention comprise an antibody in a concentration resulting in a w/v appropriate for a desired dose. The antibody may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In a specific embodiment, a formulation of the low AR compositions of the invention comprises at least about 100 mg/ml, at least about 125 mg/ml, at least 130 mg/ml, or at least about 150 mg/ml of an antibody of the invention.

In one embodiment, the concentration of antibody, which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml, or between about 25 mg/ml and about 50 mg/ml.

In a specific embodiment, a formulation of the low AR compositions of the invention comprises between about 90 mg/ml and about 110 mg/ml or between about 100 mg/ml and about 210 mg/ml of an antibody.

The formulations of the low AR compositions of the invention comprising an antibody may further comprise one or more active compounds as necessary for the particular indication being treated, typically those with complementary activities that do not adversely affect each other. Such additional active compound/s is/are suitably present in combination in amounts that are effective for the purpose intended.

The formulations of the low AR compositions of the invention may be prepared for storage by mixing the antibody having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12$^{th}$ edition, L. Brunton, et al. and Remington's Pharmaceutical Sciences, 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, MgCl$_2$, or CaCl$_2$ The formulations of the low AR compositions of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0. One of skill in the art understands that the pH of a formulation generally should not be equal to the isoelectric point of the particular antibody to be used in the formulation.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the low AR compositions of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a formulation may comprise about 10 mM, about 25 mM, or no histidine.

The formulations of the low AR compositions of the invention may comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In a specific embodiment, the formulations of the low AR compositions of the invention may comprise trehalose. In one embodiment, a formulation of the invention comprises at least about 1%, at least about 2%, at least about 4%, at least about 8%, at least about 20%, at least about 30%, or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a formulation of the invention comprises about 1%, about 2%, about 4%, about 6%, about 8%, about 15%, about 20%, about 30%, or about 40% trehalose. In a specific embodiment, a formulation of the invention comprises about 4%, about 6% or about 15% trehalose.

In certain embodiments, a formulation of the low AR compositions of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, CaCl$_2$, and MgCl$_2$. In a specific embodiment, the formulation comprises NaCl.

A formulation of the low AR compositions of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM, or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM, or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM, or about 300 mM sodium chloride.

A formulation of the low AR compositions of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM, or about 400 mM of an amino acid.

The formulations of the low AR compositions of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc.), can optionally be added to the formulations of the invention to reduce aggregation. In one embodiment, a formulation of the invention comprises Polysorbate 20, Polysorbate 40, Polysorbate 60, or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

The formulations of the low AR compositions of the invention may optionally further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of an antibody, as well known those in the art or as described herein.

In one embodiment, the low AR compositions of the invention are formulated with the same or similar excipients and buffers as are present in the commercial adalimumab (HUMIRA®) formulation, as described in the "Highlights of HUMIRA® Prescribing Information" for HUMIRA® (adalimumab) Injection (Revised January 2008) the entire contents of which are expressly incorporated herein by reference. For example, each prefilled syringe of HUMIRA®, which is administered subcutaneously, delivers 0.8 mL (40 mg) of drug product to the subject. Each 0.8 mL of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for Injection, USP. Sodium hydroxide is added as necessary to adjust pH.

It will be understood by one skilled in the art that the formulations of the low AR compositions of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonity of the formulation. Tonicity modifiers suitable for this invention include, but are not limited to, saccharides, salts and amino acids.

In certain embodiments, the formulations of the low AR compositions of the invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

The concentration of any one component or any combination of various components, of the formulations of the low AR compositions of the invention is adjusted to achieve the desired tonicity of the final formulation. For example, the ratio of the carbohydrate excipient to antibody may be adjusted according to methods known in the art (e.g., U.S. Pat. No. 6,685,940). In certain embodiments, the molar ratio of the carbohydrate excipient to antibody may be from about 100 moles to about 1000 moles of carbohydrate excipient to about 1 mole of antibody, or from about 200 moles to about 6000 moles of carbohydrate excipient to about 1 mole of antibody, or from about 100 moles to about 510 moles of carbohydrate excipient to about 1 mole of antibody, or from about 100 moles to about 600 moles of carbohydrate excipient to about 1 mole of antibody.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate, and calcium chloride. In specific embodiments, formulations of the invention comprise NaCl, MgCl$_2$, and/or CaCl$_2$. In one embodiment, concentration of NaCl is between about 75 mM and about 150 mM. In another embodiment, concentration of MgCl$_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine, and histidine.

In one embodiment the formulations of the low AR compositions of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the low AR compositions of the invention should be sterile. The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the low AR compositions of the invention is a lyophilized formulation. The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein of interest (such as an antibody of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS™; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and antibody molecules of a formulation of the invention is at least about 10, at least about 50, at least about 100, at least about 200, or at least about 300. In another embodiment, the molar ratio of a lyoprotectant (e.g., trehalose) and antibody molecules of a formulation of the invention is about 1, is about 2, is about 5, is about 10, about 50, about 100, about 200, or about 300.

A "reconstituted" formulation is one which has been prepared by dissolving a lyophilized antibody formulation in a diluent such that the antibody is dispersed in the reconstituted formulation. The reconstituted formulation is suitable for administration (e.g., parenteral administration) to a patient to be treated with the antibody and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the low AR compositions of the invention is a lyophilized formulation comprising an antibody of the invention, wherein at least about 90%, at least about 95%, at least about 97%, at least about 98%, or at least about 99% of said antibody may be recovered from a vial upon shaking said vial for 4 hours at a speed of 400 shakes per minute wherein the vial is filled to half of its volume with the formulation. In another embodiment, a formulation of the invention is a lyophilized formulation comprising an antibody of the invention, wherein at least about 90%, at least about 95%, at least about 97%, at least about 98%, or at least about 99% of the antibody may be recovered from a vial upon subjecting the formulation to three freeze/thaw cycles wherein the vial is filled to half of its volume with said formulation. In a further embodiment, a formulation of the invention is a lyophilized formulation comprising an antibody of the invention, wherein at least about 90%, at least about 95%, at least about 97%, at least about 98%, or at least about 99% of the antibody may be recovered by reconstituting a lyophilized cake generated from said formulation.

In one embodiment, a reconstituted liquid formulation may comprise an antibody at the same concentration as the pre-lyophilized liquid formulation.

In another embodiment, a reconstituted liquid formulation may comprise an antibody at a higher concentration than the pre-lyophilized liquid formulation, e.g., about 2 fold, about 3 fold, about 4 fold, about 5 fold, about 6 fold, about 7 fold, about 8 fold, about 9 fold, or about 10 fold higher concentration of an antibody than the pre-lyophilized liquid formulation.

In yet another embodiment, a reconstituted liquid formulation may comprise an antibody of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of an antibody than the pre-lyophilized liquid formulation.

The pharmaceutical formulations of the low AR compositions of the invention are typically stable formulations, e.g., stable at room temperature.

The terms "stability" and "stable" as used herein in the context of a formulation comprising an antibody of the invention refer to the resistance of the antibody in the formulation to aggregation, degradation or fragmentation under given manufacture, preparation, transportation and storage conditions. The "stable" formulations of the invention retain biological activity under given manufacture, preparation, transportation and storage conditions. The stability of the antibody can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of an antibody of the invention in PBS.

Therapeutic formulations of the low AR compositions of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic effect to be achieved, and (b) the limitations inherent in the art of compounding such an antibody for the treatment of sensitivity in individuals.

Therapeutic compositions of the low AR compositions of the invention can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. By way of example, in certain embodiments, the antibodies (including antibody fragments) are formulated for intravenous administration. In certain other embodiments, the antibodies (including antibody fragments) are formulated for local delivery to the cardiovascular system, for example, via catheter, stent, wire, intramyocardial delivery, intrapericardial delivery, or intraendocardial delivery.

Formulations of the low AR compositions of the invention which are suitable for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required (U.S. Pat. Nos. 7,378,110; 7,258,873; 7,135,180; 7,923,029; and US Publication No. 2004-0042972 and 2004-0042971).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the low AR compositions of the invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In certain embodiments, antibodies of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant Protein A receptor (Briscoe et al. (1995) Am. J. Physiol. 1233:134), different species of which may comprise the formulations of the invention, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the antibodies of the invention may be delivered locally to the brain to mitigate the risk that the blood brain barrier slows effective delivery.

In certain embodiments, the low AR compositions of the invention may be administered with medical devices known in the art. For example, in certain embodiments an antibody or antibody fragment is administered locally via a catheter, stent, wire, or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The efficient dosages and the dosage regimens for the low AR compositions of the invention depend on the disease or condition to be treated and can be determined by the persons skilled in the art. One of ordinary skill in the art would be able to determine such amounts based on such factors as the subject's size, the severity of the subject's symptoms, and the particular composition or route of administration selected.

VII. Alternative Formulations Containing the Low AR Compositions of the Invention a. Aqueous Formulations The invention also provides a low AR composition formulated as an aqueous formulation comprising a protein and water, as described in U.S. Pat. No. 8,420,081 and PCT Publication No. WO2012/065072, the contents of which are hereby incorporated by reference. In these aqueous formulations, the protein is stable without the need for additional agents. This aqueous formulation has a number of advantages over conventional formulations in the art, including stability of the protein in water without the requirement for additional excipients, increased concentrations of protein without the need for additional excipients to maintain solubility of the protein, and low osmolality. These also have advantageous storage properties, as the proteins in the formulation remain stable during storage, e.g., stored as a liquid form for more than 3 months at 7° C. or freeze/thaw conditions, even at high protein concentrations and repeated freeze/thaw processing steps. In one embodiment, formulations described herein include high concentrations of proteins such that the aqueous formulation does not show significant opalescence, aggregation, or precipitation.

In one embodiment, an aqueous low AR composition comprising a protein, e.g., an antibody, e.g., an anti-TNFα antibody or antigen biding portion thereof, and water is provided, wherein the formulation has certain characteristics, such as, but not limited to, low conductivity, e.g., a conductivity of less than about 2.5 mS/cm, a protein concentration of at least about 10 µg/mL, an osmolality of no more than about 30 mOsmol/kg, and/or the protein has a molecular weight (Mw) greater than about 47 kDa. In one embodiment, the formulation has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized, or spray-dried.

In one embodiment, the formulation has a low conductivity, including, for example, a conductivity of less than about 2.5 mS/cm, a conductivity of less than about 2 mS/cm, a conductivity of less than about 1.5 mS/cm, a conductivity of less than about 1 mS/cm, or a conductivity of less than about 0.5 mS/cm.

In another embodiment, low AR compositions included in the formulation have a given concentration, including, for example, a concentration of at least about 1 mg/mL, at least about 10 mg/mL, at least about 50 mg/mL, at least about 100 mg/mL, at least about 150 mg/mL, at least about 200 mg/mL, or greater than about 200 mg/mL. In another embodiment, the formulation of the invention has an osmolality of no more than about 15 mOsmol/kg.

The aqueous formulations described herein do not rely on standard excipients, e.g., a tonicity modifier, a stabilizing agent, a surfactant, an anti-oxidant, a cryoprotectant, a bulking agent, a lyoprotectant, a basic component, and an acidic component. In other embodiments of the invention, the formulation contains water, one or more proteins, and no ionic excipients (e.g., salts, free amino acids).

In certain embodiments, the aqueous formulation as described herein comprise a low AR composition comprising a protein concentration of at least 50 mg/mL and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg, and also have a high protein concentration, e.g., the concentration of the protein is at least 100 mg/mL, and may be as much as 200 mg/mL or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation as described herein is not limited by the protein size and the formulation may include any size range of proteins.

Included within the scope of the invention is an aqueous formulation comprising at least 40 mg/mL and as much as 200 mg/mL or more of a protein, for example, 40 mg/mL, 65 mg/mL, 130 mg/mL, or 195 mg/ml, which may range in size from 5 kDa to 150 kDa or more. In one embodiment, the protein in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation as described herein may be characterized by the hydrodynamic diameter ($D_h$) of the proteins in solution. The hydrodynamic diameter of the protein in solution may be measured using dynamic light scattering (DLS), which is an established analytical method for determining the $D_h$ of proteins. Typical values for monoclonal antibodies, e.g., IgG, are about 10 nm. Low-ionic formulations may be characterized in that the $D_h$ of the proteins are notably lower than protein formulations comprising ionic excipients. It has been discovered that the $D_h$ values of antibodies in aqueous formulations made using the diafiltration/ultrafiltration (DF/UF) process, as described in U.S. Pat. No. 8,420,081 and PCT Publication No. WO2012/065072, using pure water as an exchange medium, are notably lower than the $D_h$ of antibodies in conventional formulations independent of protein concentration. In one embodiment, antibodies in the aqueous formulation as described herein have a $D_h$ of less than 4 nm, or less than 3 nm.

In one embodiment, the $D_h$ of the protein in the aqueous formulation is smaller relative to the $D_h$ of the same protein in a buffered solution, irrespective of protein concentration. Thus, in certain embodiments, protein in an aqueous formulation made in accordance with the methods described herein, will have a $D_h$ which is at least 25% less than the $D_h$ of the protein in a buffered solution at the same given concentration. Examples of buffered solutions include, but are not limited to phosphate buffered saline (PBS). In certain embodiments, proteins in the aqueous formulation of the invention have a $D_h$ that is at least 50% less than the $D_h$ of the protein in PBS in at the given concentration; at least 60% less than the $D_h$ of the protein in PBS at the given concentration; at least 70% less than the $D_h$ of the protein in PBS at the given concentration; or more than 70% less than the $D_h$ of the protein in PBS at the given concentration. Ranges intermediate to the above recited percentages are also intended to be part of this invention, e.g., about 55%, 56%, 57%, 64%, 68%, and so forth. In addition, ranges of values using a combination of any of the above recited values as upper and/or lower limits are intended to be included, e.g., about 50% to about 80%.

In one aspect, the aqueous formulation includes the protein at a dosage of about 0.01 mg/kg-10 mg/kg. In another aspect, the dosages of the protein include approximately 1 mg/kg administered every other week, or approximately 0.3 mg/kg administered weekly. A skilled practitioner can ascertain the proper dosage and regime for administering to a subject.

b. "Solid Unit" Formulations

The present invention also provides a low AR composition of the invention formulated as a stable composition of a protein, e.g., particularly a therapeutic protein such as an antibody, or antigen binding portion thereof, and a stabilizer, referred to herein as solid units. These formulations are described, for example, in U.S. Provisional Patent Application 61/893,123, entitled "Stable Solid Protein Compositions and Methods of Making Same", filed on Oct. 18, 2013, the entire contents of which are expressly incorporated herein by reference.

Specifically, it has been discovered that despite having a high proportion of sugar relative to the protein, the solid units of the invention maintain structural rigidity and resist changes in shape and/or volume when stored under ambient conditions, e.g., room temperature and humidity, for extended periods of time. The solid units of the invention remain free-flowing and are able to maintain long-term physical and chemical stability of the protein without significant degradation and/or aggregate formation. The solid units of the invention have many advantages over the art, including that they can be formulated for oral delivery and are easily reconstituted in a diluent, such as water. Because the solid units are readily dissolved, they may be used in dual chamber delivery devices and may be prepared directly in a device for patient use.

As used herein, the term "solid unit," refers to a composition which is suitable for pharmaceutical administration and comprises a protein, e.g., an antibody or peptide, and a stabilizer, e.g., a sugar. The solid unit has a structural rigidity and resistance to changes in shape and/or volume. In a preferred embodiment, the solid unit is obtained by lyophilizing a pharmaceutical formulation of a therapeutic protein. The solid unit may be any shape, e.g., geometric shape, including, but not limited to, a sphere, a cube, a pyramid, a hemisphere, a cylinder, a teardrop, and so forth, including irregularly shaped units. In one embodiment, the solid unit has a volume ranging from about 1 ml to about 20 ml. In one embodiment, the solid unit is not obtained using spray drying techniques, e.g., the solid unit is not a powder or granule.

As used herein, the phrase "a plurality of solid units" refers to a collection or population of solid units, wherein the collection comprises two or more solid units having a substantially uniform shape, e.g., sphere, and/or volume distribution. In one embodiment, the plurality of solid units is free-flowing.

VIII. Kits and Articles of Manufacture Comprising the Low AR Compositions of the Invention Also within the scope of the present invention are kits comprising the low AR compositions of the invention and instructions for use. The term "kit" as used herein refers to a packaged product comprising components with which to administer the antibody, or antigen-binding portion thereof, of the invention for treatment of a disease or disorder. The kit may comprise a box or container that holds the components of the kit. The box or container is affixed with a label or a Food and Drug Administration approved protocol. The box or container holds components of the invention which may be contained within plastic, polyethylene, polypropylene, ethylene, or propylene vessels. The vessels can be capped-tubes or bottles. The kit can also include instructions for administering an antibody of the invention.

The kit can further contain one more additional reagents, such as an immunosuppressive reagent, a cytotoxic agent or a radiotoxic agent or one or more additional antibodies of the invention (e.g., an antibody having a complementary activity which binds to an epitope in the TNFα antigen distinct from a first anti-TNFα antibody). Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation or lyophilized formulation of an antibody or antibody fragment thereof of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. No. 6,792,743, U.S. Pat. No. 5,607,400, U.S. Pat. No. 5,893,842, U.S. Pat. No. 7,081,107, U.S. Pat. No. 7,041,087, U.S. Pat. No. 5,989,227, U.S. Pat. No. 6,807,797, U.S. Pat. No. 6,142,976, U.S. Pat. No. 5,899,889, U.S. Pat. No. 7,699,811, U.S. Pat. No. 7,540,382, U.S. Pat. No. 7,998,120, U.S. Pat. No. 7,645,267, and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising antibodies of the invention are also provided that are useful for various purposes, e.g., research and diagnostic including for purification or immunoprecipitation of protein of interest from cells, detection of the protein of interest in vitro or in vivo.

For isolation and purification of a protein of interest, the kit may contain an antibody coupled to beads (e.g., sepharose beads). Kits may be provided which contain the antibodies for detection and quantitation of a protein of interest in vitro, e.g., in an ELISA or a Western blot. As with the article of manufacture, the kit comprises a container and a label or package insert on or associated with the container. The container holds a composition comprising at least one antibody of the invention. Additional containers may be included that contain, e.g., diluents and buffers, control antibodies. The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising an antibody that is suitable for parenteral administration. In another embodiment, the unit dosage form is provided as a sterile lyophilized powder comprising an antibody that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information. Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within said packaging material, wherein said pharmaceutical agent comprises a liquid formulation containing an antibody. The packaging material includes instruction means which indicate how that said antibody can be used to prevent, treat and/or manage one or more symptoms associated with a disease or disorder.

The present invention is further illustrated by the following examples which should not be construed as limiting in any way. The contents of all cited references, including literature references, issued patents, and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference: U.S. Provisional Patent Application 61/893,123, entitled "STABLE SOLID PROTEIN COMPOSITIONS AND METHODS OF MAKING SAME", filed on Oct. 18, 2013; U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013; U.S. Provisional Patent Application 61/892,710, entitled "MUTATED ANTI-TNFα ANTIBODIES AND METHODS OF THEIR USE", filed on Oct. 18, 2013; U.S. Provisional Patent Application 61/893,068, entitled "LOW ACIDIC SPECIES COMPOSITIONS AND METHODS FOR PRODUCING THE SAME", filed on Oct. 18, 2013; U.S. Provisional Patent Application 61/893,088, entitled "MODULATED LYSINE VARIANT SPECIES AND METHODS FOR PRODUCING AND USING THE SAME", filed on Oct. 18, 2013; and U.S. Provisional Patent Application 61/893,131, entitled "PURIFICATION OF PROTEINS USING HYDROPHOBIC INTERACTION CHROMATOGRAPHY", filed on Oct. 18, 2013.

IX. Examples

Three antibodies were used in connection with the studies outlined below (Examples 1-8). Adalimumab antibody was generated from cell culture processed using chemical defined medium (CDM) and purified by a 4.4 cm (id.)×~20 cm (L) MabSelect SuRe Protein A column. mAb X bulk drug substance was obtained from a three-step large scale purification process. mAb Y antibody was generated from a large scale manufacturing process and purified by a MabSelect SuRe Protein A column. Adalimumab Protein A eluate was in a buffer of ~20 mM acetic acid at pH ~4.2. The mAb X was in a buffer containing ~15 mM histidine, pH ~6. The mAb Y was in a buffer containing ~10 mM sodium formate, pH ~4.2. Each mAb feed was conditioned to the targeted pH, conductivity and concentration prior to the displacement chromatography experiment.

The cationic displacers, Expell SP1™ and protamine sulfate (from salmon sperm), were purchased from SACHEM Chemical Company and Sigma Aldrich, respectively.

Poros XS CEX resin (Life Technologies) was packed in a 0.66 cm×~25 cm column. The column was equilibrated with a 140 mM Tris/Acetate buffer or a 30 mM MES, 10 mM NaCl buffer at the targeted pH and conductivity (Table 1). After equilibration, the column was loaded with each pre-conditioned feed at a resin loading level of ~40 g/L followed by a 2 CV of equilibration buffer wash. The displacing buffer, which consists of defined concentration of Expell SP1™ or protamine sulfate in the equilibration buffer, was flowed through the column to initiate the displacement process. In standard one-step displacement wash process, this step was continued for at least 30 CV at a flow rate corresponding to 15 to 22 min residence time (RT) before column regeneration and cleaning with a caustic solution consisting of 0.5 N NaOH and 0.5 M KCl. Alternatively, the displacement wash step comprised two displacement buffers each flowing for defined volumes, or a linear gradient flow from low to high concentration displacer buffer. Sample fractions were collected at every 0.5 or 1 CV for protein concentration and quality analysis. The specific processing conditions are detailed in Tables 1 and 2.

Capto MMC resin (GE Healthcare) was packed in a 0.66 cm×~30 cm column. The column was equilibrated with a 140 mM Tris/Acetate buffer at the targeted pH and conductivity (Table 3). After equilibration, the column was loaded with each pre-conditioned feed at a resin loading level about 34 to 40 g/L followed by a 2 CV equilibration buffer wash. The displacing buffer, which consists of defined concentration of protamine sulfate in the equilibration buffer, was flowed through the column to initiate the displacement process. This step was continued for 30 CV at a flow rate corresponding to ~22 min RT before column regeneration and cleaning. Sample fractions were collected at every 0.5 or 1 CV for protein concentration and quality analysis. The specific processing conditions are detailed in Table 3.

The levels of acidic species and other charge variants in the Adalimumab, mAb X and mAb Y samples were quantified using the respective qualified CEX-HPLC method. For Adalimumab, a 4 mm×250 mm analytical Dionex ProPac WCX-10 column (Dionex, CA) was used along with a Shimazhu HPLC system. The mobile phases were 10 mM Sodium Phosphate dibasic pH 7.5 buffer (Mobile phase A) and 10 mM Sodium Phosphate dibasic, 500 mM Sodium Chloride pH 5.5 buffer (Mobile phase B). A binary gradient (6% B: 0 min; 6-16% B: 0-20 min; 16-100% B: 20-22 min; 100% B: 22-26 min; 100-6% B: 26-28 min; 6% B: 28-35 min) was used with detection at 280 nm. Quantitation was based on the relative area percentage of detected peaks. The peaks that elute at residence time less than ~7 min were together represented as the acidic peaks or AR region.

For mAb X, a 4 mm×250 mm analytical Dionex ProPac WCX-10 column (Dionex, CA) was used along with a Shimazhu HPLC system. The mobile phases were 20 mM MES, pH 6.5 buffer (Mobile phase A) and 20 mM MES, 500 mM NaCl, pH 6.5 buffer (Mobile phase B). A binary gradient (10% B: 0 min; 10-28% B: 1-46 min; 28-100% B: 46-47 min; 100% B: 47-52 min; 100-10% B: 52-53 min; 10% B: 53-58 min) was used with detection at 280 nm. Quantitation was based on the relative area percentage of detected peaks. All peaks eluting prior to the Main Isoform peak were summed as the acidic region, and all peaks eluting after the Main peak were summed as the basic region.

For mAb Y, a 4 mm×250 mm Dionex ProPac analytical WCX-10 column (Dionex, CA) was used on a Shimazhu HPLC system. The mobile phases were 20 mM MES, pH 6.2 (Mobile phase A) and 20 mM MES, 250 mM NaCl, pH 6.2 (Mobile phase B). A binary gradient (1% B: 0-1 min; 1-25% B: 1-46 min; 25-100% B: 46-47 min; 100% B: 47-52 min; 100-1% B: 52-53 min; 1% B: 53-60 min) was used with detection at 280 nm. Column temperature was set at 35° C. Quantitation was based on the relative area percentage of detected peaks. All peaks eluting prior to the Main Isoform peak (but after 2 min retention time) were summed as the acidic region, and all peaks eluting after the Main peak were summed as the basic region.

The levels of aggregates, monomer and fragments in eluate samples were measured using a SEC method for each molecule. For Adalimumab and mAb Y, a TSK-gel G3000SWxL, 5 µm, 125 Å, 7.8×300 mm column (Tosoh Bioscience) was used while a TSK-gel Super SW3000, 4 µm, 250 Å, 4.6×300 mm column (Tosoh Bioscience) was used for mAb X along with an Agilent or a Shimazhu HPLC system. For Adalimumab and mAb X, injections were made under isocratic elution conditions using a mobile phase consisting of 100 mM sodium sulfate and 100 mM sodium phosphate at pH 6.8, and detected with UV absorbance at 214 nm. For mAb Y, the mobile phase consists of 1×PBS at pH 7.4, and elution profile detected with UV absorbance at 280 nm. Quantification is based on the relative area of detected peaks.

An HCP ELISA assay was used to determine the HCP levels in various samples and feeds for all three mAbs.

TABLE 1

Processing conditions for Poros XS one-step displacement chromatography

| Molecule | Displacer | Conc. (mM) | Buffer System | pH | Conductivity (mS/cm) | Loading Conditions | Regeneration |
|---|---|---|---|---|---|---|---|
| Adalimumab | Expell SP1 | 0.5-3 | Tris/Acetate | 6.7-7.8 | 5.4-6.6 | pH ~7.5, ~6 mS/cm | 2M NaCl |
| | | 2-5 | MES/NaCl | 6.1 | 2.1 | pH 6.1, ~2 mS/cm | 0.2M acetic acid & 1M KCl |
| | Protamine Sulfate | 0.25-2 | Tris/Acetate | 6.5-7.5 | 5.6-6.6 | pH 7.5, 5.4-6.3 mS/cm | 2M NaCl, 6M Guanidine HCl |
| mAb X | Expell SP1 | 0.5-2 | Tris/Acetate | 6 | 6.2-6.5 | pH 6, ~6 mS/cm | 2M NaCl |
| | Protamine Sulfate | 0.25-0.5 | Tris/Acetate | 6 | 6.0-6.5 | pH 6, 5.6-6.5 mS/cm | 2M NaCl, 6M Guanidine HCl |
| mAb Y | Expell SP1 | 0.5-1 | Tris/Acetate | 5 | ~6 | pH 5, 6.2 mS/cm | 2M NaCl |

TABLE 2

Processing conditions for Poros XS two-step or linear gradient displacement chromatography

| Molecule | Displacer | Displacement Method | Concentration (mM) | Buffer System | pH | Conductivity (mS/cm) | Loading Conditions | Regeneration |
|---|---|---|---|---|---|---|---|---|
| Adalimumab | Expell SP1 | Two-step | (1): 0.5 mM, 25CV; (2): 2 mM, 20CV | Tris/Acetate | 7 | ~6 | pH 7.5, 6.1 mS/cm | 2M NaCl |

TABLE 2-continued

Processing conditions for Poros XS two-step or linear gradient displacement chromatography

| Molecule | Displacer | Displacement Method | Displacer Concentration (mM) | Equilibration/Wash/Displacing buffer | | | Loading Conditions | Regeneration |
|---|---|---|---|---|---|---|---|---|
| | | | | Buffer System | pH | Conductivity (mS/cm) | | |
| | Protamine Sulfate | Two-step | (1): 0.25 mM, 10CV; (2): 2 mM, 10CV | Tris/Acetate | 7.5 | 5.5 | pH 7.5, 6.1 mS/cm | 2M NaCl, 6M Guanidine HCl |
| | Expell SP1 | Linear Gradient | 0-1 mM over 40 CV | Tris/Acetate | 7 | ~6 | pH 7.5, 6.0 mS/cm | 2M NaCl |
| | Protamine Sulfate | Linear Gradient | 0-1 mM over 40 CV | Tris/Acetate | 7.5 | ~6 | pH 7.5, 5.9 mS/cm | 2M NaCl, 6M Guanidine HCl |
| mAb X | Expell SP1 | Two-step | (1): 0.5 mM, 22CV; (2): 2 mM, 12CV | Tris/Acetate | 6 | 6.1 | pH 6, 6.3 mS/cm | 2M NaCl |
| | Protamine Sulfate | Two-step | (1): 0.35 mM, 10CV; (2): 0.5 mM, 10CV | Tris/Acetate | 6 | ~6 | pH 6, 6.3 mS/cm | 2M NaCl |

TABLE 3

Processing conditions for Capto MMC one-step displacement chromatography

| Molecule | Displacer | Displacer Concentration (mM) | Equilibration/Wash/Displacing buffer | | | Loading Conditions | Regeneration | CIP |
|---|---|---|---|---|---|---|---|---|
| | | | Buffer System | pH | Conductivity (mS/cm) | | | |
| Adalimumab | Protamine Sulfate | 0.25-0.5 | Tris/Acetate | 7-7.5 | ~6 | pH 7.5, 5.3-6.1 mS/cm | 2M NaCl, 6M Guanidine HCl | 0.5N NaOH + 0.5M KCl |
| mAb X | Protamine Sulfate | 0.25-0.5 | Tris/Acetate | 7-7.7 | ~6 | pH 7-7.7, 5.9-6.5 mS/cm | 2M NaCl, 6M Guanidine HCl | |
| mAb Y | Protamine Sulfate | 0.25-0.5 | Tris/Acetate | 5-5.5 | ~6.5 | pH 5.5, 5.2-5.6 mS/cm | 2M NaCl, 6M Guanidine HCl | |

Example 1. Displacement Chromatography Performances of Expell SP1™ for Adalimumab on Poros XS Resin Expell SP1™ is a low molecular weight quaternary ammonium salt that exhibited pronounced displacement effect for Adalimumab on Poros XS resin under selected sets of operating conditions. The feed material used for this set of experiments contained about 20-25% total AR, of which 2-5% was AR1 and 18-20% AR2. The results for this system are shown in the following sections.

A representative, desired displacement chromatographic profile is shown in FIG. 1a (solid line). In this experiment, the column was equilibrated with a pH 7 Tris/acetate buffer (6.4 mS/cm), loaded with a pre-adjusted protein A eluate feed (pH 7.5, 6.3 mS/cm, ~3.4 g/L) to ~40 g/L resin loading level, followed by EQ buffer wash and then displacement process using 1 mM Expell SP1™ in the pH 7 EQ buffer. The extended, square shape UV280 "elution" profile indicated establishing a proper displacement train and thus a degree of separation of the feed components can be realized.

FIG. 2 illustrates the CEX-HPLC chromatograms for several samples taken along this well-established displacement UV trace. Clearly, the variant species were rearranged during the displacement process according to their respective binding affinity to the resin: AR1 was enriched in the foremost of the displacement train followed by AR2, Lys 0, Lys 1 and Lys 2 in order.

Figure 3:
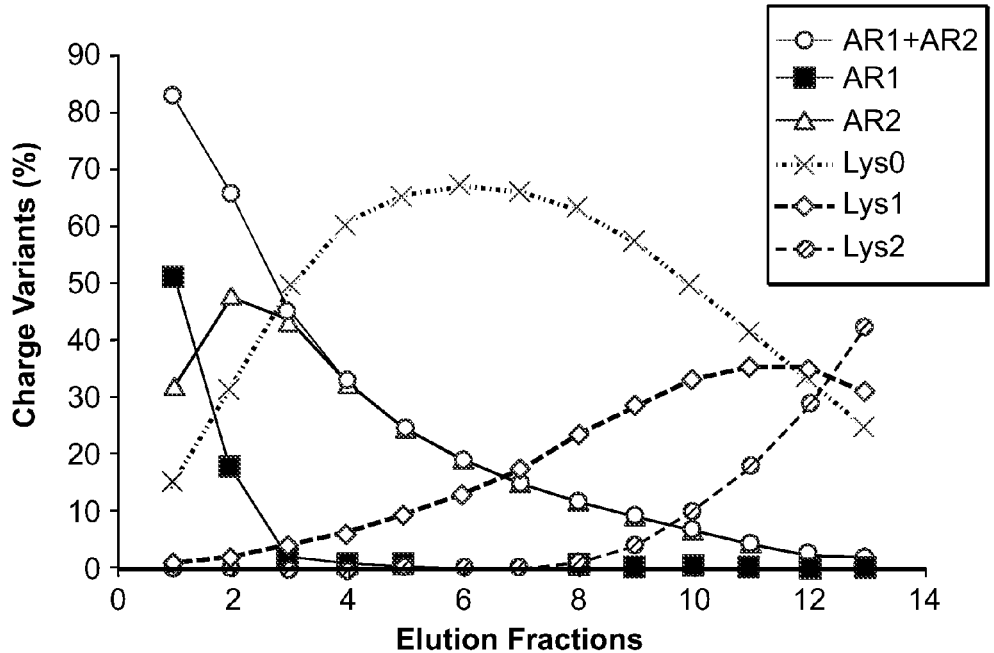
FIG. 3 depicts the separation of Adalimumab charge variants by Poros XS displacement chromatography using Expell SP1™.
Figure 4:
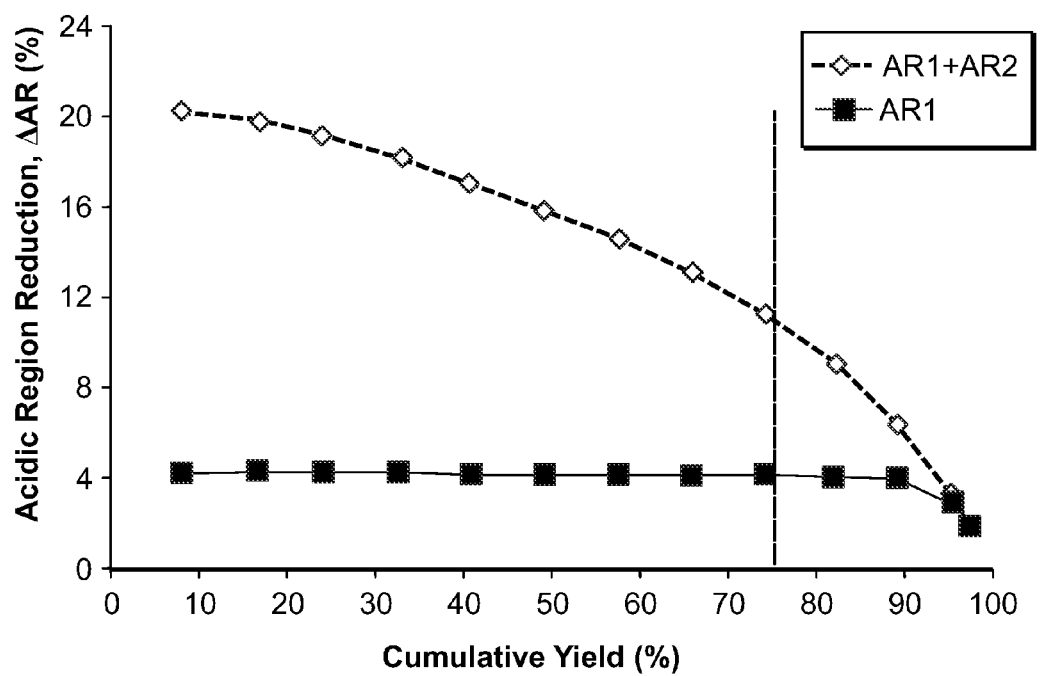
FIG. 4 depicts the reduction of acidic species level in Adalimumab by Poros XS displacement chromatography using Expell SP1™.

FIG. 3 shows the distribution of each variant species in all the collected sample fractions. The acidic species were enriched in the earlier fractions compared to the Lys variants. By excluding those earlier fractions the product pool AR level will be reduced relative to that in the feed. This is reflected in FIG. 4 which plots the reduction of total AR (i.e., AR1+AR2) and AR1 level versus cumulative product yield. At a yield of ~75%, the total AR % was reduced by 11.7% and AR1% by 4.2% under this set of condition. Along with the removal of AR species, the product pool lysine variant species distribution profile was also modulated. As shown in Table 4, below, the ratio of Lys 0 species to the lysine variant sum decreased from 0.67 to 0.62; the ratio of Lys 1 species to the lysine variant sum increased from 0.24 to 0.28; and the ratio of Lys 2 species to the lysine variant sum increased from 0.08 to 0.1. The lysine prolife can be further altered by pooling different fractions from the displacement chromatography process.

Varying the processing conditions such as the buffer pH and displacer concentration can modulate the shape of the displacement chromatogram and hence the separation performance. In an extreme case, the chromatogram more or less resembles the typical elution "peak" profile without incurring the separation of variant species (FIGS. 1A and 1B). Interestingly, this occurs at stronger binding conditions; for instance, the conditions corresponding to FIG. 1B is pH 6.1 and ~2 mS/cm for equilibration, loading, wash, and displacement. Without being bond by theory, the lack of variant separation under such conditions may be due to the diminishing difference in binding affinity of each species and thus the selectivity by the displacer.

Figure 5:
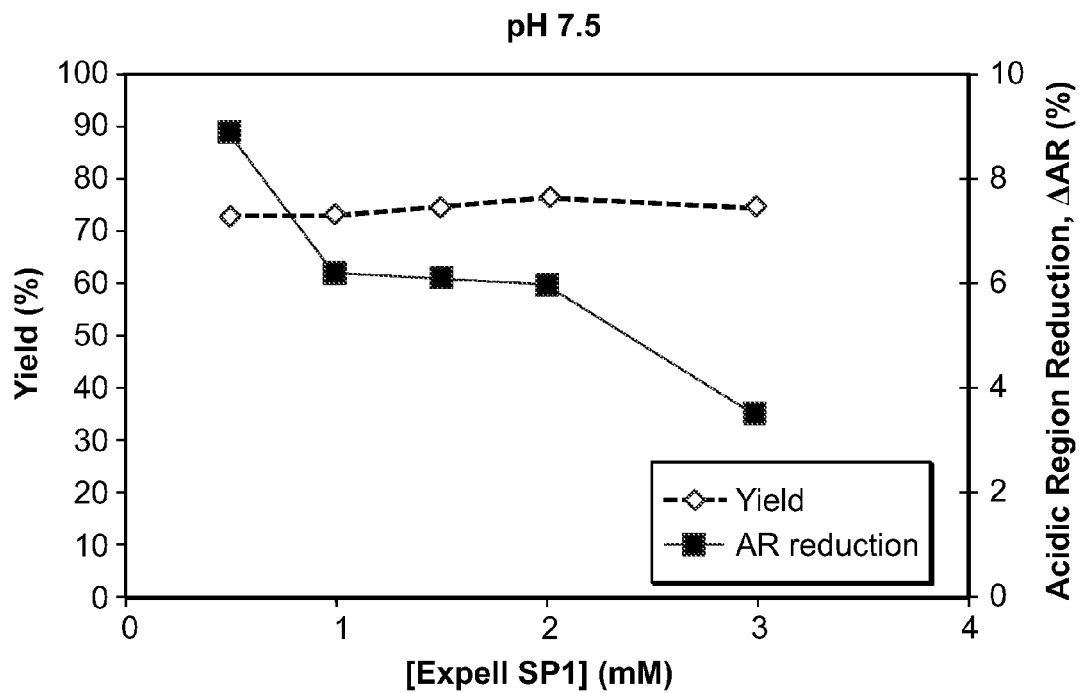
FIG. 5 depicts the effect of Expell SP1™ concentration on acidic species reduction in Adalimumab by Poros XS displacement chromatography.

The effect of Expell SP1™ concentration on Adalimumab AR reduction was measured in pH 7.5 Tris/Acetate buffer, as shown in FIG. 5. The same equilibration/wash and feed loading conditions were used for all the runs here. Increasing Expell SP1™ concentration from 0.5 to 3 mM decreased $\Delta$AR % from 8.9% to 3.5% at similar product yield ~75%. Controlling the Expell SP1™ concentration within 2 mM will consistently achieve ≥6% AR % reduction.

Figure 6:
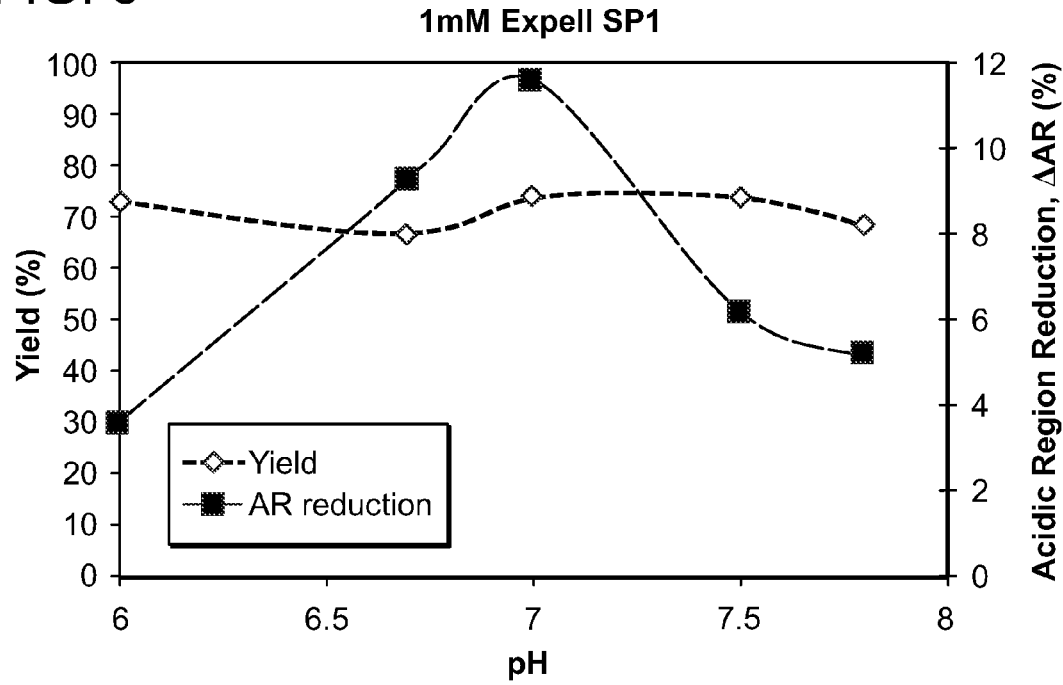
FIG. 6 depicts the effect of pH on acidic species reduction in Adalimumab by Poros XS displacement chromatography using Expell SP1™.

The effect of displacing buffer pH on AR reduction for Adalimumab was measured at 1 mM Expell SP1™ concentration in the Tris/Acetate buffer, as shown in FIG. 6. In this set of experiments, the column was conditioned with an EQ buffer at the respective displacing buffer pH, and then loaded with protein feed at pH 7.5 and ~6 mS/cm followed by a brief EQ buffer wash before starting the displacement step. The buffer pH significantly impacts AR clearance in pH range of 6-8. At similar yield (~75%), the maximal reduction in AR level (~12%) is seen at pH 7. Despite such pH-dependency, the majority of the conditions here (pH 6.5 to 7.8) gave at least 5% AR removal in final product pool.

In the aforementioned experiments, one displacing buffer was used to achieve the protein variant separation. It was observed that, relatively lower displacer concentration gives better separation but tends to elongate the process due to substantial increase in the required displacing buffer volume. For instance, when using 0.5 mM Expell SP1™ in a pH 7 displacing buffer (Table 1), the displacement phase requires 44 column volumes (CV) of this buffer for completion. To accelerate the operation without affecting the acidic species separation, a two-step displacement process was explored at this pH condition. In the example provided here, the displacement process was started with 0.5 mM Expell SP1™ at pH 7 and continued for 25 CV, followed by 20 CV of 2 mM Expell SP1™ solution at the same pH. Under such conditions, the protein displacement profile was completed in a total of 33 CV which is 25% less than that required for one-step displacement process, thus significantly shortening the process.

Figure 7:
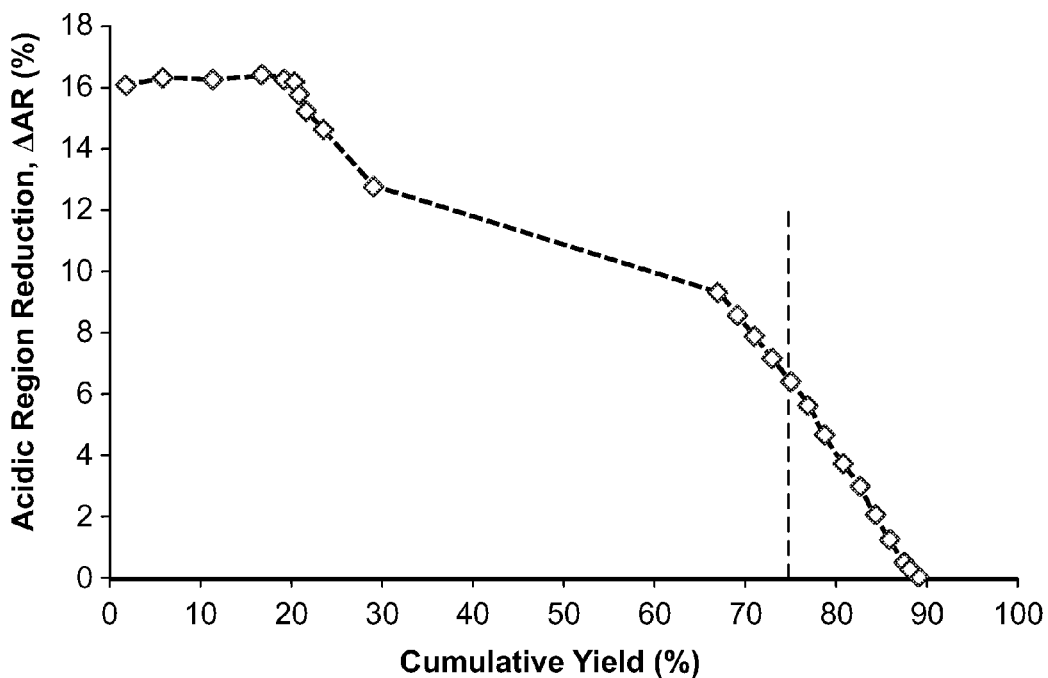
FIG. 7 depicts the reduction of acidic species level in Adalimumab by Poros XS two-step displacement chromatography using Expell SP1™.

FIG. 7 shows the reduction of AR % versus product yield for the aforementioned two-step displacement run. The net total AR level in product pool was reduced by 6.6% at ~75% yield. In contrast to the conventional use of a single displacing solution consisting of a single displacer at a defined concentration, herein the AR clearance was achieved by excluding the AR-enriched early fractions as induced by 0.5 mM Expell SP1™ displacement, while the higher Expell SP1™ concentration was used to accelerate the displacement of the remainder proteins off the solid phase. In light of this unexpected similar product quality and yield results, step-gradient displacement schemes are considered to be advantageous over conventional strategies.

Besides the two-step displacement scheme, a linear gradient displacement method was also tested for the Adalimumab charge variant separation. As detailed in Table 2, after the feed loading at pH 7.5 (~6 mS/cm), the column was briefly washed with the equilibration buffer (pH 7, ~6 mS/cm) and then started with a 40 CV linear gradient from the EQ buffer to a 1 mM Expell SP1™ displacing buffer (which was made from the EQ buffer). Under such condition, the displacement profile matured within this 40 CV gradient. The product eluate was pooled by excluding the first a few fractions. In this case, the net AR % decreased by 6.8% at a product recovery of 72%.

Figure 8:
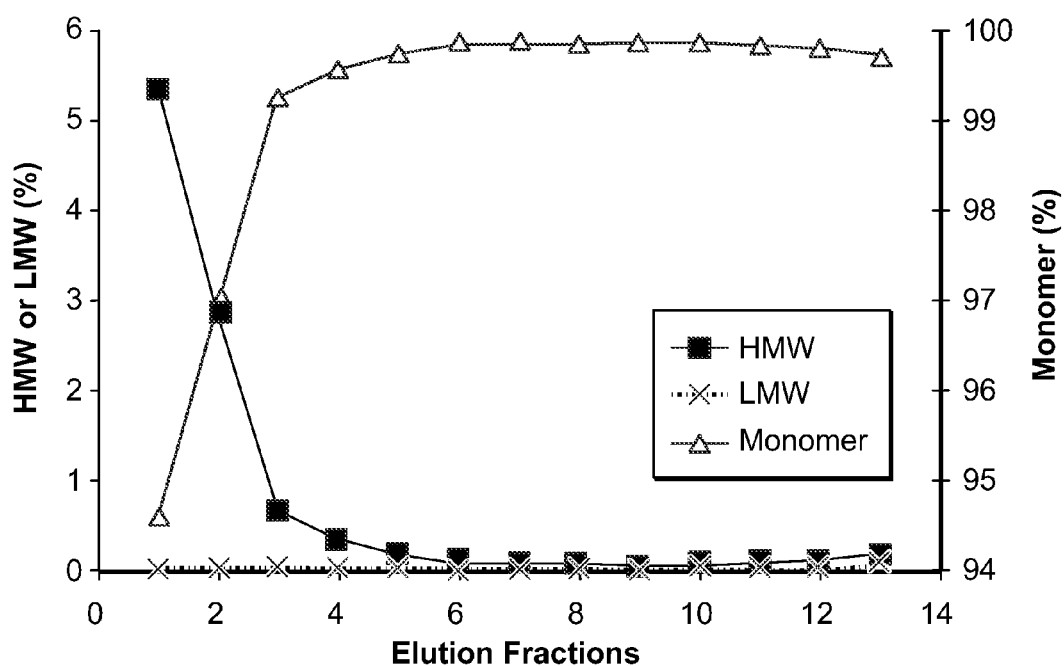
FIG. 8 depicts the separation of Adalimumab size variants by Poros XS displacement chromatography using Expell SP1™.

Apart from acidic species, other product- or process-related impurities can be effectively separated by Poros XS displacement chromatography using Expell SP1™ as the displacer. FIG. 8 shows the separation of aggregates, monomer and fragments in Adalimumab sample fractions obtained from a one-step displacement experiment using 1 mM Expell SP1™, pH 7 buffer. It should be noted that the last two fractions from this run were not collected, therefore the increased aggregate levels at the end of the displacement train was not fully exemplified here. Interestingly, the early fractions which contained elevated acidic species also showed enriched aggregates, indicating that this population of aggregates may consist of more acidic species, or the acidic species has higher propensity to form aggregates. As summarized in Table 4, the aggregate level in the product pool (at ~75% yield) was reduced from the feed level 1.16% to 0.11% and the fragment level down to 0.04% along with significant reduction in the AR concentration. In addition to the standard method, the linear gradient displacement run also showed aggregate reduction from the feed level of 0.9% to about 0.2% in final product.

Figure 9:
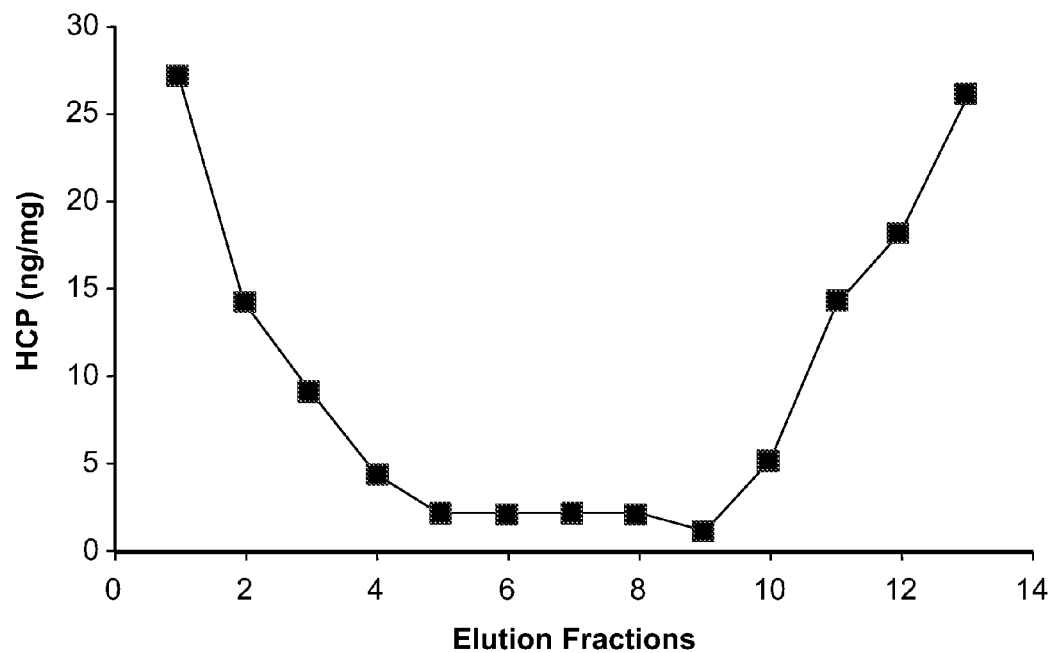
FIG. 9 depicts the separation of HCP in Adalimumab by Poros XS displacement chromatography using Expell SP1™.

FIG. 9 shows the distribution of HCP in the Adalimumab displacement train coming off the Poros XS column. Relatively higher level of HCP was observed at both ends of the train, due to their diverse charge characteristics and associated binding strength. The final product pool HCP level was reduced to 5 ng/mg from the starting feed, representing approximately 50-fold reduction.

TABLE 4

Step yield & product quality in Adalimumab before and after Poros XS displacement chromatography using Expell SP1 ™ (pH 7, 1 mM Expell SP1 ™)

| | Yield % | AR1 % | AR2 % | Lys Sum % | Lys 0 % | Lys 1 % | Lys 2 % | HMW % | Monomer % | LMW % | HCP (ng/mg) |
|---|---|---|---|---|---|---|---|---|---|---|---|
| Feed | — | 4.3 | 17.8 | 77.9 | 52.5 | 19.0 | 6.5 | 1.16 | 98.57 | 0.27 | 267 |
| Product pool | 74 | 0.1 | 10.3 | 89.6 | 55.5 | 24.8 | 9.3 | 0.11 | 99.85 | 0.04 | 5 |

Example 2. Displacement Chromatography Performance of Protamine Sulfate for Adalimumab on Poros XS Resin Protamine sulfate, a cationic peptide with molecule weight ~5.1 kD, was also evaluated as a cation exchange displacer for Adalimumab on Poros XS resin under various operating conditions. The feed material used for this set of experiments contained about 17-24% total AR, of which 3-6% was AR1 and 14-19% AR2. The results for this system are illustrated in the following sections.

Figure 10:
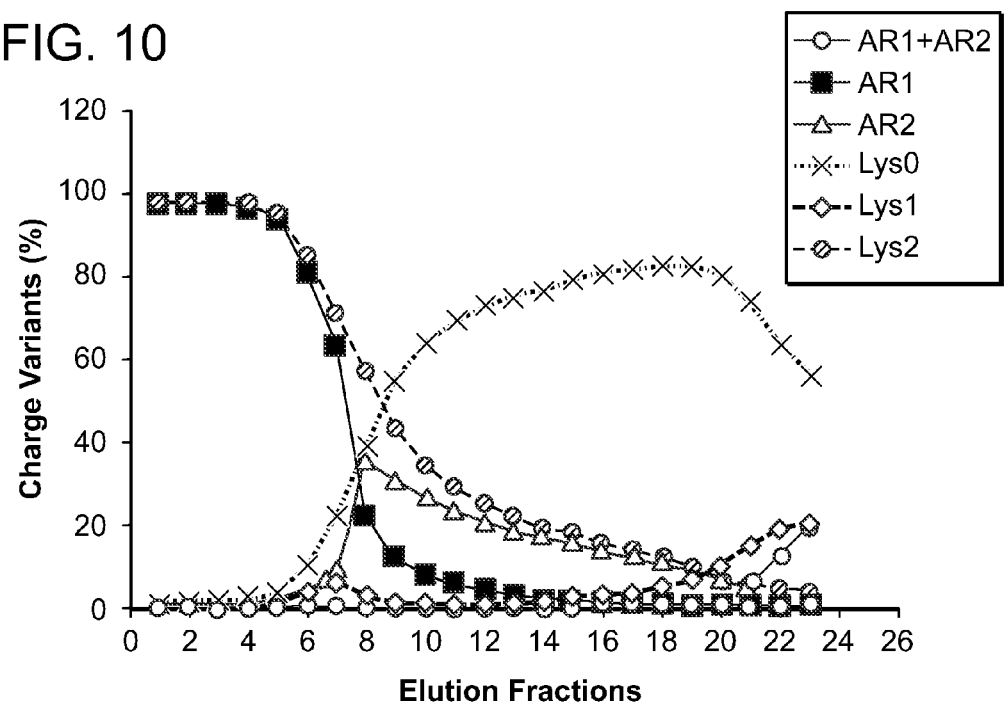
FIG. 10 depicts the separation of Adalimumab charge variants by Poros XS displacement chromatography using protamine sulfate.
Figure 11:
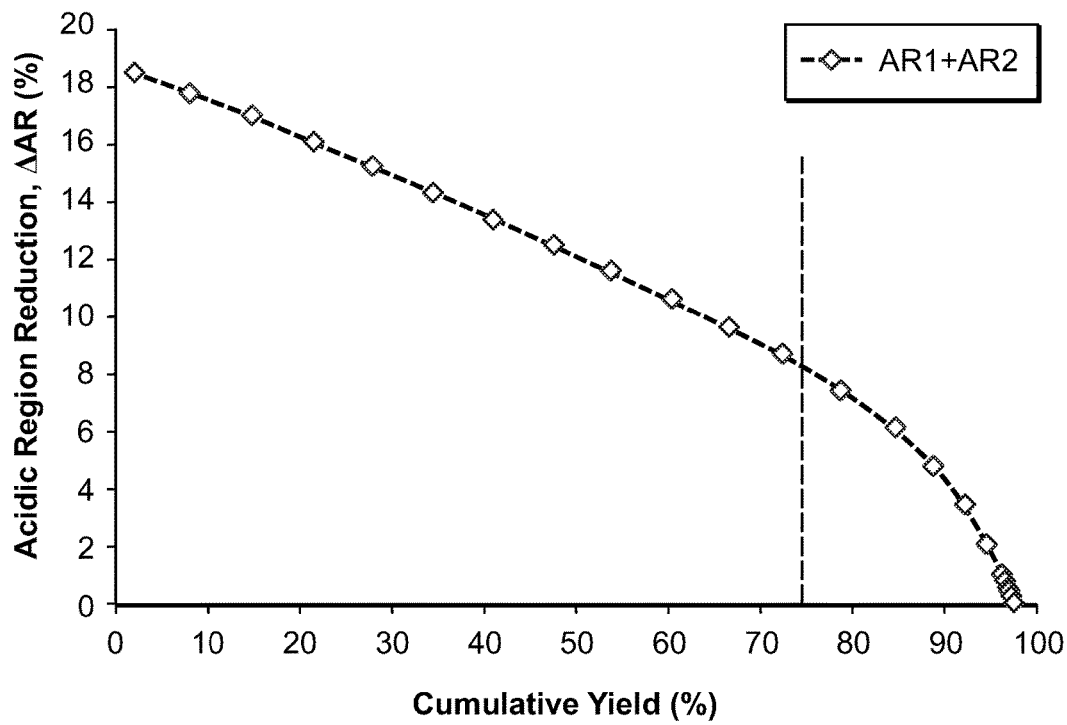
FIG. 11 depicts the reduction of acidic species in Adalimumab by Poros XS displacement chromatography using protamine sulfate.

FIG. 10 shows the distribution of charge variant species in sample fractions collected from a well established displacement process induced by protamine sulfate. In this experiment, the column was equilibrated with a pH 7.5 Tris/acetate buffer (5.6 mS/cm), loaded with a pre-adjusted protein A eluate feed (pH 7.5, 5.4 mS/cm, 5.2 g/L) to 39 g/L resin loading level, followed by a brief EQ buffer wash and then displacement process using 0.5 mM protamine sulfate dissolved in the pH 7.5 EQ buffer. Similar to the Expell SP1™ displacement profile (FIG. 3), the charge variants were enriched at different locations of the displacement train and were peaked in the order of AR1, AR2, Lys0, Lys1 and Lys2. The cumulative AR % reduction as a function of product yield is illustrated in FIG. 11. A 6-8% decrease in the total AR level can be obtained at a yield of 75-85% under this set of condition. The actual levels of AR1, AR2 and total lysine variant species (i.e., Lys 0+Lys 1+Lys 2) for the feed and the final product pool are shown in Table 5.

Figure 12:
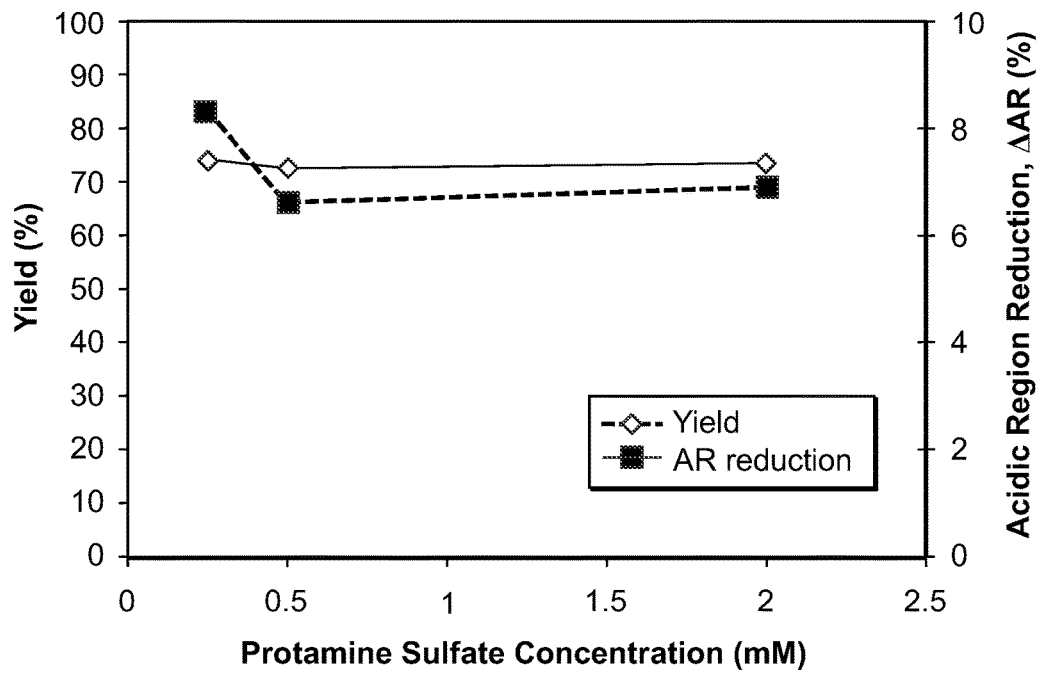
FIG. 12 depicts the effect of protamine sulfate concentration on acidic species reduction in Adalimumab by Poros XS displacement chromatography.

The effect of protamine sulfate concentration on Adalimumab AR reduction was measured in pH 7.5 Tris/Acetate buffer, as shown in FIG. 12. The same equilibration/wash and feed loading conditions as described above were used for all the runs here. At similar yield (~75%), the total AR % was reduced by approximately 7-8% when using 0.25 to 2 mM protamine sulfate. This broad concentration range reflects the robustness of charge variant separation by protamine sulfate displacement process.

Figure 13:
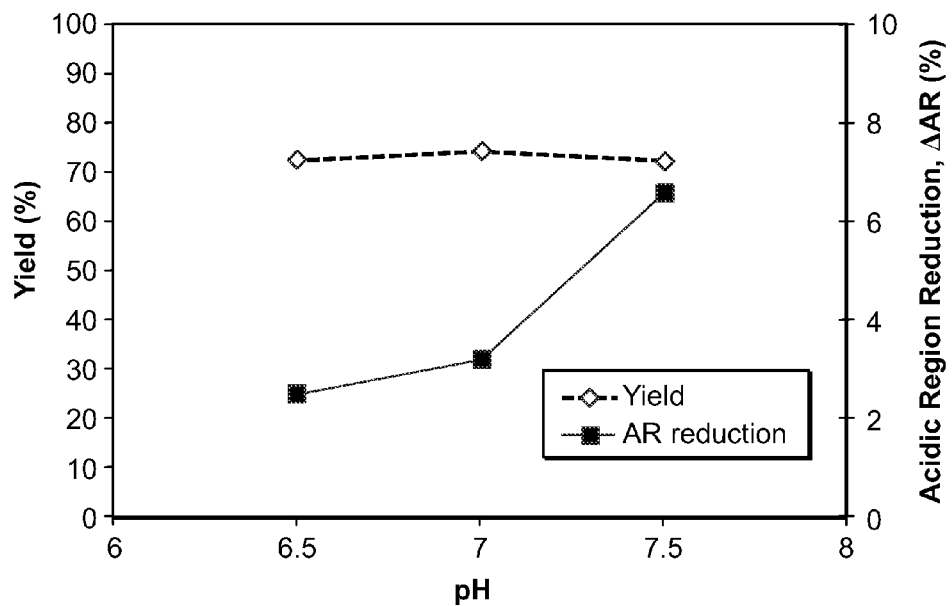
FIG. 13 depicts the effect of pH on acidic species reduction in Adalimumab by Poros XS displacement chromatography using protamine sulfate.

The effect of displacing buffer pH on AR clearance for Adalimumab was measured at 0.5 mM protamine sulfate concentration in Tris/Acetate buffer. In this set of experiments, the column was conditioned with an EQ buffer at the respective displacing buffer pH, loaded with protein feed at pH 7.5 and ~6 mS/cm followed by a brief EQ buffer wash before starting the displacement phase. As shown in FIG. 13, the extent of AR reduction increases significantly as pH varies from 6.5 to 7.5. Over 6% decrease in AR level can be achieved at pH 7.5 with a product yield ~75%.

Figure 14:
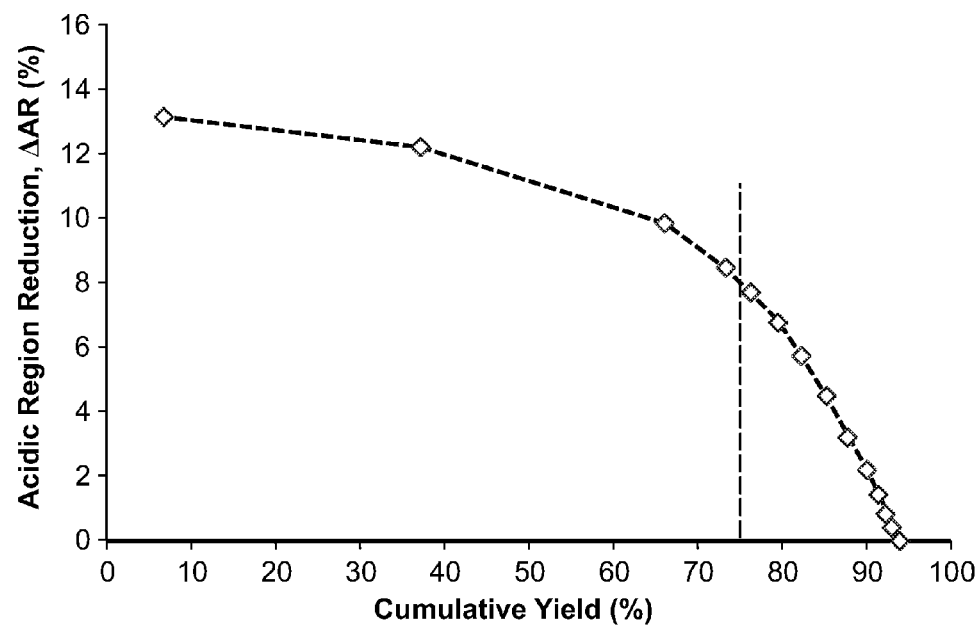
FIG. 14 depicts the reduction of acidic species in Adalimumab by Poros XS two-step displacement chromatography using protamine sulfate.

The two-step displacement scheme was also tested with protamine sulfate. In one experiment, the displacement process consists of 10 CV of 0.25 mM protamine and 10 CV of 2 mM protamine at pH 7.5 (Table 2). The protein displacement profile was completed in a total of 13 CV, which is about 11 CV or almost 2 fold shorter than that in the one-step displacement process with 0.25 mM protamine sulfate. The reduction of AR % versus product yield is shown in FIG. 14. The total AR level in product pool were reduced by ~8% at ~75% yield, which is comparable to that achieved by the one-step displacement process using 0.25 mM protamine sulfate.

Figure 15:
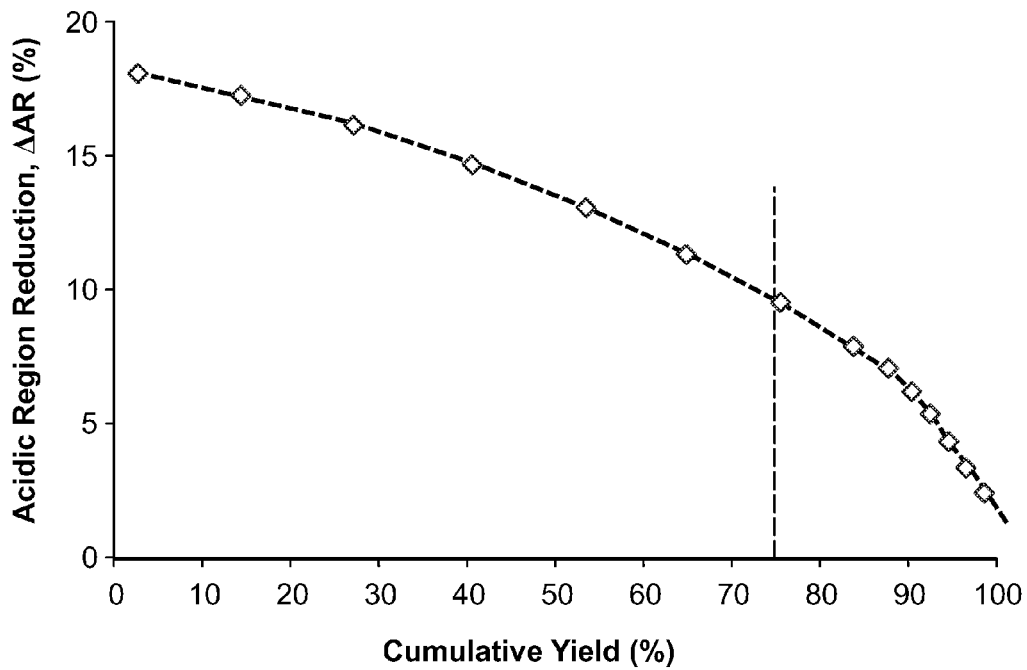
FIG. 15 depicts the reduction of acidic species in Adalimumab on Poros XS using protamine sulfate linear gradient displacement chromatography.

The linear gradient displacement scheme was also evaluated with protamine sulfate on Poros XS resin for Adalimumab charge variant separation. As summarized in Table 2, after the feed loading at pH 7.5 (5.9 mS/cm), the column was briefly washed with the equilibration buffer (pH 7.5, ~6 mS/cm) and then started with a 40 CV linear gradient from the EQ buffer to a 1 mM protamine sulfate displacing buffer (which was made from the EQ buffer). FIG. 15 shows the cumulative ΔAR % versus yield from this run. At a product yield of 75.6%, the total AR % was reduced from the feed level of 21.3% to 12.1%.

Figure 16:
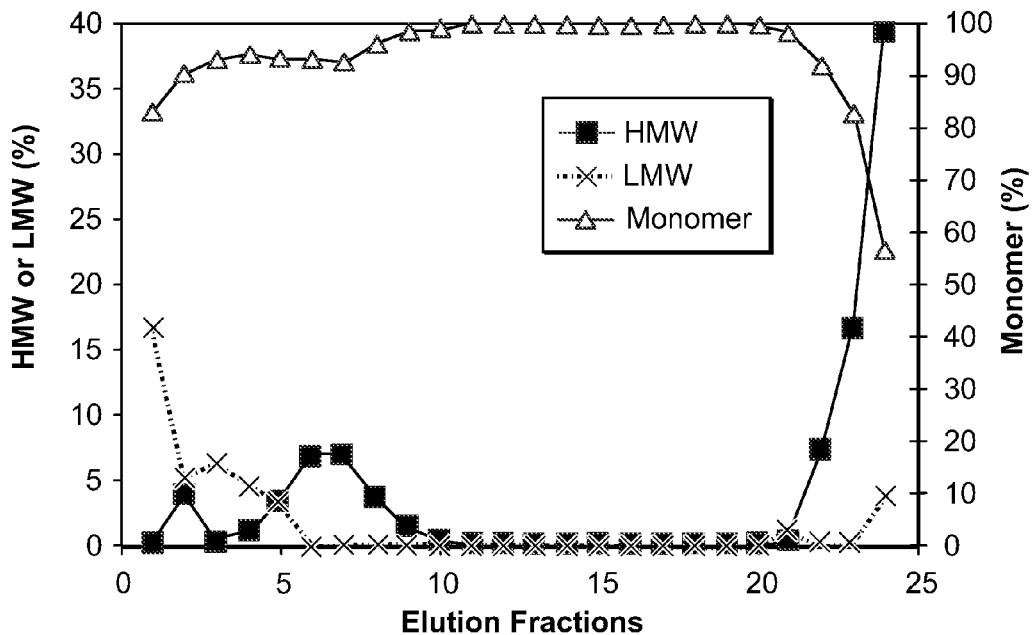
FIG. 16 depicts the separation of Adalimumab size variants by Poros XS displacement chromatography using protamine sulfate.

Protamine sulfate displacement chromatography also demonstrated significant clearance of aggregates, fragments and HCP. FIG. 16 exemplifies the size variant profiles of Adalimumab from the same experiment described above (i.e., 0.5 mM protamine sulfate, pH 7.5, one-step displacement run). As expected, the fragments were mostly enriched at the front while the aggregates primarily resided at the back of the train. Similar to that shown in FIG. 8, a subpopulation of the aggregates was also observed in the displacement front; in addition, a portion of fragments was noticed at the tail. Table 5 compares the levels of aggregates, fragments and HCP in final product pool (at ~75% yield) relative to the feed.

TABLE 5

Step yield & product quality in Adalimumab before and after Poros XS displacement chromatography using protamine sulfate

| | Yield % | AR1 % | AR2 % | Lys Sum % | HMW % | Monomer % | LMW % | HCP (ng/mg) |
|---|---|---|---|---|---|---|---|---|
| Feed | — | 4.1 | 16.9 | 79.0 | 0.8 | 98.0 | 1.2 | 153 |
| Product pool | 73 | 1.3 | 13.1 | 84.7 | 0.3 | 99.6 | 0.1 | 14 |

Example 3. Displacement Chromatography Performance of Expell SP1™ for mAb X on Poros XS Resin The displacement separation performance of Expell SP1™ was assessed for mAb X on the Poros XS resin. A purified mAb X drug substance was used in this study, which contained about 16-17% acidic species and 12-14% basic species.

Figure 17:
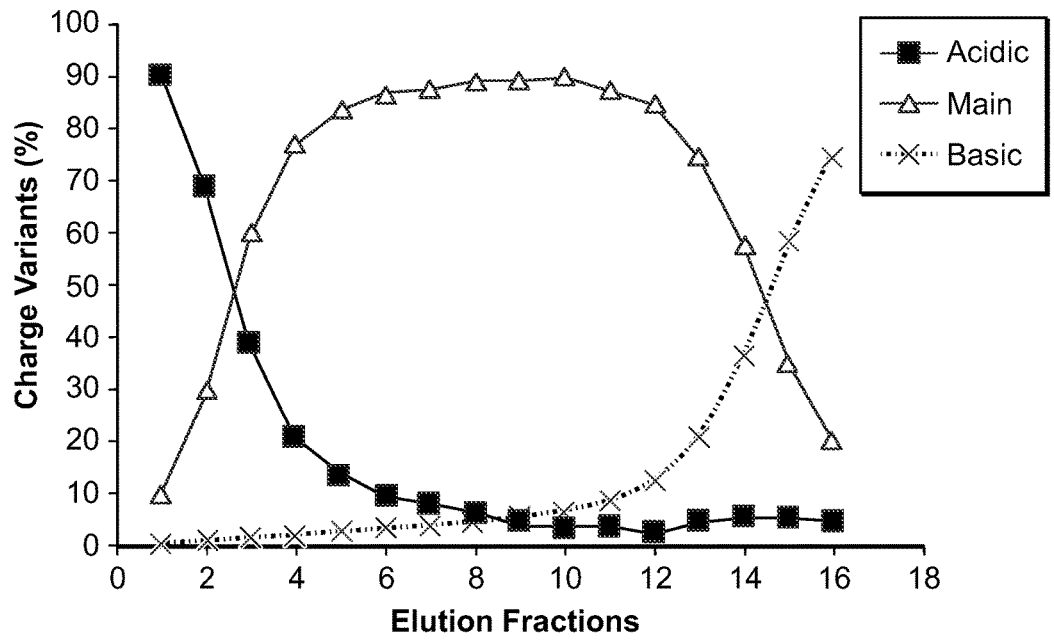
FIG. 17 depicts the separation of mAb X charge variants by Poros XS displacement chromatography using Expell SP1™.
Figure 18:
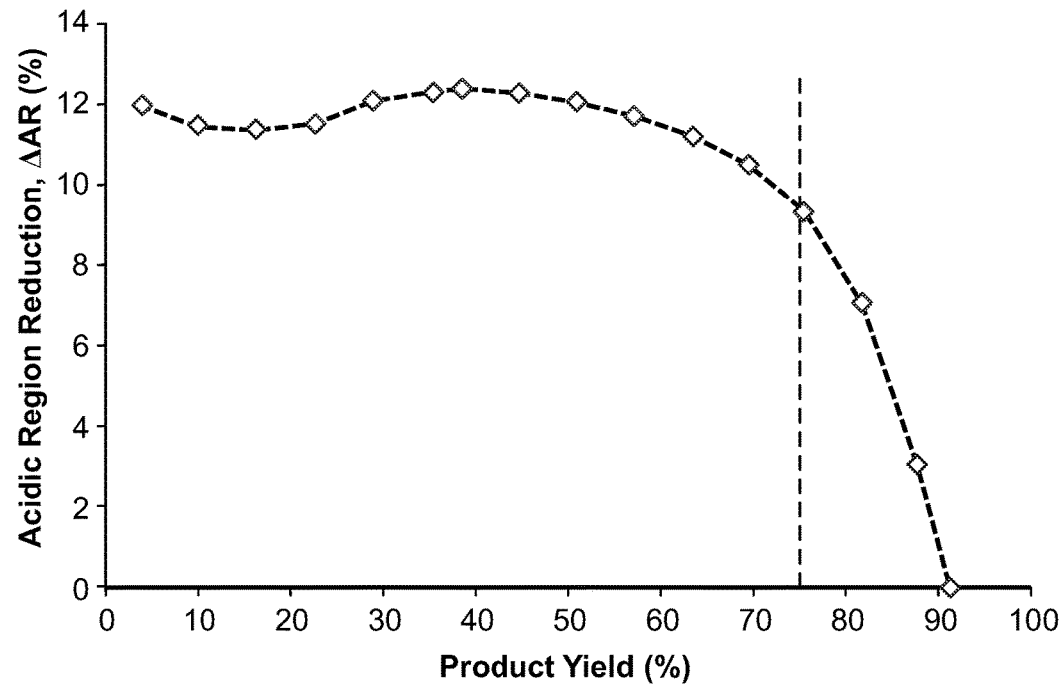
FIG. 18 depicts the reduction of acidic species in mAb X by Poros XS displacement chromatography using Expell SP1™.

A representative set of mAb X charge variant separation profiles are shown in FIGS. 17 and 18. In this experiment, the Poros XS column was loaded with 40 g/L of mAb X at pH 6, 6 mS/cm Tris/Acetate binding condition, and was displaced using 1 mM Expell SP1™ in a pH 6, 6 mS/cm buffer. The specific conditions are detailed in Table 1. Pronounced enrichment and separation of acidic, main and basic species were achieved, with AR % reduced by 9.4% at 76% yield.

Figure 19:
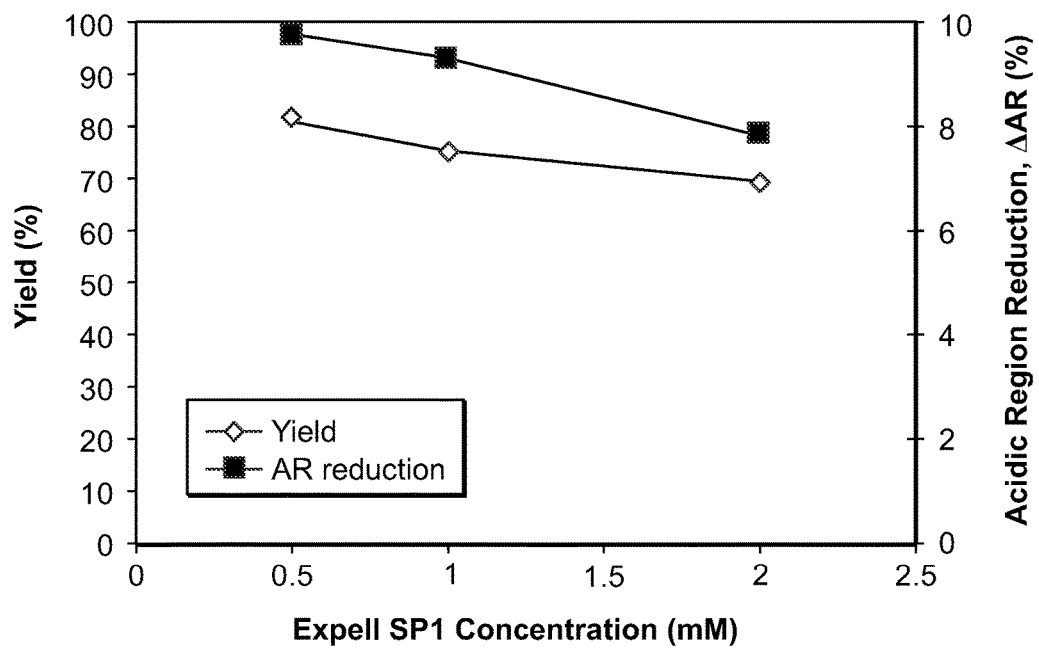
FIG. 19 depicts the effect of Expell SP1™ concentration on acidic species reduction in mAb X by Poros XS displacement chromatography.

The effect of Expell SP1™ concentration on AR reduction for mAb X was measured in the pH 6 Tris/Acetate buffer. As shown in FIG. 19, increasing the Expell SP1™ concentration from 0.5 to 2 mM decreased the ΔAR % for mAb X from 9.8% at 81% yield to 7.9% at 69% yield.

Figure 20:
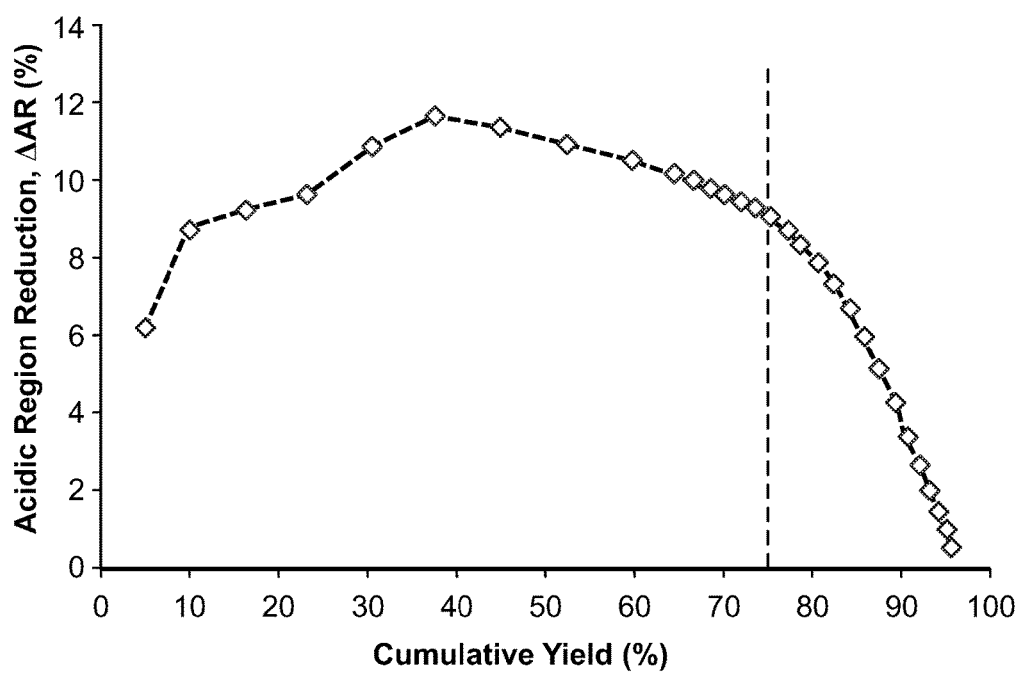
FIG. 20 depicts the reduction of acidic species in mAb X by Poros XS two-step displacement chromatography using Expell SP1™.

The two-step displacement scheme was evaluated for mAb X. As shown in Table 2, the displacement process comprised of 22 CV of 0.5 mM Expell SP1™ and 12 CV of 2 mM Expell SP1™ at pH 6. The protein displacement profile was completed within 30 CV of total displacing buffer volume, which was 30% less than that required for one-step displacement separation. The reduction of AR % versus product yield is shown in FIG. 20. The total AR % in product pool was reduced by ~9% at ~75% yield, again comparable to that obtained with one-step displacement process using 0.5 mM Expell SP1™ buffer.

Example 4. Displacement Chromatography Performance of Protamine Sulfate for mAb X on Poros XS Resin Protamine sulfate was also evaluated for separating acidic species for mAb X on Poros XS resin. The feed material for this set of experiments contained about 12-16% acidic and 12-13% basic species. The results for this system are shown in the following sections.

Figure 21:
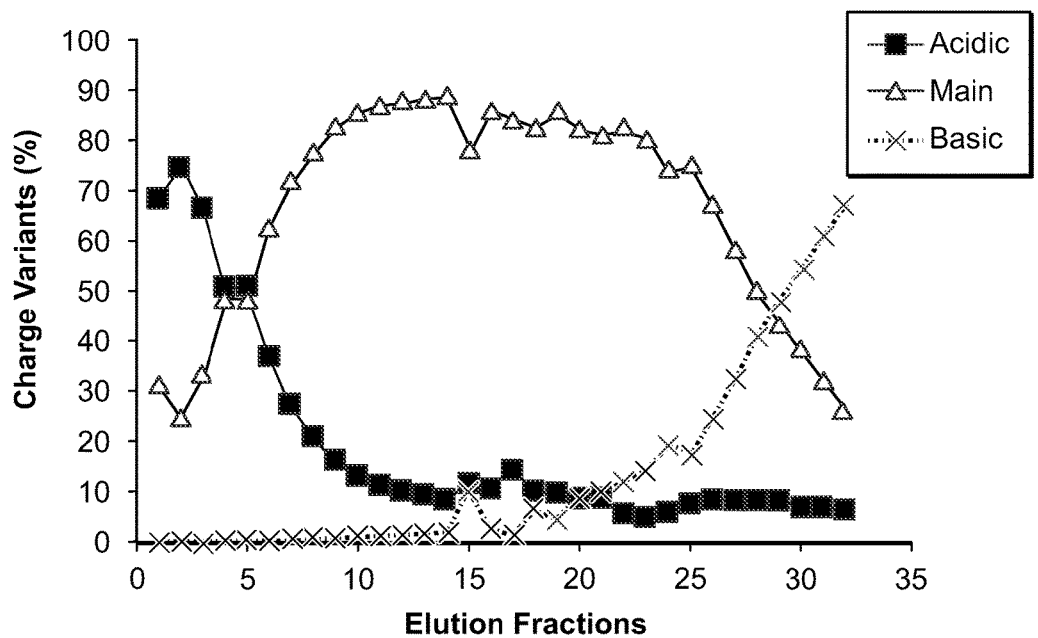
FIG. 21 depicts the separation of mAb X charge variants by Poros XS displacement chromatography using protamine sulfate.
Figure 22:
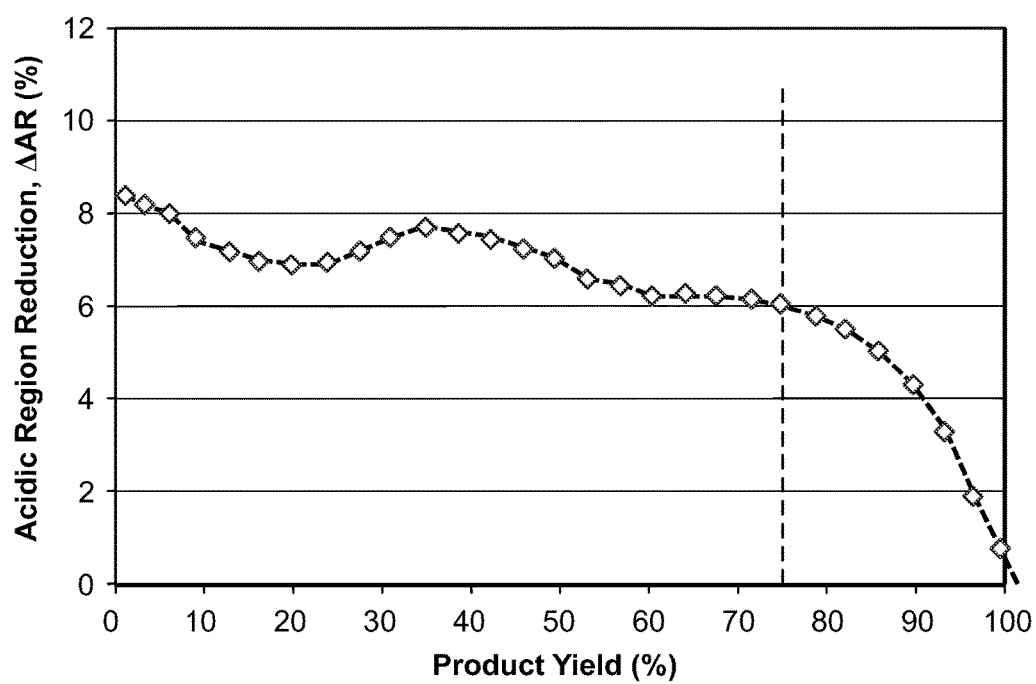
FIG. 22 depicts the reduction of acidic species in mAb X by Poros XS displacement chromatography using protamine sulfate.

A representative set of variant separation profiles are shown in FIGS. 21 and 22. In this experiment, the Poros XS column was loaded with ~36 g/L of mAb X at pH 6, 6.5 mS/cm binding condition, and was displaced using 0.25 mM protamine sulfate in a pH 6, 6.5 mS/cm Tris/Acetate buffer. The specific conditions are detailed in Table 1. Pronounced enrichment and separation of acidic, main and basic species were achieved, with AR level reduced by 6% at 75% yield.

Figure 23:
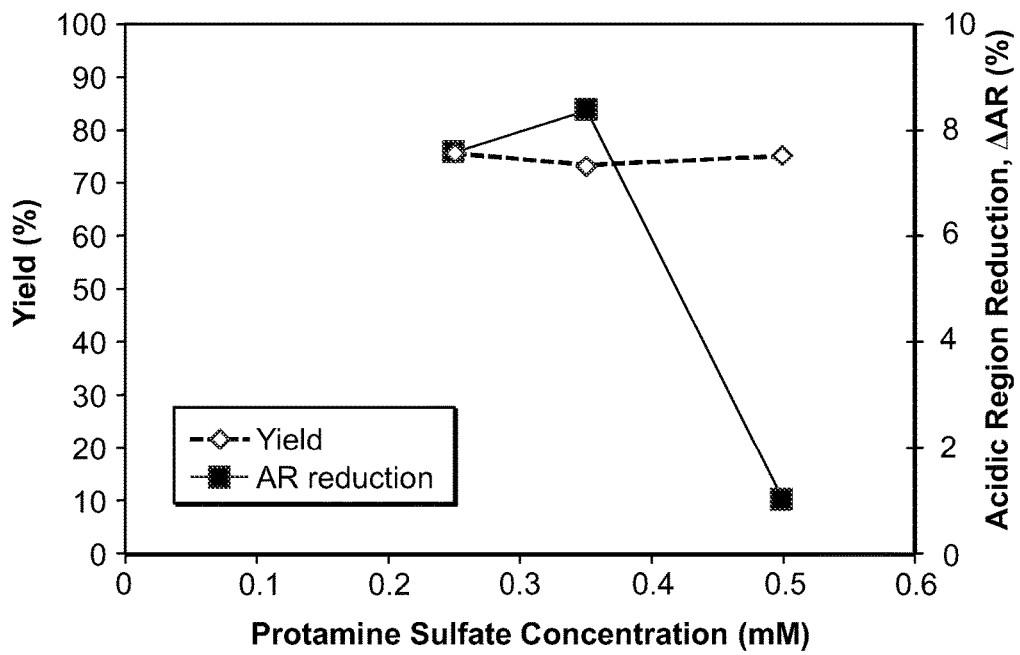
FIG. 23 depicts the effect of protamine sulfate concentration on acidic species reduction in mAb X by Poros XS displacement chromatography.

The effect of protamine sulfate concentration on mAb X AR reduction was measured in a pH 6 Tris/Acetate buffer, as shown in FIG. 23. In this case, the protamine sulfate concentration strongly affects the AR clearance in a relatively small protamine concentration range (i.e., from 0.35 to 0.5 mM). Nevertheless, over 8% of AR reduction can be achieved at pH 6 for mAb X at acceptable yield (≥70%).

Figure 24:
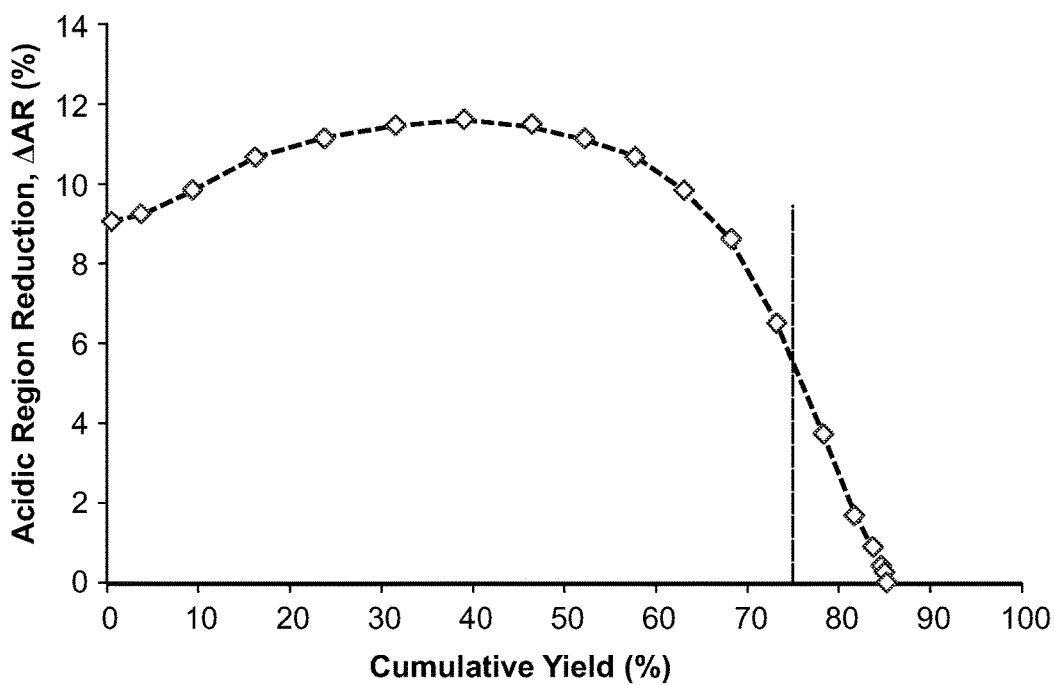
FIG. 24 depicts the reduction of acidic species in mAb X by Poros XS two-step displacement chromatography using protamine sulfate.

The two-step displacement scheme was evaluated for mAb X with protamine sulfate. In this experiment, the displacement process comprised of 10 CV of 0.35 mM Expell and 10 CV of 0.5 mM Expell at pH 6 (see Table 2). The protein displacement profile was completed in ~15 CV of total displacing buffer volume, representing ~26% reduction of buffer volume relative to the one-step displacement operation. The reduction of AR % versus product yield is shown in FIG. 24. The product pool AR level was reduced by ~6% at ~75% yield.

Figure 25:
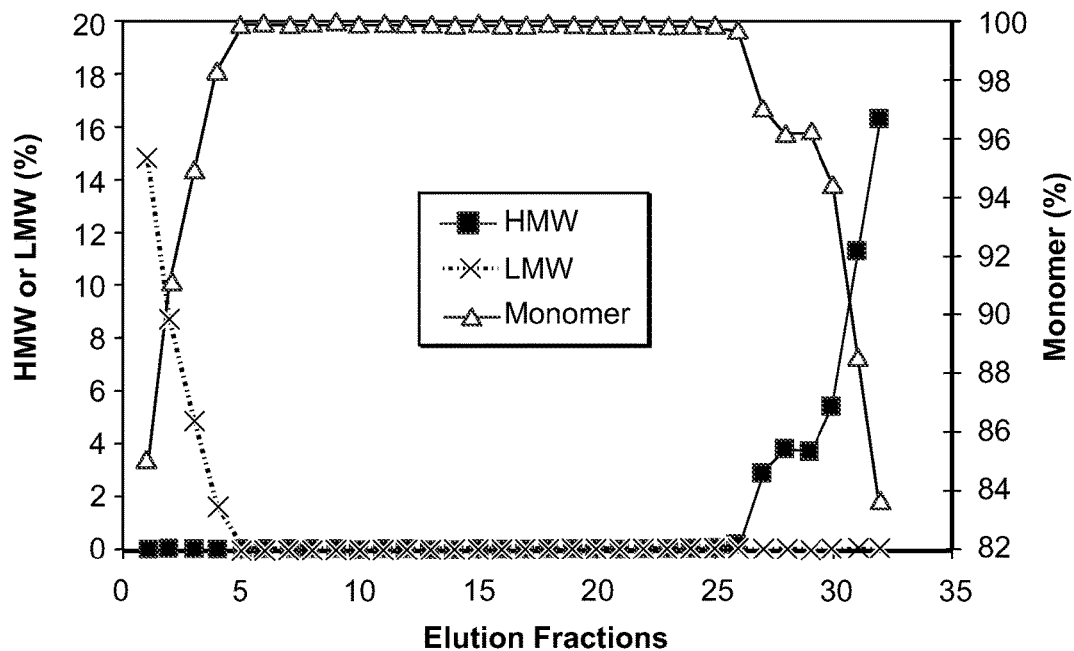
FIG. 25 depicts the separation of mAb X size variants by Poros XS displacement chromatography using protamine sulfate.

The mAb X BDS has about 0.74% of aggregates, which can be further reduced during the protamine sulfate displacement process. FIG. 25 shows the size variant profiles of mAb X as displaced by a 0.25 mM protamine sulfate, pH 6 buffer (i.e., the one-step displacement run shown in FIGS. 21 and 22). The aggregates were all enriched at the end of the displacement train, which differs from the observations with Adalimumab. Using the same product pooling strategy based on AR reduction, the monomer level was enhanced to 99.9% (Table 6).

Example 5. Displacement Chromatography Performance of Expell SP1™ for mAb Y on Poros XS Resin The displacement separation performance of Expell SP1™ was further assessed for mAb Y on Poros XS resin. The mAb Y has a pI of 7-7.5, much lower than Adalimumab and mAb X. An mAb Y protein A eluate was used in this study, which contained about 22% acidic species and 15% basic species.

Figure 26:
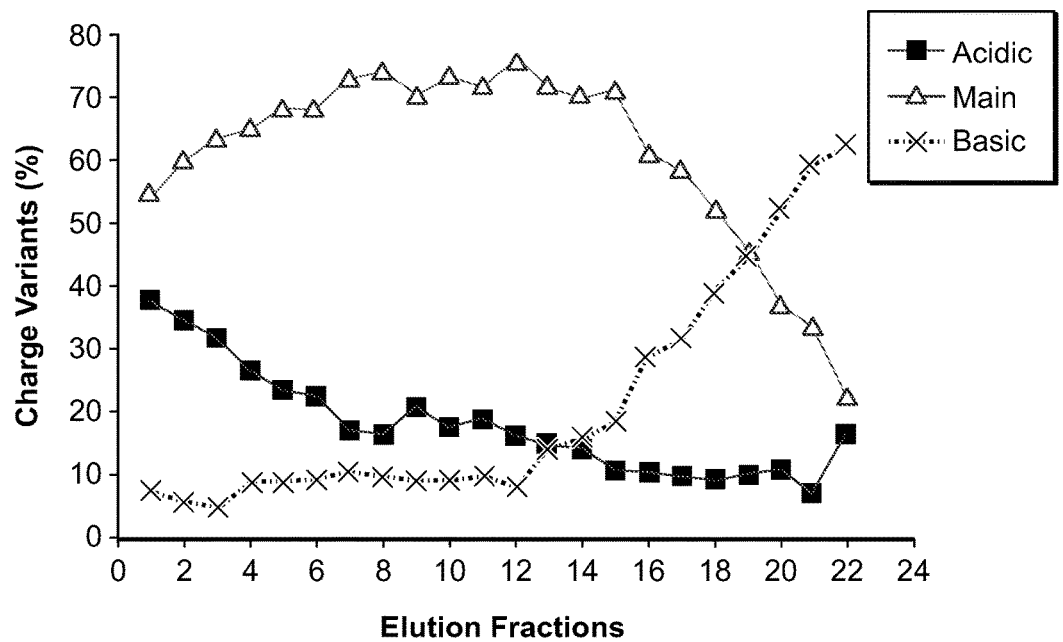
FIG. 26 depicts the separation of mAb Y charge variants by Poros XS displacement chromatography using Expell SP1™.
Figure 27:
FIG. 27 depicts the reduction of acidic species in mAb Y by Poros XS displacement chromatography using Expell SP1™.

An appropriate set of displacement conditions for mAb Y is shown in Table 1. The equilibration, wash and displacement buffers are all at pH 5 with conductivity around 6 mS/cm. The 0.5 mM Expell SP1™ buffer generated the desired displacement profile. The sample fractions from this run were analyzed by cation exchange HPLC. FIGS. 26 and 27 indicate the distribution of charge variant species and the cumulative ΔAR % versus product yield, respectively. A 6.6% decrease in AR % was observed at 74% yield under such condition.

Example 6. Displacement Chromatography Performance of Protamine Sulfate for Adalimumab on Capto MMC (Multimodal) Resin Capto MMC™ is a mixed mode resin based on weak cation-exchange and hydrophobic interaction mechanism. Its capability for acidic species and aggregates removal by displacement chromatography was assessed here. The Adalimumab feed material for this set of experiments contained about 20-21% total AR. The results for protamine sulfate system are shown in the following sections.

Figure 28:
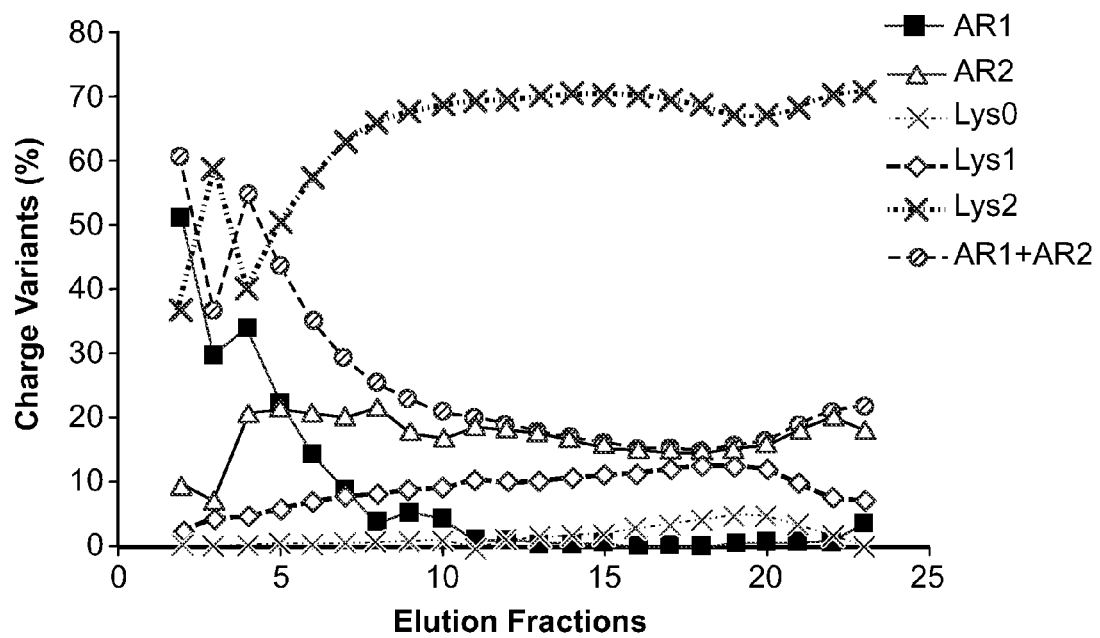
FIG. 28 depicts the separation of Adalimumab charge variants by Capto MMC displacement chromatography using protamine sulfate.
Figure 29:
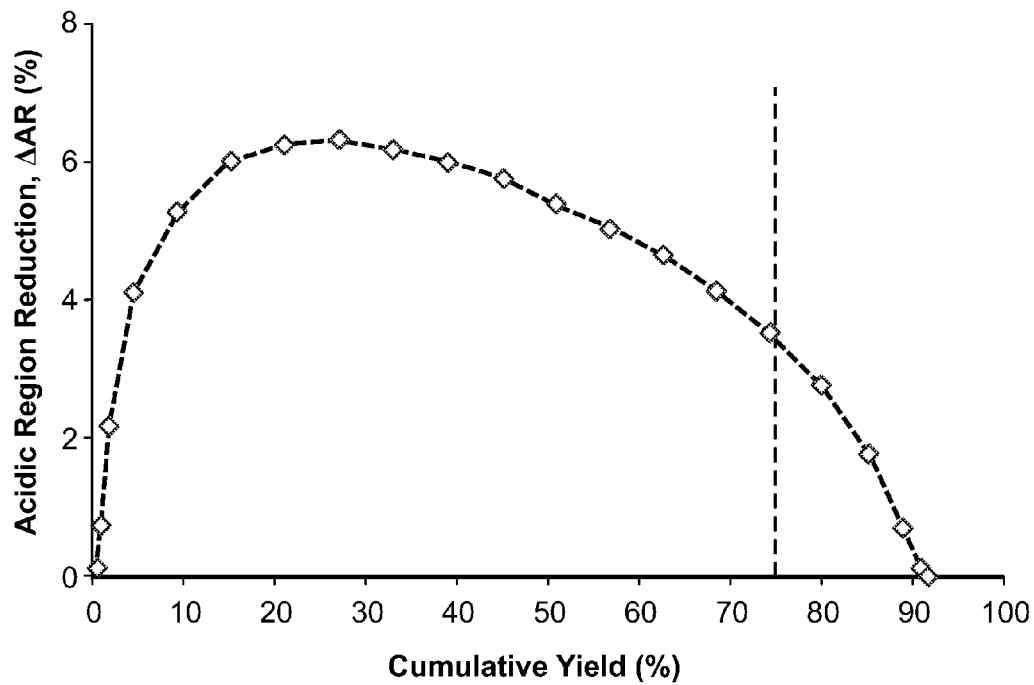
FIG. 29 depicts the reduction of acidic species in Adalimumab by Capto MMC displacement chromatography using protamine sulfate.

A representative set of variant separation profiles are shown in FIGS. 28 and 29. In this experiment, the Capto MMC column was equilibrated with a 140 mM Tris/acetate, pH 7 buffer (~5.7 mS/cm), loaded with ~34 g/L of Adalimumab at pH 7.5 and 5.3 mS/cm binding condition, briefly washed with EQ buffer and then displaced with 0.35 mM protamine sulfate in the pH 7 EQ buffer. A typical displacement chromatogram was generated under such experimental condition. As shown in FIG. 10, Capto MMC also showed enrichment of each variant in the train, yielding total AR reduction of ~4% at ~75% yield. The shape of the ΔAR % versus yield curve (FIG. 29) differs from that given by the Poros XS resin, possibly due to stronger binding of each protein species (related to secondary mode of interaction) by this mixed mode ligand.

The buffer pH and protamine sulfate concentrations were varied to assess the overall AR clearance by Capto MMC displacement chromatography. Table 7 summarized the results for three runs. Overall, 3-5% of AR reduction can be achieved for Adalimumab when using protamine sulfate as a displacer for Capto MMC resin.

TABLE 6

Step yield & product quality in mAb X before and after Poros XS displacement chromatography using protamine sulfate

| | Yield % | Acidic % | Main % | HMW % | Monomer % |
| --- | --- | --- | --- | --- | --- |
| Feed | — | 12.3 | 75.7 | 0.7 | 99.3 |
| Product pool | 79 | 4.7 | 80.8 | 0.1 | 99.9 |

TABLE 7

AR removal for Adalimumab by Capto MMC displacement chromatography using protamine sulfate

| Run No. | EQ/Displacing buffer pH | Load pH | Protamine Conc. (mM) | Yield (%) | ΔAR % |
| --- | --- | --- | --- | --- | --- |
| 1 | 7 | 7 | 0.5 | 75 | 3.1 |
| 2 | 7 | 7.5 | 0.35 | 75 | 4.0 |
| 3 | 7.25 | 7.5 | 0.25 | 78 | 5.2 |

The clearance of aggregates by Capto MMC displacement chromatography is illustrated in Table 8. The same operating conditions as described for obtaining the results in Table 7 were used here. The product pool monomer level was enhanced from 98.8% in the feed to 99.4% with aggregates reduced from 1.0% to 0.5%.

TABLE 8

Step yield & product quality in Adalimumab before and after Capto MMC displacement chromatography using protamine sulfate

| | Yield % | AR1 % | AR2 % | Lys Sum % | HMW % | Monomer % | LMW % |
|---|---|---|---|---|---|---|---|
| Feed | — | 4.4 | 16.5 | 79.1 | 1.0 | 98.8 | 0.2 |
| Product pool | 75 | 2.5 | 14.4 | 83.1 | 0.5 | 99.4 | 0.1 |

Figure 30:
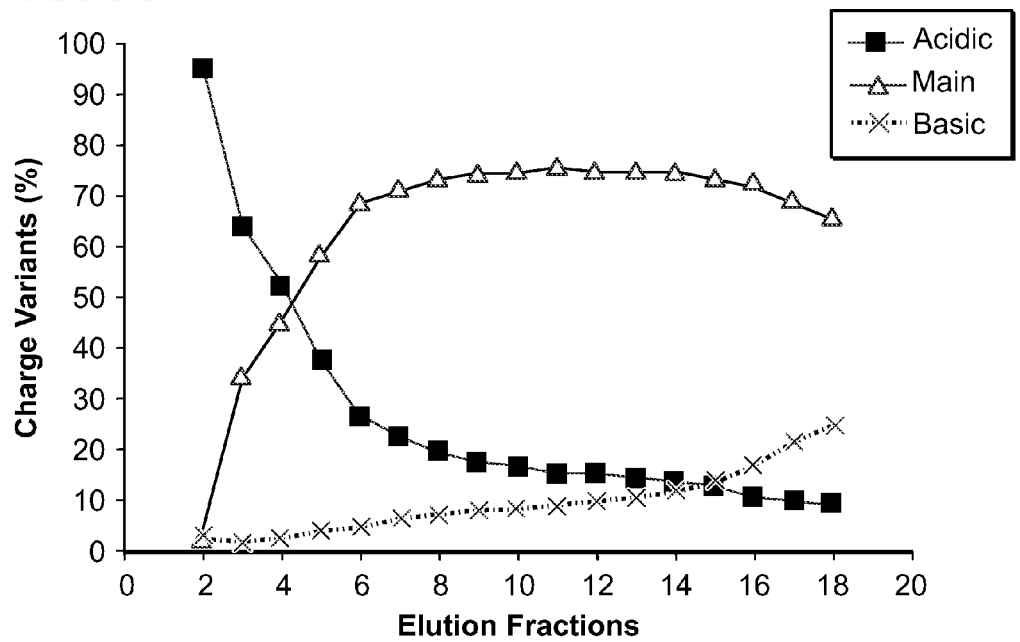
FIG. 30 depicts the separation of mAb X charge variants by Capto MMC displacement chromatography using protamine sulfate.
Figure 31:
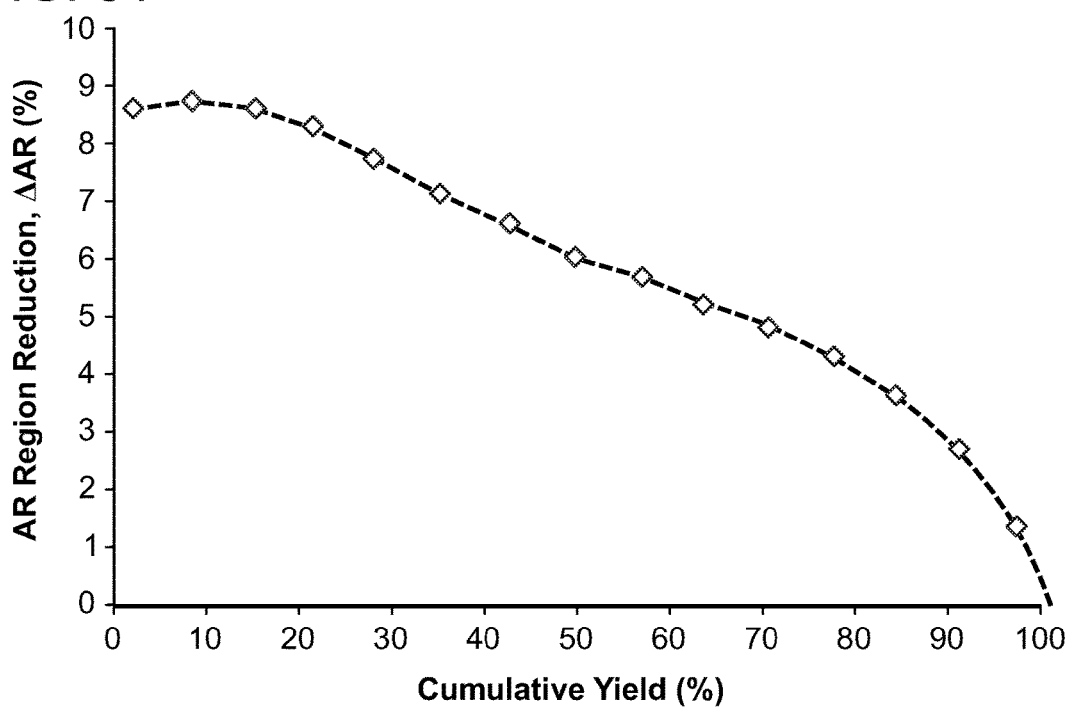
FIG. 31 depicts the reduction of acidic species in mAb X by Capto MMC displacement chromatography using protamine sulfate.

Example 7. Displacement Chromatography Separation of Protamine Sulfate for mAb X on Capto MMC Resin Protamine sulfate was evaluated for removing mAb X acidic species on Capto MMC resin. The same feed material as shown in Example 4 was used for this set of experiments. As detailed in Table 3, the pH and protamine concentrations were varied in order to generate desired displacement profile. One representative set of working condition is to load Capto MMC column with 40 g/L of mAb X at pH 7.5 and ~6 mS/cm, and to use 0.25 mM protamine sulfate in the pH 7.5, ~6 mS/cm EQ buffer for displacement (Table 3). The separation of charge variants and AR reduction as a function of product recovery are shown in FIGS. 30 and 31, respectively. In this case, 3-5% of AR reduction was resulted at product yield of 70-90%.

The effect of protamine sulfate concentration on mAb X AR reduction by Capto MMC resin was measured in a pH 7, 6 mS/cm Tris/Acetate buffer, as shown in Table 9. Varying the protamine concentration from 0.25 mM to 0.5 mM had very little effect on ΔAR % and product yield, which is quite different from the observations with the Poros XS resin (FIG. 23). The mixed mode MMC resin gave over 3% AR clearance under such selected conditions.

TABLE 9

Reduction of AR level by Capto MMC displacement chromatography for mAb X at different protamine sulfate concentrations

| Expell concentration (mM) | Yield (%) | ΔAR (%) |
|---|---|---|
| 0.25 | 75 | 3.4 |
| 0.5 | 77 | 3.3 |

Figure 32:
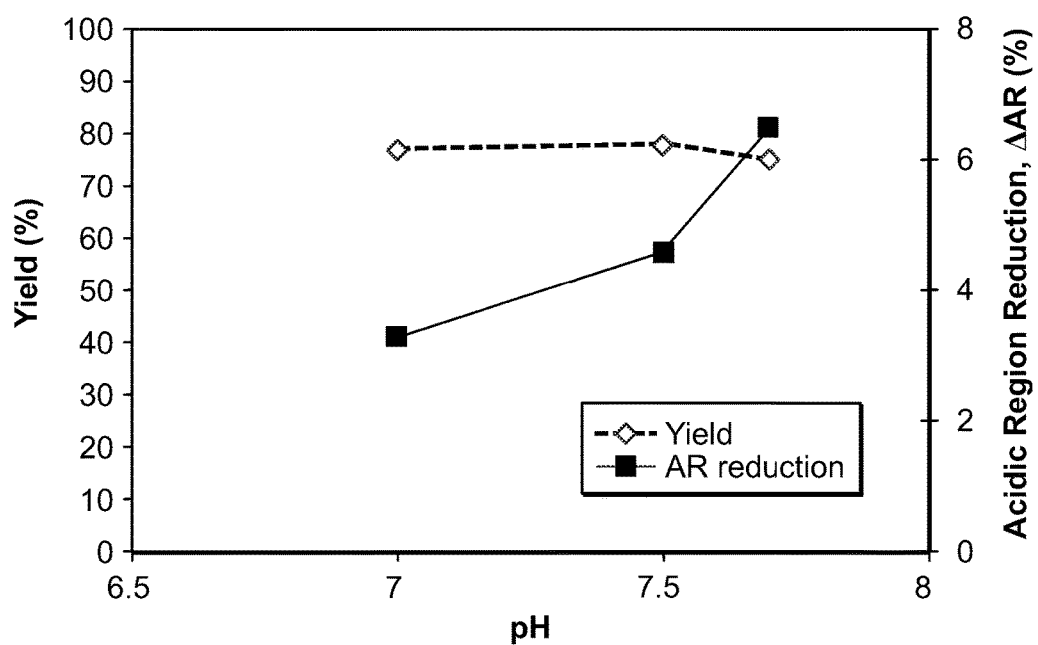
FIG. 32 depicts the effect of pH on acidic species reduction in mAb X by Capto MMC displacement chromatography.
Figure 33:
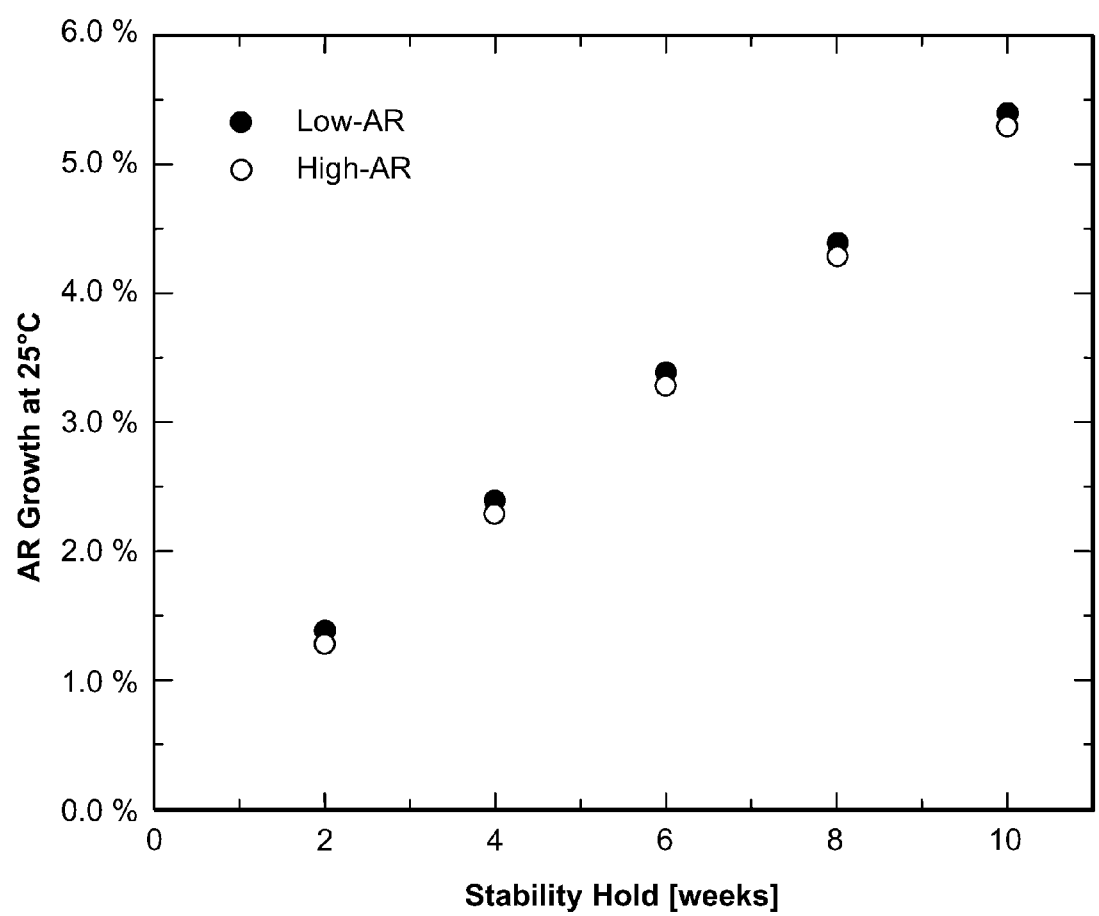
FIG. 33 depicts the AR Growth at 25° C. of low and high AR containing samples.

The effect of displacing buffer pH on AR clearance for mAb X was measured at 0.25 mM protamine sulfate concentration in Tris/Acetate buffer. In this set of experiments, the column was conditioned with an EQ buffer at the respective displacing buffer pH, loaded with protein feed at the same pH and ~6 mS/cm followed by a brief EQ buffer wash before starting the displacement phase. As shown in FIG. 32, ΔAR % increases from 3.3 to 6.5% as pH varies from 7 to 7.7.

The Capto MMC resin also removes aggregates during protamine sulfate displacement chromatography. Table 10 shows the level of charge and size variants of mAb X in product eluate when using 0.5 mM protamine sulfate, pH 7.5 (~6 mS/cm) displacing buffer for separation. The product pool monomer level was enhanced from 98.7% in the feed to 99.2% with aggregate and fragment levels reduced by 50% and 28%, respectively.

TABLE 10

Step yield & product quality for mAb X before and after Capto MMC displacement chromatography using protamine sulfate

| | Yield % | Acidic % | Main % | HMW % | Monomer % | LMW % |
|---|---|---|---|---|---|---|
| Feed | — | 16.8 | 74.0 | 0.6 | 98.7 | 0.7 |
| Product pool | 77 | 12.4 | 71.8 | 0.3 | 99.2 | 0.5 |

Example 8. Displacement Chromatography Separation of Protamine Sulfate for mAb Y on Capto MMC Resin Protamine sulfate was also evaluated for removing mAb Y acidic species on Capto MMC resin. The same feed material as shown in Example 5 was used for the experiments here. Two sets of conditions were evaluated here. In one experiment, the equilibration, wash and displacement buffers were adjusted to pH 5.5 and ~6.5 mS/cm, and the displacement buffer contained 0.25 mM protamine sulfate. In the other experiment, all those buffers were adjusted to pH 5, ~6.5 mS/cm and the protamine sulfate concentration was 0.5 mM. In both runs the feed was adjusted to pH 5.5, 5.2-5.5 mS/cm and loaded to the Capto MMC column at ~40 g/L loading level. As shown in Table 11, both sets of conditions resulted in AR % decrease by 5-7% in product pool. In addition, significant aggregates and fragments reduction was achieved with the same product pooling strategy.

TABLE 11

Step yield & product quality for mAb Y before and after Capto MMC displacement chromatography using protamine sulfate

| Conditions | Sample | Yield % | Acidic % | Main % | HMW % | Monomer % | LMW % |
|---|---|---|---|---|---|---|---|
| pH 5.5, 0.25 mM Protamine | Feed | — | 16.4 | 75.8 | 8.5 | 91.0 | 0.5 |
| | Product pool | 76 | 9.8 | 79.4 | 2.0 | 97.6 | 0.4 |
| pH 5, 0.5 mM Protamine | Feed | — | 20.9 | 72.8 | 6.3 | 93.2 | 0.5 |
| | Product pool | 75 | 15.9 | 81.1 | 1.6 | 98.2 | 0.2 |

Summary of Examples 1-8

Examples 1-8 above, demonstrate the use of cation exchange and mixed mode displacement chromatography for effectively reducing acidic species along with various other impurities from different monoclonal antibody feed streams. Under appropriate (or relatively weak) binding conditions, cationic molecules with high affinity for a CEX or multimodal ligand (such as Expell SP1™ and protamine sulfate) can induce the formation of charge variant displacement train, wherein the acidic population is enriched in the front followed by the main isoform, and, thereafter, the basic population. Thus, in certain embodiments, exclusion of those earlier fractions from the remainder eluate results in an AR-reduced product. Alternatively, exclusion of the fractions following the main isoform results in a Lys variant- or basic species-reduced product.

Also demonstrated in the preceding experiments is the fact that the operating pH and displacer concentration can strongly affect the displacement profile and as a result the charge variant, product aggregate, product fragment, and HCP clearance profile. The selection of a particular operating regime with regard to charge variant reduction depends, in general, on the specific protein-resin-displacer system. For example, for Adalimumab, significant AR reduction can be achieved using a displacing buffer with pH in the range of 6-8 with displacer concentration as low as 0.25-0.5 mM. The total AR level (%) in Adalimumab product pool can be reduced by over 10% with an acceptable processing yield (≥75%) from a CEX displacement chromatography process, or 4-7% from a mixed mode displacement chromatography process. Along with acidic species, other product variants or process impurities such as basic species, aggregates, fragments and HCP can be selectively collected or reduced to meet the quality requirements. In addition to the surprisingly effective preparative scale standard one-step displacement operation, unconventional displacement separation schemes are shown above to have unexpected properties, including two-step displacement chromatography and linear gradient displacement chromatography, which can significantly reduce buffer volumes and shorten the processing time without compromising the charge variant, product aggregate, product fragment, and HCP clearance at a given yield target.

The instant invention provides a method for reducing acidic species for a given protein of interest. For example, adalimumab was prepared using a combination of AEX and CEX technologies to produce a Low-AR and High-AR sample with a final AR of 2.5% and 6.9%, respectively. Both samples were incubated in a controlled environment at 25° C. and 65% relative humidity for 10 weeks, and the AR measured every two weeks. FIG. 23 shows the growth of AR for each sample over the 10 week incubation. It is evident from FIG. 23 the growth rate of AR is linear and similar between both the Low-AR and High-AR samples. Based on these results, the reduced AR compositions of the invention can be stored 3-fold longer before reaching the same AR level as the High-AR sample. These surprising results are very beneficial for storage, handling, and use of an antibody or other protein for therapeutic use.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for producing a low acidic species composition comprising an anti-TNFα antibody, or antigen-binding portion thereof, wherein the anti-TNFα antibody, or antigen-binding portion thereof, comprises a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4, the method comprising:

(a) contacting a first composition comprising the anti-TNFα antibody, or antigen-binding portion thereof with a chromatography media, wherein the first composition comprises more than 10% acidic species of the anti-TNFα antibody, or antigen-binding portion thereof, and wherein the anti-TNFα antibody, or antigen-binding portion thereof binds to the chromatography media;

(b) displacing the anti-TNFα antibody, or antigen-binding portion thereof, bound to the chromatography media with a displacing buffer; and (c) collecting a second composition comprising the displaced anti-TNFα antibody, or antigen-binding portion thereof, wherein the second composition comprises less than 10% acidic species of the anti-TNFα antibody, or antigen-binding portion thereof, thereby producing a low acidic species composition.

2. The method of claim 1, wherein the pH of the displacing buffer is lower than the isoelectric point of the anti-TNFα antibody, or antigen-binding portion thereof.

3. The method of claim 1, wherein the displacing buffer carries a positive charge.

4. The method of claim 1, wherein the conductivity of the displacing buffer is about 2 mS/cm to about 20 mS/cm.

5. The method of claim 1, wherein one displacing buffer is used.

6. The method of claim 1, wherein displacing the anti-TNFα antibody, or antigen-binding portion thereof, bound to the chromatography media comprises using a first displacing buffer followed by using a second displacing buffer.

7. The method of claim 1, wherein displacing is achieved using linear displacement, a two-step displacement, or a multiple-step displacement.

8. The method of claim 1, wherein the second composition comprises less than 9% acidic species of the anti-TNFα antibody, or antigen-binding portion thereof.

9. The method of claim 1, wherein the second composition comprises less than 8% acidic species of the anti-TNFα antibody, or antigen-binding portion thereof.

10. The method of claim 1, wherein the second composition comprises less than 7% acidic species of the anti-TNFα antibody, or antigen-binding portion thereof.

11. The method of claim 1, wherein the second composition comprises less than 6% acidic species of the anti-TNFα antibody, or antigen-binding portion thereof.

12. The method of claim 1, wherein the second composition comprises less than 5% acidic species of the anti-TNFα antibody, or antigen-binding portion thereof.

13. The method of claim 1, wherein the second composition comprises less than 4.5% acidic species of the anti-TNFα antibody, or antigen-binding portion thereof.

14. The method of claim 1, wherein the second composition comprises less than 4% acidic species of the anti-TNFα antibody, or antigen-binding portion thereof.

15. The method of claim 1, wherein the second composition comprises less than 3% acidic species of the anti-TNFα antibody, or antigen-binding portion thereof.

16. The method of claim 1, wherein the second composition comprises less than 1.4% acidic species of the anti-TNFα antibody, or antigen-binding portion thereof.

17. The method of claim 1, wherein the displacing buffer comprises protamine sulfate.

18. The method of claim 1, wherein the displacing buffer comprises a quaternary ammonium salt.

19. The method of claim 1, wherein the chromatography media is an anion exchange adsorbent material.

20. The method of claim 1, wherein the chromatography media is a cation exchange adsorbent material.

21. The method of claim 20, wherein the cation exchange adsorbent material is a CEX membrane adsorber.

22. The method of claim 20, wherein cation exchange adsorbent material is a CEX resin.

23. The method of claim 1, wherein the chromatography media is a mixed mode media comprising cation exchange and hydrophobic interaction functional groups.

24. The method of claim 1, wherein the chromatography media is a mixed mode media selected from the group consisting of a cation exchange-based mixed mode resin and a cation-exchange-based mixed mode membrane adsorber.

25. The method of claim 1, wherein the displacing buffer comprises protamine sulfate, a quaternary ammonium salt, a polyelectrolyte, a polysaccharide, a low-molecular-mass dendrimer, an amino acid, a peptide, an antibiotic, a polyaromatic polyanionic compound, or an aminoglycoside-polyamine.

26. The method of claim 25, wherein the concentration of the protamine sulfate, quaternary ammonium salt, polyelectrolyte, polysaccharide, low-molecular-mass dendrimer, amino acid, peptide, antibiotic, polyaromatic polyanionic compound, or aminoglycosidepolyamine in the displacing buffer is 0.1 mM to 10 mM.

27. The method of claim 1, wherein the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2.

28. The method of claim 27, wherein the anti-TNFα antibody, or antigen-binding portion thereof, is adalimumab, or an antigen-binding portion thereof.

* * * * *

SEQUENCE LISTING

```
<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
```

```
                1               5                  10                  15
Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
 1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc     60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc     60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag taccctggt caccgtctcg     360 agt                                                                   363

<210> SEQ ID NO 11
<211> LENGTH: 214
```

```
<212> TYPE: PRT
<213> ORGANISM: Artificial Sequence
<220> FEATURE:
<223> OTHER INFORMATION: adalimumab light chain

<400> SEQUENCE: 11

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110
```

-continued

```
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
        435                 440                 445
Pro Gly Lys
    450
```